United States Patent
Enomura et al.

(10) Patent No.: US 11,202,738 B2
(45) Date of Patent: Dec. 21, 2021

(54) METAL OXIDE PARTICLES AND METHOD OF PRODUCING THE SAME

(71) Applicant: M. TECHNIQUE CO., LTD., Izumi (JP)

(72) Inventors: Masakazu Enomura, Izumi (JP); Daisuke Honda, Izumi (JP)

(73) Assignee: M. TECHNIQUE CO., LTD., Izumi (JP)

( * ) Notice: Subject to any disclaimer, the term of this patent is extended or adjusted under 35 U.S.C. 154(b) by 34 days.

(21) Appl. No.: 15/759,309

(22) PCT Filed: Jun. 3, 2016

(86) PCT No.: PCT/JP2016/066542
§ 371 (c)(1),
(2) Date: Mar. 12, 2018

(87) PCT Pub. No.: WO2017/061140
PCT Pub. Date: Apr. 13, 2017

(65) Prior Publication Data
US 2018/0179060 A1    Jun. 28, 2018

(30) Foreign Application Priority Data

Oct. 5, 2015 (JP) .............................. JP2015-197556
Jun. 2, 2016 (JP) .............................. JP2016-111346

(51) Int. Cl.
*C01B 13/36* (2006.01)
*C01G 49/06* (2006.01)
(Continued)

(52) U.S. Cl.
CPC .............. *A61K 8/0245* (2013.01); *A61K 8/04* (2013.01); *A61K 8/19* (2013.01); *A61K 8/25* (2013.01);
(Continued)

(58) Field of Classification Search
CPC ....................................................... C01G 39/06
See application file for complete search history.

(56) References Cited

U.S. PATENT DOCUMENTS

| | | |
|---|---|---|
| 4,487,869 A | 12/1984 | Panush |
| 4,517,249 A | 5/1985 | Panush |

(Continued)

FOREIGN PATENT DOCUMENTS

| | | |
|---|---|---|
| EP | 0 988 853 A1 | 3/2000 |
| EP | 2305607 A1 | 4/2011 |

(Continued)

OTHER PUBLICATIONS

Machine translation JP 2003-277644 (Year: 2003).*
(Continued)

*Primary Examiner* — Alexandre F Ferre
(74) *Attorney, Agent, or Firm* — Birch, Stewart, Kolasch & Birch, LLP

(57) ABSTRACT

A method of producing efficiently and stably core-shell type oxide particles, wherein the entire surface of the core oxide particles is uniformly coated with the shell oxide, includes at least two steps of: Step 1 of precipitating the core oxide particles in a mixed fluid prepared by mixing an oxide raw material liquid for core and an oxide precipitation solvent and Step 2 of coating the entire surface of the core oxide particles uniformly with the shell oxide by mixing the mixed fluid and an oxide raw material liquid for shell. (A) At least Steps 1 and 2 are performed continuously between at least two processing surfaces 1 and 2 which are capable of approaching to and separating from each other, at least one of which rotates relatively to the other; (B) after Step 1, Step 2 is completed within a prescribed time during which the core oxide particles do not aggregate in the mixed fluid; or (C) Step 1 and Step 2 are controlled so that the primary particle diameter of the core-shell type oxide particles is
(Continued)

190% or less relative to the primary particle diameter of the core oxide particles.

14 Claims, 14 Drawing Sheets

(51) Int. Cl.
| | |
|---|---|
| *C01G 9/02* | (2006.01) |
| *C09D 7/40* | (2018.01) |
| *A61K 8/02* | (2006.01) |
| *C09D 5/33* | (2006.01) |
| *C09C 3/06* | (2006.01) |
| *C09C 1/04* | (2006.01) |
| *C09C 1/24* | (2006.01) |
| *C09C 3/08* | (2006.01) |
| *A61K 8/04* | (2006.01) |
| *A61K 8/19* | (2006.01) |
| *A61K 8/25* | (2006.01) |
| *A61K 8/49* | (2006.01) |
| *A61Q 1/02* | (2006.01) |
| *A61Q 17/04* | (2006.01) |
| *C09D 1/00* | (2006.01) |
| *C09D 5/32* | (2006.01) |
| *C08K 3/34* | (2006.01) |
| *C09D 7/61* | (2018.01) |
| *C01B 33/12* | (2006.01) |
| *C08K 3/22* | (2006.01) |
| *C08K 9/02* | (2006.01) |
| *B82Y 30/00* | (2011.01) |

(52) U.S. Cl.
CPC .............. *A61K 8/4926* (2013.01); *A61Q 1/02* (2013.01); *A61Q 17/04* (2013.01); *C01B 13/36* (2013.01); *C01B 33/12* (2013.01); *C01G 9/02* (2013.01); *C01G 49/06* (2013.01); *C08K 3/34* (2013.01); *C09C 1/043* (2013.01); *C09C 1/24* (2013.01); *C09C 3/063* (2013.01); *C09C 3/08* (2013.01); *C09D 1/00* (2013.01); *C09D 5/004* (2013.01); *C09D 5/32* (2013.01); *C09D 7/61* (2018.01); *C09D 7/67* (2018.01); *A61K 2800/413* (2013.01); *A61K 2800/43* (2013.01); *A61K 2800/621* (2013.01); *A61K 2800/651* (2013.01); *B82Y 30/00* (2013.01); *C01P 2002/72* (2013.01); *C01P 2002/82* (2013.01); *C01P 2004/04* (2013.01); *C01P 2004/32* (2013.01); *C01P 2004/64* (2013.01); *C01P 2004/84* (2013.01); *C08K 9/02* (2013.01); *C08K 2003/2265* (2013.01); *C08K 2201/003* (2013.01); *C08K 2201/011* (2013.01)

(56) References Cited

U.S. PATENT DOCUMENTS

| | | | |
|---|---|---|---|
| 5,827,507 | A | 10/1998 | Oshima et al. |
| 6,235,270 | B1 | 5/2001 | Ishii et al. |
| 2002/0037262 | A1 | 3/2002 | Tanaka et al. |
| 2002/0071948 | A1 | 6/2002 | Duff et al. |
| 2010/0155310 | A1 | 6/2010 | Enomura |
| 2011/0033400 | A1* | 2/2011 | Ehlis .................. A61K 8/19 424/60 |
| 2011/0207869 | A1* | 8/2011 | Katusic .................. C01G 49/00 524/442 |
| 2012/0097522 | A1 | 4/2012 | Bagabas et al. |
| 2013/0156682 | A1 | 6/2013 | Kuraki et al. |
| 2013/0303658 | A1* | 11/2013 | Katusic .................. C01G 49/00 523/210 |
| 2014/0037519 | A1 | 2/2014 | Kuraki et al. |
| 2014/0134216 | A1* | 5/2014 | Takada .................. A61K 8/0245 424/401 |
| 2015/0030760 | A1 | 1/2015 | Enomura |
| 2015/0202655 | A1 | 7/2015 | Nakano et al. |
| 2015/0217332 | A1 | 8/2015 | Fujii et al. |
| 2015/0246395 | A1 | 9/2015 | Maekawa et al. |

FOREIGN PATENT DOCUMENTS

| | | | |
|---|---|---|---|
| JP | 59-75960 | A | 4/1984 |
| JP | 60-106866 | A | 6/1985 |
| JP | 63-54979 | A | 3/1988 |
| JP | 8-12961 | A | 1/1996 |
| JP | 2000-2274 | A | 1/2000 |
| JP | 2003-277644 | A | 10/2003 |
| JP | 2008-239460 | A | 10/2008 |
| JP | 2009-67613 | A | 4/2009 |
| JP | 2009-132596 | A | 6/2009 |
| JP | 2009-263547 | A | 11/2009 |
| JP | 4868558 | B1 | 2/2012 |
| JP | 2012-216292 | A | 11/2012 |
| JP | 2013-82621 | A | 5/2013 |
| JP | 2014-42891 | A | 3/2014 |
| JP | 2014-42892 | A | 3/2014 |
| JP | 2014-74222 | A | 4/2014 |
| WO | WO 98/26011 | A1 | 6/1998 |
| WO | WO 98/47476 | A1 | 10/1998 |
| WO | WO 2009/008393 | A1 | 1/2009 |
| WO | WO 2013/128592 | A1 | 9/2013 |

OTHER PUBLICATIONS

European Search Report, dated Mar. 26, 2019, for European Application No. 16853296.8.
Extended European Search Report for European Application No. 16853296.8, dated Jun. 19, 2019.
International Search Report, issued in PCT/JP2016/066542, dated Aug. 2, 2016.

* cited by examiner (A)

(B)

METAL OXIDE PARTICLES AND METHOD OF PRODUCING THE SAME

TECHNICAL FIELD

The present inventions relate to metal oxide particles and a method of producing the same.

BACKGROUND ART

Oxide particles are materials used in a wide range of fields such as catalysts, conductive materials, magnetic materials, secondary electron emission materials, luminous bodies, heat absorbers, energy storage bodies, electrode materials, colorants, and the like. Since characteristics are changeable depending on the particle size, oxide particles having different particle diameter and crystallinity are required depending on the purpose or requirements. In particular, significantly different characteristics from those in a bulk state are exhibited by micronization of oxide particles, and thus, oxide particles are widely required materials now and in future. However, when two or more characteristics exhibited by micronization exist, there are cases that exhibition of only specific characteristics and suppression of other characteristics are desired depending on their usage. As an example, while both photocatalytic ability and ultraviolet absorbing ability are exhibited by micronization of metal oxide, suppression of photocatalyst is needed in case of using metal oxides microparticles as a colorant or ultraviolet protective agent.

As exemplified above, it has been known that specific characteristics exhibited in oxide particles can be suppressed by a method of coating the surface of the oxide particles with an oxide of a heterogeneous element (for example, Patent Literature 1).

In the method described in Patent Literature 1, oxide powders are dispersed in water containing an organic solvent, and the surface of the oxide particles are coated with silica by treatment with a silicon compound. However, it is very difficult to disperse the powdery oxide up to primary particles. A reaction solution for coating the oxide surface with silica is added to the oxide suspension at a constant rate for about 6 to 8 hours, and thereafter aging treatment is required for about 12 hours, so that the reaction conditions in the reaction vessel are successively changed, and uniformity of the concentration distribution of the reactants in the vessel is difficult, and it is much more difficult to coat the surface of each oxide particle with a silicon compound. In fact, in Patent Literature 1, precipitated particles are aggregated, and the aggregated particles are coated with silica as shown in FIG. 2. As described above, it is practically impossible in Patent Literature 1 to coat individual particles uniformly. Besides, since the process takes a long time, the method is not an efficient method. In particular, since the precipitation step and the coating step of the oxide particles are not associated, the method is extremely inefficient industrially in view of production of core-shell type oxide particles as a final product.

Patent Literatures 2 to 6 and 12 filed by the present applicant disclose a method of precipitating particles between two processing surfaces being capable of approaching to and separating from each other and rotating relative to each other. However, the method described in Patent Literature 2 is a method of producing oxide particles efficiently and stably, and a method of preparing core-shell type oxide particles wherein the surface is coated with oxides of a heterogeneous element is not disclosed.

On the other hand, Patent Literature 3 discloses an example in which amorphous silica particles are discharged from the space between the processing surfaces, and silver is uniformly coated on the surface of the particles. However, the discharged liquid containing amorphous silica and a silver nitrate solution are retained in a tubular container for a prescribed period of time to coat the surface of the amorphous silica particles with silver. Even when this method is applied to coating of the surface of the oxide particles obtained in Patent Literature 2 with an oxide of a heterogeneous element, it would be impossible to coat the entire surface of the particle uniformly.

Patent Literature 4 discloses that a fluid containing oxide particles and a fluid containing an acidic substance or hydrogen peroxide are mixed within 1 second after precipitation of oxide particles in order to adjust the dispersibility of the oxide particles. However, core-shell type oxide particles wherein the entire surface of the oxide particles are uniformly coated with an oxide of a heterogeneous element, cannot be produced by this method. Further, Patent Literature 4 does not even disclose inhibition of specific characteristics emitted by the oxide particles.

Further, Patent Literature 5 describes that photocatalytic activity of titanium dioxide particles can be controlled by coating the surfaces of the titanium dioxide particles with a substance such as an aluminum oxide or silicon oxide in the space between the processing surfaces. However, Patent Literature 5 does not disclose any relation between the precipitation step of titanium dioxide particles and the coating step of the precipitated titanium dioxide particles with an oxide such as a silicon oxide and the like. For this reason, it is difficult to coat stably the entire surface of individual core oxide particles with a shell oxide of a uniform heterogeneous element.

Patent Literature 6 discloses a method of producing metal microparticles, and discloses that core-shell type alloy particles or the like can be produced by introducing a plurality of fluids containing at least one kind of metals and/or metal compounds from separate introduction parts into the space between the processing surfaces. However, Patent Literature 6 does not disclose a method of producing core-shell type oxide particles in which both the core and the shell are oxides. Patent Literature 6 does not disclose uniformity of the shell coating either.

Patent Literature 7 discloses a method of producing a catalyst of metal A modified with metal B using an apparatus similar to those described in Patent Literatures 2 to 6. Patent Literature 7 also discloses that the form of both metal A and metal B may be an oxide; that it is preferable that the surface of metal A is completely or partially coated with metal B; and that it is more preferable that the catalyst is in a core-shell structure form consisting of a core part containing metal A as a main component and a shell part containing metal B as a main component, wherein the crystal structure of the catalyst is different from those of metal A and metal B. However, the form of the metal particles in the catalyst of the examples is not an oxide in terms of both metals A and B. The entire surface of metal A is not uniformly coated with metal B as far as the surface coating rates shown in Table 1 are concerned.

The present inventors have found that core-shell type oxide particles wherein the entire surface of the oxide particles is uniformly coated with an oxide of a heterogeneous element, can be produced efficiently and stably, by continuously performing precipitation of the core oxide particles and coating of the surface of the core oxide particles with the shell oxide. Thus, the present inventors have accomplished the present inventions.

Further, an example of the applications of the oxide particles is a raw material of a coating material. For example, not only color vividness and designability, but also durability such as weather resistance and light resistance are important for a coating material used for exterior walls of building materials, signboards, vehicles, or the like. Therefore, an ultraviolet protective substance is used for protecting a coating material or components contained in a coating material by a method of mixing the substance into the coating material or by a method of coating the substance on a coating film. In general, iron oxide, one of metal oxides, is effective for such substances. However, in addition to the ultraviolet protective ability, reduction of the influence of a visible light is required for not impairing the color characteristics such as coloration, color saturation, transparency and the like emitted by the coating material, and the designability of the product. Especially, iron oxide used for red coating materials for multilayer coating film is required to transmit a red light as much as possible, and to absorb a light other than a red light as much as possible.

As an iron oxide for protecting from an ultraviolet light, Patent Literature 8 discloses a coloring pigment for sunlight high reflecting coating material, comprising red iron oxide or yellow hydrous iron oxide having an average particle diameter of 10 to 300 nm. Patent Literature 9 discloses an iron oxide as a needle-shaped silica-coated Bengara red pigment having an average length of 500 nm and an average diameter of 100 nm. The iron oxide described in Patent Literature 8 or 9 may be used by mixing with the coating material described in Patent Literature 10 or 11.

However, the iron oxide or the silica-coated iron oxide described in Patent Literature 8 and Patent Literature 9 has a range in the wavelength range of 400 to 620 nm of the visible region where a reflectance exceeds 18%, and the color characteristics of a red coating material and the designability of a product are impaired. Thus, it was impossible to achieve both of the protection from an ultraviolet light and the transparency at the same time.

Patent Literature 12 filed by the present applicant discloses a method of producing various nanoparticles of an iron oxide and the like between two processing surfaces being capable of approaching to and separating from each other and rotating relative to each other. However, the described iron oxide nanoparticles are the nanoparticles of black iron oxide ($Fe_3O_4$: magnetite) and yellow iron oxide (FeOOH: goethite), and it is not described that these iron oxide nanoparticles have ability of protecting from an ultraviolet light and characteristic of transmission of a visible light.

CITATION LIST

Patent Literature

Patent Literature 1: WO 98/47476
Patent Literature 2: JP 4868558
Patent Literature 3: WO 2013/128592
Patent Literature 4: JP 2013-082621
Patent Literature 5: JP 2009-132596
Patent Literature 6: JP 2014-074222
Patent Literature 7: JP 2012-216292
Patent Literature 8: JP 2009-263547
Patent Literature 9: WO 98/26011

Patent Literature 10: JP 2014-042891
Patent Literature 11: JP 2014-042892
Patent Literature 12: WO 2009/008393

SUMMARY OF THE INVENTION

Technical Problem

An object of the present inventions is to provide a method of producing efficiently and stably core-shell type oxide particles wherein the entire surface of the core oxide particles is uniformly coated with a shell oxide of a heterogeneous element, by continuously performing precipitation of the core oxide particles and coating of the surface of the core oxide particles with the shell oxide.

In view of such circumstances, an object of the present inventions is to provide a silicon oxide-coated iron oxide composition for coating which has high transparency and is suitable for use in a coating material. An object of the present inventions is to provide a silicon oxide-coated iron oxide dispersion for coating which is effective in particular for a red color coated body, and has a transmittance of 2.0% or less for a light of a wavelength of 200 to 420 nm and a transmittance of 80% or more for a light of a wavelength of 620 to 800 nm.

An object of the present inventions is to provide a weather resistant composition for coating which protects the above coated body from an ultraviolet light, and is blended and used in a coating material constituting a coated body, and can be effectively applied to coated bodies having various colors, in particular to red color coated bodies.

Solution to the Problem

The present inventors have done intensive research to solve the above problems, and have found that the above objects are achieved by the methods mentioned below. Thus, the present inventors have accomplished the present inventions.

The present inventions provide a method of producing core-shell type oxide particles wherein the surface of the core oxide particles are coated with the shell oxide, comprising at least two steps of: Step 1 of precipitating the core oxide particles in a mixed fluid prepared by mixing an oxide raw material liquid for core containing at least an oxide raw material for core which is a raw material of the core oxide particles, and an oxide precipitation solvent containing at least an oxide precipitation substance for precipitating the core oxide particles; and Step 2 of coating the entire surface of the core oxide particles uniformly with the shell oxide by mixing the mixed fluid and an oxide raw material liquid for shell containing at least a shell oxide raw material which is a raw material of the shell oxide; and wherein the at least two steps are performed continuously between at least two processing surfaces which are capable of approaching to and separating from each other, at least one of which rotates relatively to the other.

The present inventions also provide a method of producing core-shell type oxide particles wherein the surface of the core oxide particles are coated with the shell oxide, comprising at least two steps of: Step 1 of precipitating the core oxide particles in a mixed fluid prepared by mixing an oxide raw material liquid for core containing at least an oxide raw material for core which is a raw material of the core oxide particles, and an oxide precipitation solvent containing at least an oxide precipitation substance for precipitating the core oxide particles; and Step 2 of coating the entire surface of the core oxide particles uniformly with the shell oxide by mixing the mixed fluid and an oxide raw material liquid for shell containing at least a shell oxide raw material which is a raw material of the shell oxide; and wherein after Step 1, Step 2 is completed within a prescribed time during which the core oxide particles do not aggregate in the mixed fluid. It is preferable that the prescribed time is within 1 second.

The present inventions also provide a method of producing core-shell type oxide particles wherein the surface of the core oxide particles are coated with the shell oxide, comprising at least two steps of: Step 1 of precipitating the core oxide particles in a mixed fluid prepared by mixing an oxide raw material liquid for core containing at least an oxide raw material for core which is a raw material of the core oxide particles, and an oxide precipitation solvent containing at least an oxide precipitation substance for precipitating the core oxide particles; and Step 2 of coating the entire surface of the core oxide particles uniformly with the shell oxide by mixing the mixed fluid and an oxide raw material liquid for shell containing at least a shell oxide raw material which is a raw material of the shell oxide; and wherein Step 1 and Step 2 are controlled so that the primary particle diameter of the core-shell type oxide particles is 190% or less relative to the primary particle diameter of the core oxide particles.

Further, the present inventions may be performed wherein at least three fluids of the oxide raw material liquid for core, the oxide precipitation solvent and the oxide raw material liquid for shell are mixed in the space between at least two processing surfaces which are disposed so as to face each other, being capable of approaching to and separating from each other, and rotating relative to each other, to obtain the core-shell type oxide particles.

The present inventions may be also performed wherein the center side of the at least two processing surfaces is disposed at an upstream side and the outside is disposed at a downstream side; either one of the oxide raw material liquid for core and the oxide precipitation solvent as the first fluid passes from the upstream side to the downstream side between the at least two processing surfaces, while forming a thin film fluid; the other of the oxide raw material liquid for core and the oxide precipitation solvent as the second fluid is introduced into the space between the at least two processing surfaces from an opening formed on at least either one of the at least two processing surfaces through the second passage independent from the first passage which the first fluid is introduced into the space between the at least two processing surfaces through, and then the oxide raw material liquid for core and the oxide precipitation solvent are mixed between the at least two processing surfaces to precipitate the core iron oxide particles; the oxide raw material liquid for shell is introduced into the space between the at least two processing surfaces from an opening formed on at least either one of the at least two processing surfaces through the third passage independent from the first passage and the second passage; and the opening of the second passage is provided at the upstream side of the opening of the third passage.

The present inventions may be also performed wherein the following equations are satisfied:

$$F1 > F2 \text{ and } F1 + F2 > F3$$

wherein F1 is a flow rate of the first fluid introduced in the space between the at least two processing surfaces, F2 is a flow rate of the second fluid introduced in the space between the at least two processing surfaces, and F3 is a flow rate of the third fluid introduced in the space between the at least two processing surfaces.

The present inventions may be performed wherein the core oxide particles are zinc oxide particles or iron oxide particles, and the shell oxide is a silicon oxide.

The present inventions may be also performed wherein the core oxide particles are zinc oxide particles, and thickness of the shell oxide is 0.01% to 60% relative to the diameter of the core-shell type oxide particles.

The present inventions may be also performed wherein the core oxide particles are zinc oxide particles, and after irradiating a ultraviolet light of 365 nm for at least 2 hours to a dispersion containing methylene blue dye in which the core-shell type oxide particles are dispersed, an attenuation rate of absorbance derived from methylene blue dye for a light of a wavelength of around 660 nm is 10% or less.

The present inventions may be also performed wherein the core oxide particles are iron oxide particles, and thickness of the shell oxide is 0.5% to 25% relative to the diameter of the core-shell type oxide particles.

The present inventions may be also performed wherein the core oxide particles are iron oxide particles, and after irradiating a white light for at least 2 hours to a dispersion containing Congo red dye in which the core-shell type oxide particles are dispersed, an attenuation rate of absorbance derived from Congo red dye for a light of a wavelength of around 505 nm is 10% or less.

The present inventions may be also performed wherein the shell oxide contains an element different from an element contained in the core oxide particles.

The present invention provides core-shell type oxide particles wherein the entire surface of the core oxide particles is uniformly coated with a shell oxide, wherein the core oxide particle is one single zinc oxide particle, and the shell oxide is a silicon oxide, and thickness of the shell oxide is 0.01% to 60% relative to the diameter of the core-shell type oxide particles.

The present inventions provide core-shell type oxide particles wherein the entire surface of the core oxide particles is uniformly coated with a shell oxide, wherein the core oxide particle is one single iron oxide particle, and the shell oxide is a silicon oxide, and thickness of the shell oxide is 0.5% to 25% relative to the diameter of the core-shell type oxide particles.

Along with the studies on the above mentioned core-shell type oxide particles, the present inventors also have found that silicon oxide-coated iron oxide can be applied to a composition for coating, and have completed the following inventions.

That is, the present inventions provide a silicon oxide-coated iron oxide composition for coating, containing iron oxide particles wherein at least a part of the surface of the iron oxide particles is coated with a silicon oxide, wherein reflectance for a light of a wavelength of 400 to 620 nm is less than 18%, and a primary particle diameter of the iron oxide particles is 1 to 50 nm.

Further, the present inventions may be performed as a dispersion containing the above iron oxide particles. Preferably, transmittance of a dispersion containing the iron oxide particles for a light of a wavelength of 200 to 420 nm is 2.0% or less, and transmittance of the dispersion for a light of a wavelength of 620 to 800 nm is 80% or more.

In addition, it is preferable in the present invention that haze value of a dispersion containing the iron oxide particles is 2.0% or less at the concentration of 2 wt % of the iron oxide in the dispersion.

The present invention may be also performed wherein the silicon oxide is amorphous.

The silicon oxide-coated iron oxide composition for coating of the present invention can exhibit its performance as long as at least a part of the surface of the iron oxide is coated with a silicon oxide. The composition may be in a form other than a core-shell type particle form, but it is preferable to perform as core-shell type oxide particles.

That is, the present inventions provide a novel weather resistant composition for coating which is blended and used in a coating material constituting a coated body, and has prescribed reflectance, transmittance and transparency, and protects the coated body from an ultraviolet light. The weather resistant composition for coating comprises core-shell type iron oxide particles wherein the surface of the core iron oxide particles is coated with a shell silicon oxide. In the core-shell type iron oxide particles, the silicon oxide is preferably amorphous, and a primary particle diameter of the core-shell type iron oxide particles is most preferably 1 to 50 nm.

Regarding the relation between the core and the shell, it is preferable that a primary particle diameter of the core-shell type iron oxide particles is 100.5% or more and 190% or less relative to the primary particle diameter of the core iron oxide particle.

In addition, it is preferable that the core iron oxide particles are $\alpha$-$Fe_2O_3$.

The core-shell type iron oxide particles having the above structure can exhibit the following characteristics.

That is, regarding reflectance, reflectance of the core-shell type iron oxide particles for a light of a wavelength of 400 to 620 nm can be less than 18%.

Regarding transmittance, transmittance of a dispersion prepared by dispersing the core-shell type iron oxide particles in propylene glycol at the concentration of 0.05 wt % of the iron oxide for a light of a wavelength of 200 to 420 nm can be 2.0% or less, and transmittance of the dispersion for a light of a wavelength of 620 to 800 nm can be 80% or more.

Regarding transparency, haze value of a dispersion prepared by dispersing the core-shell type iron oxide particles in propylene glycol or water at the concentration of 2 wt % of the iron oxide can be 2.0% or less.

Advantageous Effects of the Invention

According to the present invention, core-shell type oxide particles having uniform shell thickness can be efficiently and stably produced. In the case where the core-shell type oxide particles are a zinc oxide coated with a silicon oxide or an iron oxide coated with a silicon oxide, they can be used as a raw material for a coating film which suppresses the photocatalytic ability and has light resistance.

The present invention can provide a silicon oxide-coated iron oxide composition for coating which has high transparency and does not impair the characteristics of the coating material.

The present invention further can provide a weather resistant composition for coating which protects the above coated body from an ultraviolet light, and is blended and used in a coating material constituting a coated body, and can be effectively applied to a coated body having various colors, in particular to a red color coated body.

DESCRIPTION OF THE INVENTION

Figure 1:
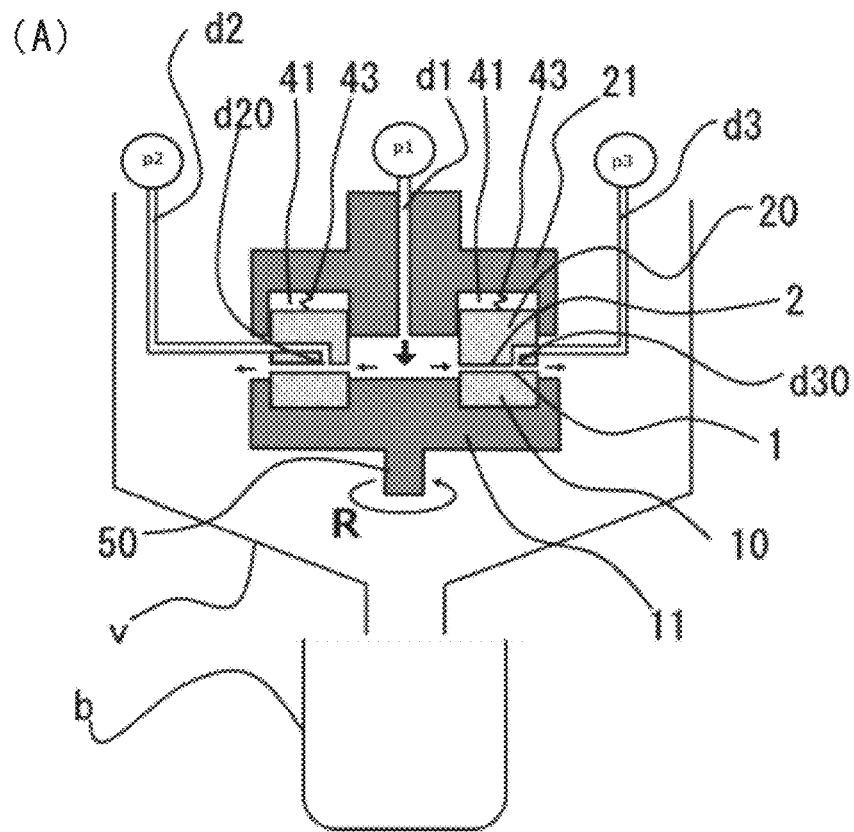
FIG. 1(A) shows an approximate cross sectional view of a fluid processing apparatus according to an embodiment of the present invention.
FIG. 1(B) shows an approximate cross sectional view of a fluid processing apparatus according to another embodiment of the present invention.
Figure 1:
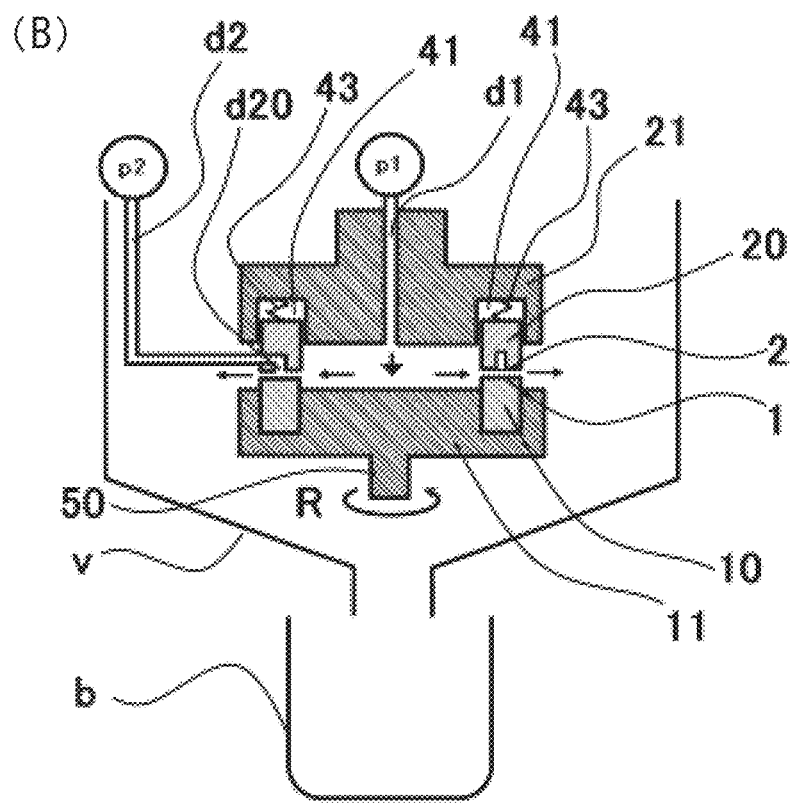

Hereinafter, embodiments of the present invention are explained with reference to the drawings.

(Core-Shell Type Oxide Particles)

In the present invention, core-shell type oxide particles are particles wherein the entire surface of the core oxide particles is uniformly coated with a shell oxide. Here, the core oxide particles and the shell oxide are different substances, but it is preferable that the shell oxide contains an element different from the element contained in the core oxide particles. Here, "an element different from the element contained in the core oxide particles" means that the elements which are contained in the core and the shell as main components, are different between the core and the shell. It is not excluded that the element contained in the core oxide particles is contained in the shell oxide, and that the element contained in the shell oxide is contained in the core oxide particles. "Main component" means that a main component element (excluding oxygen element) contained in the core oxide particles or the shell oxide occupies 50% or more of all elements (excluding oxygen element) contained in the core oxide particles or the shell oxide. The core-shell type oxide particles according to the present invention are preferably core-shell type oxide particles wherein the core oxide particles are zinc oxide particles or iron oxide particles, and the shell oxide is a silicon oxide. When the core-shell type oxide particles are used as a colorant or ultraviolet protective agent, the photocatalytic ability can be suppressed out of the exhibited characteristics (photocatalytic ability and ultraviolet absorbing ability). In view of improvement in dispersibility, transparency and solvent resistance, it is preferable that the shell oxide is a silicon oxide.

(Raw Material of Oxide)

An oxide raw material used in production of core-shell type oxide particles of the present invention is not particularly limited. Any substances can be used as long as the substances become an oxide in a manner such as a reaction, crystallization, precipitation, coprecipitation or the like. In the present invention, hereinafter, the above methods are referred to as precipitation. Here, the oxide raw materials used in production of the core-shell type oxide particles of the present invention are an oxide raw material for core which is a raw material of the core oxide particles and an oxide raw material for shell which is a raw material of the shell oxide. The oxide raw materials include, for example, an elemental metal and an elemental non-metal, and a metal compound and a non-metal compound. A metal in the present invention is not particularly limited, but preferably is all metal elements in the chemical periodic table. An inorganic metal in the present invention is not particular limited, but preferably includes inorganic metal elements such as B, Si, Ge, As, Sb, C, N, O, S, Te, Se, F, Cl, Br, I, At, and the like. Further, these metals or non-metals may be a single element, or may be an alloy composed of a plurality of elements, or a substance containing a metal element and a non-metal element. In the present invention, the above metal compound is referred to as a metal compound. A metal compound or the above non-metal compound is not particularly limited, but preferably includes, for example, a salt, an oxide, a hydroxide, a hydroxide oxide, a nitride, a carbide, a complex, an organic salt, an organic complex, an organic compound of the metal or non-metal, or a hydrate thereof, an organic solvate thereof, and the like. A metal salt or non-metal salt is not particularly limited, but includes a nitrate, a nitrite, a sulfate, a sulfite, a formate, an acetate, a phosphate, a phosphite, a hypophosphite, a chloride, an oxy salt, an acetylacetonate of the metal or non-metal, or a hydrate thereof, an organic solvate thereof and the like. An organic compound includes a metal alkoxide, a non-metal alkoxide, and the like. These metal compounds or non-metal compounds may be used alone, or a mixture of a plurality of these compounds may be used as an oxide raw material.

When the core oxide particles are a zinc oxide or an iron oxide, an oxide raw material for core includes, for example, an oxide and a hydroxide of zinc or iron, and other compounds such as a salt and an alkoxide of zinc or iron, and a hydrate thereof and the like. The raw material of oxide particles is not particularly limited, but includes, an inorganic compound such as a chloride, nitrate or sulfate of zinc or iron and the like, and an organic compound such as an alkoxide or acetylacetonate of zinc or iron and the like, and the like. Specific examples include, for example, zinc oxide, zinc chloride, zinc nitrate, iron(III) chloride, iron(II) chloride, iron(II) nitrate, iron(III) sulfate, zinc acetylacetonate, iron acetylacetonate and a hydrate thereof and the like.

When the shell oxide is a silicon compound, an oxide raw material for shell includes a silicon oxide, a silicon hydroxide, other compounds such as a silicon salt and a silicon alkoxide, and a hydrate thereof. Not particularly limited, it includes phenyltrimethoxysilane, methyltrimethoxysilane, methyltriethoxysilane, 3-glycidoxypropyltrimethoxysilane, 3-trifluoropropyl-trimethoxysilane, methacryloxypropyltriethoxysilane, tetramethoxysilane (TMOS), tetraethoxysilane (TEOS), and an oligomeric condensate of TEOS, for example, ethyl silicate 40, tetraisopropylsilane, tetrapropoxysilane, tetraisobutoxysilane, tetrabutoxysilane, and a similar material thereof. Further as an oxide raw material for shell, another siloxane compound, bis(triethoxysilyl)methane, 1,9-bis(triethoxysilyl)nonane, diethoxydichlorosilane, triethoxychlorosilane and the like may be used.

Further, in the present invention, an oxide raw material liquid for core containing at least an oxide raw material for a core is used, and an oxide raw material liquid for shell containing at least an oxide raw material for shell is used. When the above oxide raw material is a solid, it is preferable to use the above oxide raw material in a molten state, or in a state of being mixed or dissolved in a solvent described below, including a molecular dispersion state. Even when the above oxide raw material is a liquid or gas, it may be used in a state of being mixed or dissolved in a solvent described below, including a molecular dispersion state. Regarding the oxide raw material for core and oxide raw material for shell, in case of using a single oxide raw material respectively, an oxide containing a single element as an element other than oxygen may be produced, so that core-shell type oxide particles containing a single element as an element other than oxygen respectively in the core or shell can be produced. Further, regarding the oxide raw material for core and oxide raw material for shell, in case of using a plurality of oxide raw materials respectively, a composite oxide containing a plurality of elements as an element other than oxygen may be produced, so that core-shell type oxide particles containing a plurality of elements as an element other than oxygen respectively in the core or shell can be produced. Further, the invention can be performed when the above oxide raw material liquid for core and oxide raw material liquid for shell include those in a state of the condition such as dispersion or slurry.

An oxide precipitation substance in the present invention is not particularly limited as long as the substance can make an oxide raw material for core contained in an oxide raw material liquid for core be precipitated as core oxide particles, and can make an oxide raw material for shell contained in an oxide raw material liquid for shell be precipitated as a shell oxide. For example, an acidic substance or a basic substance may be used.

(Basic Material)

A basic substance in the present invention includes a metal hydroxide such as sodium hydroxide and potassium hydroxide, a metal alkoxide such as sodium methoxide and sodium isopropoxide, an amine compound such as triethylamine, diethylaminoethanol and diethylamine, ammonia and the like.

(Acidic Substance)

An acidic substance in the present invention includes an inorganic acid such as aqua regia, hydrochloric acid, nitric acid, fuming nitric acid, sulfuric acid, fuming sulfuric acid, and an organic acid such as formic acid, acetic acid, chloroacetic acid, dichloroacetic acid, oxalic acid, trifluoroacetic acid, trichloroacetic acid and the like.

(Oxide Precipitation Solvent and Solvent Used for Preparation)

In the present invention, an oxide precipitation solvent containing at least an oxide precipitation substance is used. It is preferable to prepare an oxide precipitation solvent by mixing, dissolving or molecularly dispersing at least an oxide precipitation substance in a solvent. A solvent used in preparation of an oxide raw material liquid for core, an oxide precipitation solvent and an oxide raw material liquid for shell, includes, for example, water, an organic solvent, or a mixed solvent of a plurality of these solvents. The water includes tap water, ion exchange water, pure water, ultrapure water, RO water and the like. The organic solvent includes, an alcohol solvent, an amide solvent, a ketone solvent, an ether solvent, an aromatic compound solvent, carbon disulfide, an aliphatic compound solvent, a nitrile solvent, a sulfoxide solvent, a halogen compound solvent, an ester solvent, an ionic liquid, a carboxylic acid compound, a sulfonic acid compound and the like. Each of the above solvents may be used alone, or a plurality of them may be mixed and used. An alcohol solvent includes a monohydric alcohol such as methanol and ethanol, a polyol such as ethylene glycol and propylene glycol, and the like. Further, if necessary, the above acidic substance may be mixed with an oxide raw material liquid for core or an oxide raw material liquid for shell, as long as it does not adversely affect production of core-shell type oxide particles.

(Preparation Apparatus)

For preparation of the oxide raw material liquid for core, the oxide raw material liquid for shell or the oxide precipitation solvent in the present invention, it is desirable to be prepared by using a preparation apparatus such as a rotary dispersing machine to achieve homogeneous mixing by adding a shearing force or the like to the fluid, for example, a machine to rotate a stirrer of various shapes including rod-like, plate-like and propeller-like shapes in a vessel, a machine equipped with a screen which rotates relative to a stirrer, or the like. As a preferable example of a rotary dispersing machine, the stirring machine disclosed in JP 5147091 can be applied.

Further, the rotary dispersing machine may be a batch type machine or a continuous type machine. When carried out in continuous mode, the continuous type machine may be a machine in which fluids are continuously supplied to and discharged from a stirring tank, or a machine using a continuous mixer without using a stirring tank, or a machine controlling mixing energy appropriately using a known stirrer or stirring means. The stirring energy is explained in detail in JP H04-114725 filed by the present applicant. Stirring methods in the present invention are not particularly limited, and various stirring machines such as a shearing type machine, a friction type machine, a high pressure jet type machine, an ultrasonic machine, and a dissolver, an emulsifier, a dispersing machine, a homogenizer and the like can be used in the present invention. Examples of the rotary dispersing machine include continuous emulsification machines such as Ultra-Turrax (IKA Works, Inc.), Polytron (Kinematica AG), TK Homomixer (Primix Corporation), Ebara Milder (Ebara Corporation), TK Homomic Line Flow (Primix Corporation), Colloid Mill (Shinko-Pantech Co., Ltd.), Thrasher (Nippon Coke & Engineering Co., Ltd.), Trigonal Wet Type Micropulverizer (Mitsui Miike Machinery Co., Ltd.), Cavitron (Eurotech, Ltd.), Fineflow Mill (Pacific Machinery & Engineering Co., Ltd.) and the like; and batch type or dual type emulsification machines such as CLEARMIX (M technique Co., Ltd.), CLEARMIX Dissolver (M technique Co., Ltd.), Filmix (Primix Corporation) and the like. Further, stirring treatment is preferably performed by using a stirring machine equipped with a high-speed rotating stirring blade and with a screen outside of the high-speed rotating stirring blade, which discharges a fluid as a jet flow from the opening of the screen, especially above mentioned CLEARMIX (M Technique Co., Ltd.) and CLEARMIX Dissolver (M Technique Co., Ltd.).

(Dispersing Agent and the Like)

In the present invention, various dispersing agents or surfactants may be used depending on a purpose or necessity, as long as they do not adversely affect production of the core-shell type oxide particles. Not particularly limited, as a dispersing agent or a surfactant, various generally used commercial products or products, and newly synthesized products and the like may be used. As an example, a dispersing agent such as an anionic surfactant, a cationic surfactant, a nonionic surfactant, and various polymers and the like may be used. These may be used alone, or two or more thereof may be used in combination. The surfactant and dispersing agent may be contained in at least one fluid of the oxide raw material liquid for core, oxide precipitation solvent, and oxide raw material liquid for shell. In addition, the surfactant and dispersing agent may be contained in the fourth fluid as described below different from the oxide raw material liquid, oxide precipitation solvent, and oxide raw material liquid for shell.

(Reaction Method: Apparatus)

Figure 4:
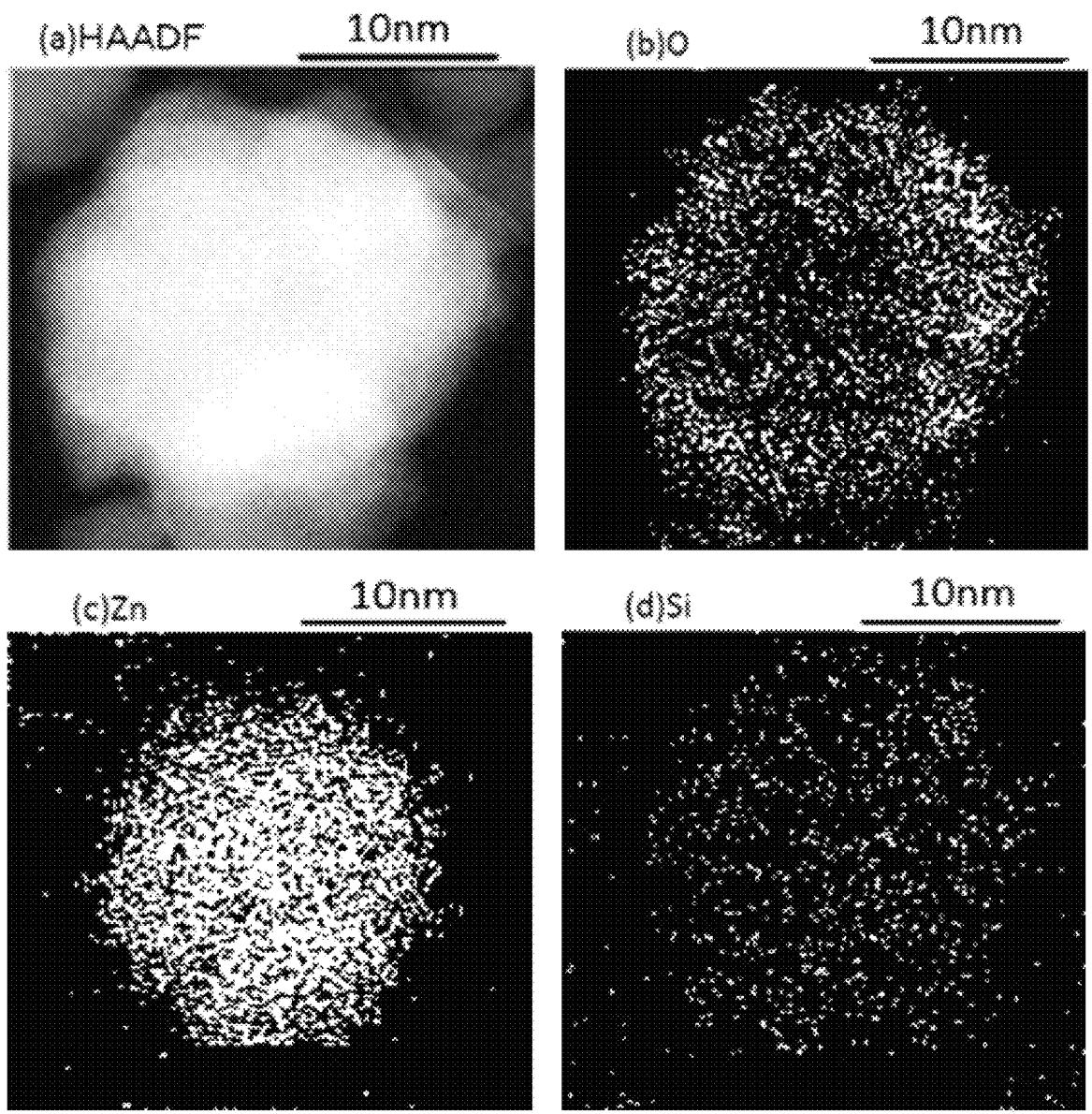
FIG. 4 shows an STEM mapping of the core-shell type oxide particles obtained in Example 1 of the present invention.
Figure 5:
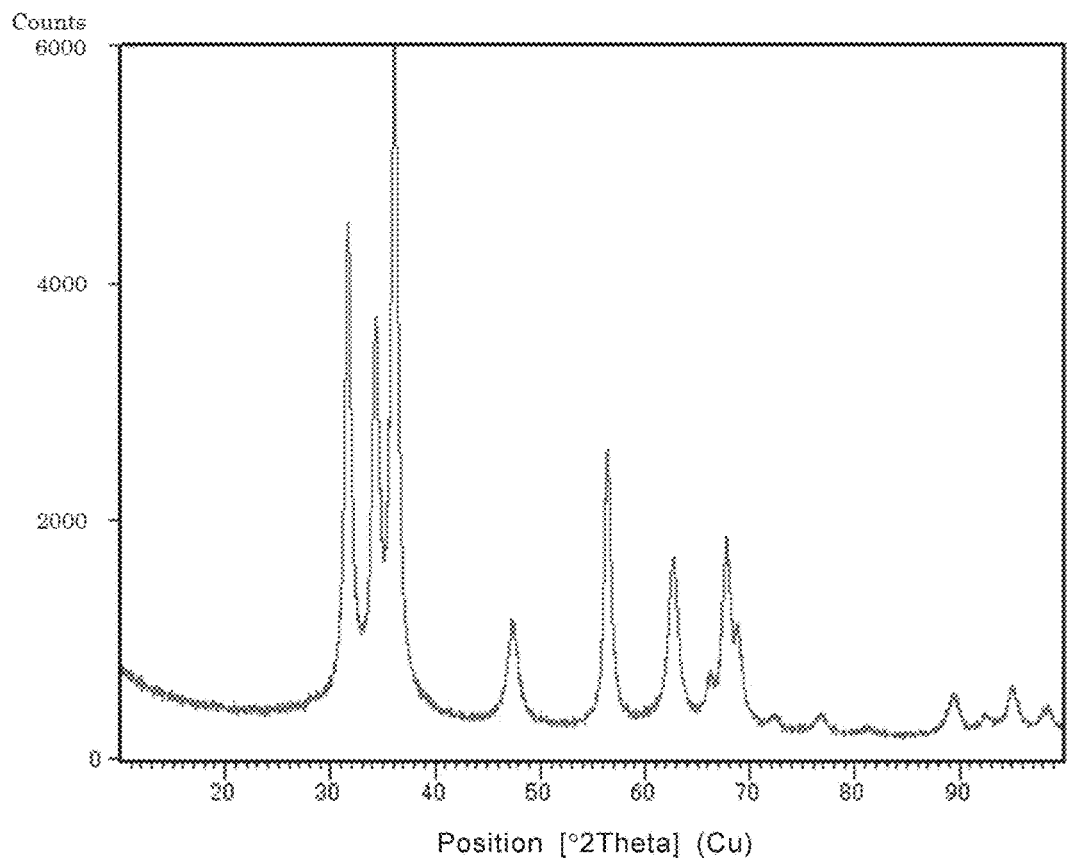
FIG. 5 shows an XRD measurement results of the core-shell type oxide particles obtained in Example 1 of the present invention.

A method of producing core-shell type oxide particles of the present invention or particles wherein at least a part of surface of oxide particles is coated with an oxide includes, for example, a method wherein core oxide particles are produced in the first microreactor, and at least a part of the surface of the core oxide particles is coated with a shell oxide in the subsequent second microreactor; a method wherein the oxide particles are produced in a batch vessel under a dilute system and the like, and subsequently at least a part of the surface of the oxide particles is coated with an oxide under a dilute system, and the like; a method wherein the oxide particles are produced by pulverization such as bead mill, and subsequently at least a part of the surface of the oxide particles is coated with an oxide in a reaction vessel, and the like. The apparatus and method as proposed by the present applicant and described in JP 2009-112892 may be also used. The apparatus described in JP 2009-112892 comprises a stirring tank having an inner peripheral surface which cross-section is circular, and a mixing tool attached to the stirring tank with a slight gap to the inner peripheral surface of the stirring tank, wherein the stirring tank comprises at least two fluid inlets and at least one fluid outlet; from one of the fluid inlets, the first fluid to be processed containing one of the reactants among the fluids to be processed is introduced into the stirring tank; from one fluid inlet other than the above inlet, the second fluid to be processed containing one of reactants different from the above reactant is introduced into the stirring tank through a different flow path; at least one of the stirring tank and the mixing tool rotates at a high speed relative to the other to let the above fluids be in a state of a thin film; and in the above thin film, the reactants contained in the first and second fluids to be processed are reacted. JP 2009-112892 further describes that three or more inlet tubes may be provided as shown in FIGS. 4 and 5 to introduce three or more fluids to be processed into the stirring tank.

In the present invention, mixing of at least the above oxide raw material and oxide precipitation solvent is preferably performed at least using a microreactor. It is especially preferable to use an apparatus similar to the fluid processing apparatus shown in FIG. 1 described in Patent Literature 4. Hereinafter, the microreactor is explained in detail. In FIGS. 1(A) and (B) and FIG. 2, R indicates the rotation direction.

A microreactor (hereinafter, referred to as a fluid processing apparatus) in this embodiment, is equipped with the first and second opposing processing members 10 and 20, and the first processing member 10 rotates. Opposing surfaces of both the processing members 10 and 20 are the processing surfaces. The first processing member 10 possesses the first processing surface 1, and the second processing member 20 possesses the second processing surface 2.

Both processing surfaces 1 and 2 are connected with the flow paths d1, d2 and d3 of the first, second and third fluids to be processed, and constitute a part of the sealed flow paths of the fluids to be processed. The interval between both processing surfaces 1 and 2 is adjusted usually to a small interval of 1 mm or less, for example from 0.1 μm to about 50 μm. Thereby, the fluids to be processed passing between both processing surfaces 1 and 2 are forced by both processing surfaces 1 and 2 to be a forced thin film fluid.

Then, this fluid processing apparatus performs fluid processing for precipitating core-shell type oxide particles by mixing and reacting the first and second or third fluids to be processed between the processing surfaces 1 and 2.

More specifically, the above apparatus is equipped with the first holder 11 for holding the first processing member 10 described above, the second holder 21 for holding the second processing member 20, a surface approaching pressuring mechanism 43, a rotation drive mechanism (not shown in FIG.), the first introduction part d1, the second introduction part d2, the third introduction part d3, and a fluid pressuring mechanisms p1, p2 and p3. As the fluid pressuring mechanisms p1, p2 and p3, a compressor or other pumps may be used. A thermometer and a pressure gauge are provided respectively inside the first introduction part d1, the second introduction part d2 and the third introduction part d3, and the introduction pressures and the introduction temperatures under the pressures of the first, second and third fluids to be processed can be measured.

The opening of the third introduction part d3 on the second processing surface 2 is located outside the opening of the second introduction part d2 from the rotation center of the first processing surface 1. That is, on the second processing surface 2, the opening of the third introduction portion d3 is located at a downstream side from the opening of the second introduction portion d2. A gap is formed between the opening of the third introduction part d3 and the opening of the second introduction part d2 in the inner and outer direction of the diameter of the second processing member 20.

In the above embodiment, the first processing member 10 and the second processing member 20 are ring shaped disks. As a material of the first and second processing members 10 and 20, metal, carbon, ceramic, sintered metal, abrasion resistant steel, sapphire, hardened metal, and hard material treated with lining, coating, plating or the like may be used. In the above embodiment, the first and second opposing processing surfaces 1 and 2 in the first and second processing members 10 and 20 are mirror polished, and the arithmetic mean roughness is 0.01 to 1.0 μm.

In the above embodiment, the second holder 21 is fixed to the apparatus, and the first holder 11 rotates which is attached to a rotating shaft 50 of the rotation drive mechanism similarly fixed to the apparatus, and the first processing member 10 supported on the first holder 11 rotates relative to the second processing member 20. Of course, the second processing member 20 may rotate instead, or both may rotate.

Further, in the present invention, the rotation speed may be, for example, 350 to 5,000 rpm.

In the above embodiment, the second processing member 20 approaches to and separates from the first processing member 10 in the direction of the rotation shaft 50, and the part opposite to the processing surface 2 side of the second processing member 20 is retractably housed in the housing portion 41 provided in the second holder 21. However, on the contrary, the first processing member 10 may approach to and separate from the second processing member 20, or both processing members 10 and 20 may approach to and separate from each other.

The housing portion 41 is a concavity housing the part opposite to the processing surface 2 side of the second processing member 20, and is a groove formed in a ring shape. The housing portion 41 houses the second processing member 20, with sufficient clearance that the part opposite to the processing surface 2 side of the second processing member 20 can appear and disappear.

The surface approaching pressuring mechanism is a mechanism for generating a pushing force in the direction of approximating the first processing surface 1 of the first processing member 10 and the second processing surface 2 of the second processing member 20 (hereinafter, referred to as surface approaching pressure). By a balance between this surface approaching pressure and the force of separating both processing surfaces 1 and 2 by the fluid pressure of the first, second and third fluids to be processed (hereinafter, referred to as separation force), the interval between both processing surfaces 1 and 2 is maintained minute, to generate a thin film fluid with a minute film thickness of nm unit to μm unit. In the above embodiment, the surface approaching pressuring mechanism gives a surface approaching pressure with the spring 43 provided in the second holder 21 by energizing the second processing member 20 toward the first processing member 10.

Further, a pressure of a fluid for back pressure such as air and the like may be applied in addition to the spring 43. The sum of all these pressures is the above surface approaching pressure, and this surface approaching pressure is balanced with the separation force due to the fluid pressure of the first to third fluids to be processed. When introducing and mixing each fluid to be processed at the boiling point thereof or higher in the space between the processing surfaces, it is preferable to set the fluid pressure of each fluid to be processed to be high. Specifically, the fluid pressure of each fluid to be processed exceeds the standard pressure thereof, and the surface approaching pressure balancing with the fluid pressure is also set to be high. Specifically, the pressure of the fluid for back pressure may be set to 0.020 to 0.500 MPaG, preferably 0.050 to 0.400 MPaG, more preferably 0.100 to 0.350 MPaG, and the pressure caused by the spring 43 may be set to 0.007 to 0.030 MPa, preferably 0.010 to 0.020 MPa.

The first fluid to be processed pressurized by the fluid pressuring mechanism p1 is introduced into the space between the processing members 10 and 20 from the first introduction part d1 through the opening d10. In this embodiment, the opening d10 is in the inner peripheral side between the processing surfaces 1 and 2.

On the other hand, the second fluid to be processed pressurized by the fluid pressuring mechanism p2 is introduced into the space between the processing members 10 and 20 from the opening d20 formed on the second processing surface through a passage provided from the second introduction part d2 into the interior of the second processing member 20.

In the opening d20, the first fluid to be processed and the second fluid to be processed are merged and mixed.

At that time, the mixed fluids to be processed become a thin film fluid forced by the processing surfaces 1 and 2 to maintain the above minute interval, and are forced to move outside of the ring shape of both processing surfaces 1 and 2. Since the first processing member 10 rotates, the mixed fluids to be processed do not move linearly from the inside of the ring shape of both processing surfaces 1 and 2 to the outside, but move in a substantially spiral shape from the inside to the outside by the combination vector of the mobile vector in the radial direction and the mobile vector in the circumferential direction acting on the fluid to be processed.

Figure 2:
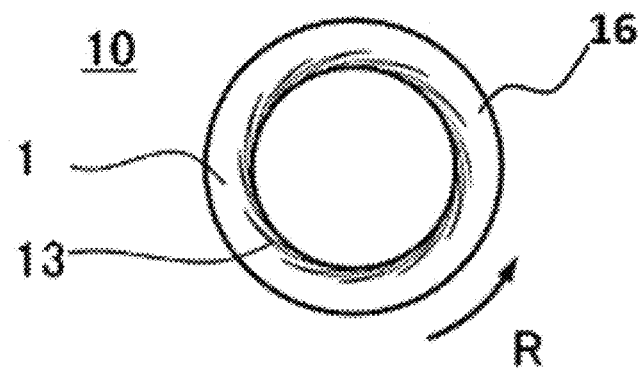
FIG. 2 shows a schematic plan view of the first processing surface of the fluid processing apparatus of FIGS. 1(A) and (B).

Here, as shown in FIG. 2, a groove like concavity 13 may be formed on the first processing surface 1 of the first processing member 10, which extends from the center side to the outside of the first processing member 10, or in the radial direction. The planar shape of the concavity 13 may be one extending curvingly or spirally on the first processing surface 1, and although not shown, one extending straight outward, one bending or curving in an L shape or the like, continuous one, intermittent one, one having branches. Further, the concavity 13 formed on the second processing surface 2 may be performed, and also the concavity 13 formed on both the first and second processing surfaces 1 and 2 may be performed. Formation of such concavity 13 may give a micropump effect, and also an effect to transfer the fluids to be processed between the first and second processing surfaces 1 and 2.

The base end of the concavity 13 desirably reaches the inner periphery of the first processing member 10. The tip end of the concavity 13 extends towards the outer peripheral side of the first processing surface 1, and the depth gradually decreases from the base end to the tip end. A flat surface 16 without concavity 13 is provided between the tip end of the concavity 13 and the outer peripheral surface of the first processing surface 1.

The above opening d20 is preferably provided at a position facing the flat surface of the first processing surface 1. In particular, the opening d20 is preferably provided at a position facing the flat surface 16, which is a downstream side from the position where the flow direction of the first fluids to be processed as introduced by the micropump effect is converted into the flow direction of the spiral laminar flow formed between both processing surfaces. Thereby, it is possible to mix a plurality of fluids to be processed at a laminar flow condition, and to precipitate microparticles.

It is preferred to provide directionality to the second introduction part d2. For example, the introduction direction from the opening d20 of the second processing surface 2 may be inclined at a prescribed elevation angle relative to the second processing surface 2. The introduction direction from the opening d20 of the second processing surface 2 may have directionality on the plane along the above second processing surface 2, and the introduction direction of the second fluid to be processed may be the radially outward direction from the center in the radial direction component, and the forward direction in the rotation direction component of the fluids between the rotating processing surfaces. Thus, the flow of the first fluid to be processed at the opening d20 is a laminar flow, and the second introduction part d2 has directionality, and thereby the second fluid to be processed can be introduced into the space between the processing surfaces 1 and 2 while suppressing occurrence of turbulence against the first fluid to be processed.

Further, as shown in FIG. 1(A), the third fluid to be processed pressurized by the fluid pressuring mechanism p3 is introduced from the opening d30 formed on the second processing surface into the space inside the processing members 10 and 20 through a passage provided from the third introduction part d3 inside the second processing member 20.

Since the opening d30 is provided at the downstream side of the opening d10 and the opening d20, the third fluid to be processed is joined and mixed at the opening d30 with the mixed fluid of the first fluid to be processed and the second fluid to be processed.

As in the case where the first fluid to be processed and the second fluid to be processed are joined and mixed, the mixed fluid to be processed becomes a thin film fluid forced by the processing surfaces 1 and 2 maintaining the above minute interval, and moves in a substantially spiral shape from the inside to the outside of the ring shape of both processing surfaces 1 and 2.

The following points regarding the opening d30 are the same as in the case of the opening d20: the point that the opening d30 is provided preferably at a position facing the flat surface of the first processing surface 1; the point that the opening d30 is provided preferably at a position facing the flat surface 16 at a downstream side from the point where flow direction of the mixed fluid of the first fluid to be processed and the second fluid to be processed is changed to the spiral laminar flow direction formed between the processing surfaces; and further the point that the third introduction part is preferably provided with directionality.

The mixed fluid to be processed discharged outside both processing members 10 and 20 is collected as a discharged liquid in the beaker b through the vessel v. In the embodiment of the present invention, the discharged fluid includes core-shell type oxide particles as described below.

As described above, in the apparatus of this embodiment, the region between the opening d20 and the opening d30 in the region between the processing surfaces 1 and 2 is the precipitation formation region of the core oxide particles in Step 1. The region at the downstream side from the opening d30 (outside in the example of the FIG.) in the region between the processing surfaces 1 and 2 is the precipitation region of the shell oxide in Step 2. However, since Step 1 and Step 2 are performed consecutively, both steps need not be completely separated. In other words, even after Step 2 starts, precipitation and growth of the core oxide particles may partially continue.

Types of the above fluids to be processed and number of the flow paths are three in the example of FIG. 1, but may be four or more. Shape, size and number of the openings for the introduction provided in respective processing members, may be changed and carried out appropriately without any particular restriction. For example, as shown in FIG. 1(B), shape of the opening d20 may be a concentric circular ring shape surrounding the central opening of the processing surface 2 which is a ring shape disc, and the ring shape opening may be continuous or discontinuous. Similarly, shape of the opening d30 may be a concentric circular ring shape surrounding the central opening of the processing surface 2 which is a ring shape disc, and the ring shape opening may be continuous or discontinuous. The introduction opening may be provided just ahead of or at further upstream side of the space between the above first and second processing surfaces 1 and 2. A preferred embodiment of the present application is, as described later, one in which at least the opening d30 for introducing an oxide raw material for shell is continuously opened in a ring disc shape, and the most preferred embodiment is one in which the openings d20 and d30 are continuously opened in a ring disc shape.

By the ring disc shape of the opening d30 or the openings d20 and d30, all of the first to third fluids to be processed can surely be contacted with each other between the processing surfaces 1 and 2. Thereby, it is possible to reliably produce only the core-shell type oxide particles wherein the entire surface of the core oxide particles is uniformly coated with the shell oxide.

The apparatus provided with the above three openings (d10, d20 and d30) is suitable when Step 1 and Step 2 are performed between, the continuous processing surfaces.

However, in practicing the present invention, it is also possible to perform one of Step 1 and Step 2 between the above processing surfaces and to perform the other using a different apparatus. In this case, at least two openings (d10, d20) are enough in the apparatus having the above processing surfaces, but it is not prohibited to use an apparatus having 3 or more openings as shown in FIG. 1(B).

Examples of performing one of Step 1 and Step 2 between the above processing surfaces and performing the other using a different apparatus, include a method of performing Step 1 between the above processing surfaces, followed by continuously performing Step 2 using a batch or continuous mixing reaction apparatus. A specific example is a method wherein an inlet is provided in the vessel v of the above apparatus (not shown in FIG.); an oxide raw material liquid for shell is introduced from the inlet into the vessel v; and the mixed fluid containing the core oxide particles discharged from the processing surfaces 1 and 2 and the oxide raw material liquid for shell is mixed immediately after discharge. The mixed fluid containing the core oxide particles is released from compulsion by the processing surfaces 1 and 2 and is discharged into a wide flow path space. The oxide raw material liquid for shell can be supplied efficiently and continuously to the above mixed fluid discharged while spreading.

In the present invention, for example, the second fluid to be processed may be introduced from the first introduction part d1, and the first fluid to be processed may be introduced from the second introduction part d2, as long as the above mentioned processing can be performed between the processing surfaces 1 and 2. The expressions first to third regarding fluids, only have implications for identification as the fluid is the n th fluid among a plurality of fluids present, and the fourth or later fluids may be present as described above.

In the present invention, it is preferable that three fluids of the oxide raw material liquid for core, the oxide precipitation solvent and the oxide raw material liquid for shell are introduced respectively from the first, second, and third introduction parts (d1, d2, d3) into the space between the processing surfaces 1 and 2 in the fluid processing apparatus. First, the oxide raw material liquid for core (the first fluid to be processed; hereinafter it is also referred to as the first fluid) is introduced from the first introduction part into the space between the processing surfaces 1 and 2, and the oxide precipitation solvent (the second fluid to be processed; hereinafter it is also referred to as the second fluid) is introduced from the second introduction part into the space between the processing surfaces 1 and 2, and both fluids are mixed in the thin film fluid formed between the processing surfaces 1 and 2 to precipitate the core oxide particles in the mixed fluid between the processing surfaces 1 and 2. Next, the oxide raw material liquid for shell (the third fluid to be processed; hereinafter referred to as the third fluid) is introduced from the third introduction part into the space between the processing surfaces 1 and 2, and the mixed fluid containing the precipitated core oxide particles and the oxide raw material liquid for shell are mixed in the thin film fluid formed between the processing surfaces 1 and 2 to precipitate the shell oxide on the surface of the above core oxide particles, and then the core-shell type oxide particles can be prepared. That is, by introducing the oxide raw material liquid for shell into the space between the processing surfaces 1 and 2, after the core oxide particles are precipitated between the processing surfaces 1 and 2 using the fluid processing apparatus, and before the mixed fluid containing the core oxide particles is discharged from the space between the processing surfaces 1 and 2, the mixed fluid containing the core oxide particles and the oxide raw material liquid for shell are mixed between the processing surfaces 1 and 2 to precipitate the shell oxide on the surface of the above core oxide particles, and then the core-shell type oxide particles can be prepared. Since it is enough to mix the first fluid and the second fluid to precipitate the core oxide particles, either one of the oxide raw material liquid for core and the oxide precipitation solvent may be the first fluid, and the other fluid may be the second fluid. By the above method, Step 1 of precipitating the core oxide particles in the mixed fluid prepared by mixing the oxide raw material liquid for core and the oxide precipitation solvent, and Step 2 of coating the entire surface of the core oxide particles uniformly with the shell oxide by mixing the above mixed fluid and the oxide raw material liquid for shell, can be performed continuously. It is necessary to complete mixing the mixed fluid containing the core oxide particles and the oxide raw material for shell and uniformly coating the entire surface of the core oxide particles with the shell oxide, before aggregation of the core oxide particles formed by mixing the first and second fluids. That is, it is necessary to complete Step 2 after Step 1 and before the core oxide particles aggregate in the mixed fluid. It is preferable that the time from mixing of the first and second fluids until precipitation of the core oxide particles and subsequent completion of coating with the shell oxide caused by mixing with the third fluid, is set to 1 second or less. Therefore, it is preferable that the third fluid is mixed subsequently after mixing of the first and second fluids. Not particularly limited, the third fluid is mixed preferably within 1 second after mixing the first and second fluids, more preferably within 0.5 seconds. Thereby, the oxide raw material for shell contained in the third fluid can act on the core oxide particles, before aggregation of the core oxide particles precipitated by mixing the first and second fluids. In the prior art, since core oxide particles aggregate after precipitation, and oxide raw material for shell acts on the aggregated particles, for example, two or more core oxide particles are coated with the shell oxide, so that the primary particle diameter of the produced core-shell type oxide particles sometimes becomes larger than 190% of the primary particle diameter of the core oxide particles. In the method of the present invention, since the entire surface of each one single core oxide particle can be uniformly coated with the shell oxide, the primary particle diameter of the produced core-shell type oxide particles is 190% or less of the primary particle diameter of the core oxide particles. Further, when the coating of the shell oxide is too thin, there is a possibility that various effects possessed by the produced core-shell type oxide particles may not be exhibited. Therefore, it is preferable that the primary particle diameter of the produced core-shell type oxide particles is 100.5% or more of the primary particle diameter of the core oxide particles.

In the present invention, it is preferable that the following equations are satisfied: F1>F2 and F1+F2>F3, wherein F1 is a flow rate of the above first fluid introduced in the space between the processing surfaces 1 and 2, F2 is a flow rate of the above second fluid introduced in the space between the processing surfaces 1 and 2, and F3 is a flow rate of the above third fluid introduced in the space between the processing surfaces 1 and 2. It is important that between the processing surfaces 1 and 2 capable of approaching to and separating from each other, the second fluid is introduced from the second introduction part d2 into the first fluid introduced from the first introduction part d1 provided in the center of the processing member to precipitate the core oxide particles, and the third fluid is introduced from the third introduction part d3 into the mixed fluid formed by mixing the first and second fluids. By satisfying the equation of F1>F2, the second fluid reliably mixes with the first fluid, so that by-products caused by mixing of the unreacted second fluid and the third fluid can be reduced. By satisfying the equation of F1+F2>F3, individual precipitation of the unreacted oxide raw material for shell itself or the shell oxide itself can be reduced, so that precipitation of the shell oxide on the surface of the core oxide particles is ensured. That is, inhibitory factors against precipitation of the shell oxide on the surface of the core oxide particles is reduced, and precipitation of the shell is reliably performed, so that shell can be uniformly formed over the entire core surface. In this way, uniform core-shell type oxide particles can be produced by satisfying the equations of F1>F2 and F1+F2>F3. F2 is normally 99 parts to 1 part, preferably 75 parts to 3 parts relative to 100 parts of F1. Also, F3 is 99 parts to 1 part, preferably 75 parts to 3 parts relative to 100 parts of F1+F2. Furthermore, with regard to the combination of the first, second and third fluids and the processing conditions, it is necessary to complete mixing with the third fluid and uniformly coating the entire surface of the core oxide with the shell oxide within 1 second after mixing the first and second fluids and precipitation of the core oxide. For example, it is considered that in the case that the shell formation is too late, the core oxide particles aggregate and then the aggregates are coated with the shell oxide. It is also considered that in the case that precipitation of the core oxide particles is too late after mixing the first and second fluids, the core oxide particles have not been formed when the third fluid is mixed, so that the core oxide particles and the shell oxide are not in the coated form, but in a state like a composite oxide.

As described above, the core-shell type oxide particles of the present invention are particles wherein the entire surface of the core oxide particles is uniformly coated with a shell oxide. Here, "uniformly coated" means that the thickness of the shell oxide is in the range of 0.01% to 60% of the diameter of the core-shell type oxide particles, that is, the maximum distance between two points on the outer periphery of the core-shell type oxide particles. The thickness of the shell oxide is preferably in the range of 0.1% to 50%, more preferably in the range of 0.2% to 40%.

The core-shell type oxide particles of the present invention can suppress specific characteristics expressed by oxide particles. In the case where the core oxide particles are zinc oxide particles or iron oxide particles and the shell oxide is a silicon oxide, photocatalytic ability can be suppressed. Inhibitory effect of photocatalytic activity was confirmed by measuring ultraviolet-visible light absorption spectrum. More specifically, a dispersion containing a dye wherein the core-shell type oxide particles of the present invention are dispersed therein is irradiated with a light such as an ultraviolet light or visible light for a certain period of time, and an ultraviolet-visible light absorption spectrum before and after the irradiation is measured. Photocatalytic activity was evaluated by the attenuation rate of absorbance (Formula 1) for a specific wavelength derived from the absorption peak of the dye contained in the dispersion.

$$\text{Attenuation rate of absorbance} = (A1 - A2)/A1 \times 100(\%) \quad \text{(Formula 1)}$$

A1: absorbance before irradiation with a light

A2: absorbance after irradiation with a light

Suppression of photocatalytic ability was recognized when the attenuation rate of absorbance was 10% or less. In the case that the attenuation rate of absorbance is 10% or less, it is preferable from the viewpoint that light resistance can be maintained when the core-shell type oxide particles of the present invention are used as a colorant or ultraviolet protective agent. The attenuation rate of absorbance is more preferably 7.5% or less, further preferably 5.0% or less.

The ultraviolet light or the white light in the present invention may be used for evaluating whether the particles of the present invention can suppress photocatalytic activity by a light included in sunlight in the natural world or a light such as a fluorescent lamp and the like in rooms. An ultraviolet light is a light of the wavelength range of 400 to 10 nm. The photocatalytic ability in the present invention may be evaluated using a device capable of outputting an ultraviolet light or the like. Further, it may be evaluated using a device outputting a single wavelength ultraviolet light. A white light in the present invention is a light mixed with visible light in the wavelength range of 400 nm to 750 or 800 nm. The photocatalytic ability in the present invention may be evaluated using a device capable of outputting a white light. Further, it may be evaluated using a device capable of outputting a monochromatic visible light. The above ultraviolet light and white light may be independently used to evaluate photocatalytic ability of the core-shell type oxide particles produced by the production method of the present invention, or both of them may be irradiated at the same time to evaluate photocatalytic ability.

The dye in the present invention is not particularly limited as long as it is decomposed by photocatalytic effect of particles having photocatalytic ability. When the dye is mixed with the dispersion of the core-shell type oxide particles of the present invention, and the obtained dispersion is irradiated with an ultraviolet light or white light for a prescribed time, in the case that decomposition of the dye is confirmed, it indicates that photocatalytic activity of the particles is acknowledged. In the case that not confirmed, it indicates that no photocatalytic ability is acknowledged. In the present invention, decomposition of the dye was confirmed by the attenuation rate of absorbance described above.

(pH Range)

In the present invention, pH of the oxide raw material liquid for core, oxide precipitation solvent and oxide raw material liquid for shell is not particularly limited. The pH may be appropriately changed depending on the type and concentration of the used oxide raw material (oxide raw material for core, oxide raw material for shell) and oxide precipitation substance, and the type of the objective or targeted core-shell type oxide particles, and the like.

For example, when the core oxide particles are zinc oxide particles, pH of the mixed fluid after completion of Step 2 preferably exceeds 12. When pH of the mixed fluid after completion of Step 2 is 12 or less, it is not preferable because by-products other than zinc oxide (for example, $6Zn(OH)_2 \cdot ZnSO_4 \cdot 4H_2O$) are formed in addition to zinc oxide.

In the case that the shell oxide is a silicon compound, acidity or alkalinity of the reaction field is preferably basic, when an oxide raw material for shell is reacted to form a shell oxide, and to coat the entire surface of the core oxide with a shell oxide. In Step 2, the oxide raw material for shell can be reacted by a sol-gel method under a basic condition, to prepare the core-shell type oxide particles wherein the entire surface of the core oxide particles is coated with the shell oxide. More specifically, when preparing the core-shell type oxide particles wherein the entire surface of the core oxide particles is coated with a shell oxide, uniformity of the shell can be improved, by hydrolyzing the oxide raw material for shell under an acidic or basic condition, followed by dehydration and polycondensation under a basic condition.

(Temperature)

In the present invention, temperature at the time of mixing the oxide raw material liquid for core and the oxide precipitation solvent is not particularly limited. Temperature at the time of mixing the mixed fluid obtained by mixing the oxide raw material liquid for core and the oxide precipitation solvent and the oxide raw material liquid for shell are mixed, is not particularly limited. Temperature may be appropriately selected for execution depending on the type of the used oxide raw material and oxide precipitation substance, the type of the objective core-shell type oxide particles, and pH of respective fluids and the like.

Next, the silicon oxide coated iron oxide wherein the core oxide is iron oxide particles and the shell oxide is a silicon oxide, is explained in detail. Hereinafter, a composition containing a silicon oxide-coated iron oxide is also referred to as a silicon oxide-coated iron oxide composition for coating. The above silicon oxide-coated iron oxide suitably exerts its performance by using it for a composition for coating, particularly a coating material for a multilayer coating film. The same reference numbers are given to the same members, and a detailed description thereof is omitted.

A silicon oxide-coated iron oxide composition for coating of the present invention, is a composition containing a silicon oxide-coated iron oxide such as powers of a silicon oxide-coated iron oxide; a dispersion wherein a silicon oxide-coated iron oxide is dispersed in a liquid dispersion medium; and a dispersion wherein a silicon oxide-coated iron oxide is dispersed in a solid such as glass and resin, and the like. A silicon oxide-coated iron oxide composition of the present invention may be used alone, or dispersed in a coating material together with pigments or dyes, or may be overcoated on a coating film. Further, a silicon oxide-coated iron oxide composition of the present invention may be used as a sole pigment. A liquid dispersion medium includes water such as tap water, distilled water, RO water, pure water and ultrapure water; an alcohol solvent such as methanol, ethanol and isopropyl alcohol; a polyhydric alcohol solvent such as propylene glycol, ethylene glycol, diethylene glycol and glycerine; an ester solvent such as ethyl acetate and butyl acetate; an aromatic solvent such as benzene, toluene and xylene; a ketone solvent such as acetone and methyl ethyl ketone; a nitrile solvent such as acetonitrile, and the like. These dispersion media may be used alone, or may be used by mixing a plurality of these dispersion media.

Figure 20:
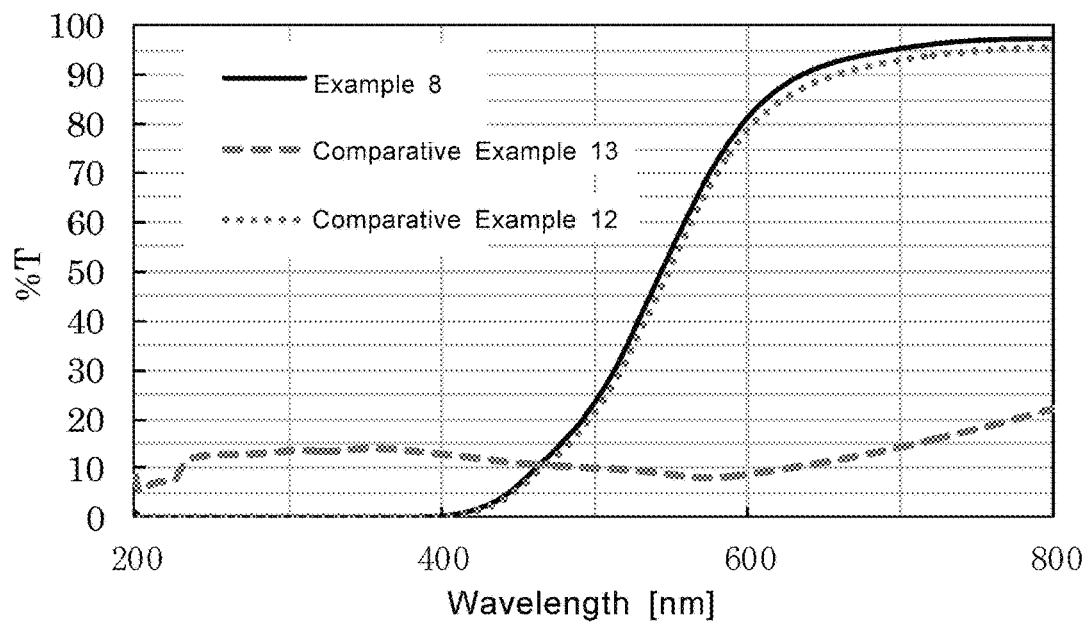
FIG. 20 shows a transmission spectrum of a propylene glycol dispersion of the silicon oxide-coated iron oxide particles obtained in Example 8 of the present invention, and of the iron oxide particles of Comparative Examples 12 and 13.

The transmission spectrum of a silicon oxide-coated iron oxide dispersion of the present invention, specifically a dispersion wherein the silicon oxide-coated iron oxide particles obtained in Example 8 described later were dispersed in propylene glycol at a $Fe_2O_3$ concentration of 0.05 wt %, for a wavelength of 200 to 800 nm, is shown in FIG. 20. As shown in FIG. 20, the transmittance for a light of a wavelength of 620 to 800 nm is 80% or more, and the transmittance for a light of a wavelength of 200 to 420 nm is 2.0% or less.

Figure 22:
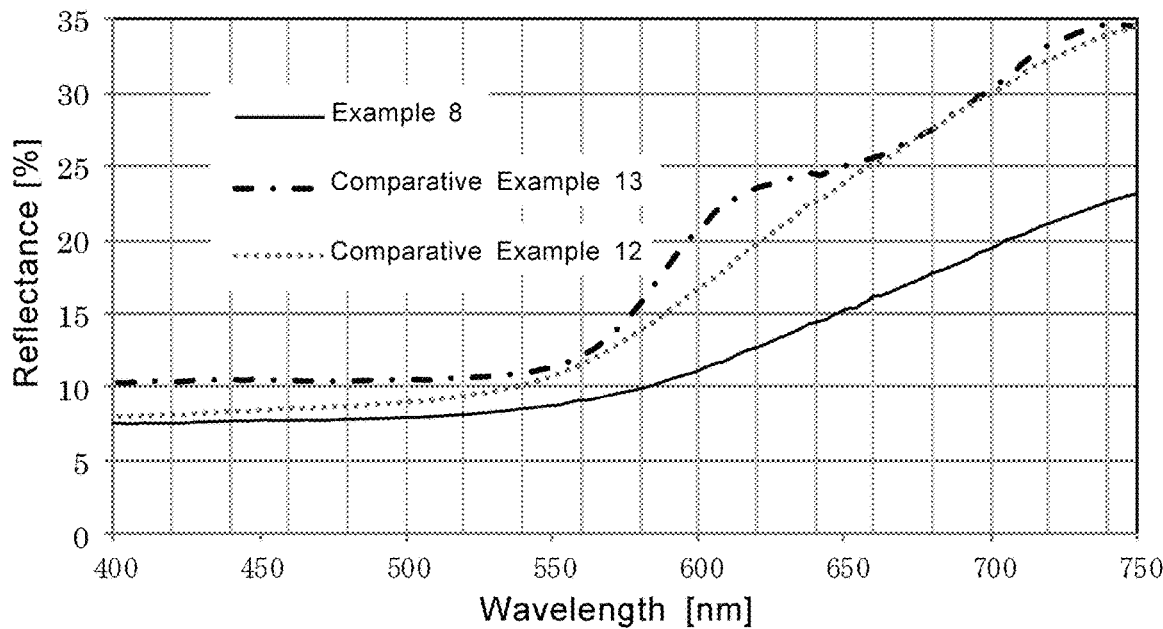
FIG. 22 shows a reflection spectrum of powders of the silicon oxide-coated iron oxide particles obtained in Example 8 of the present invention, and of the iron oxide particles obtained in Comparative Examples 12 and 13.
Figure 23:
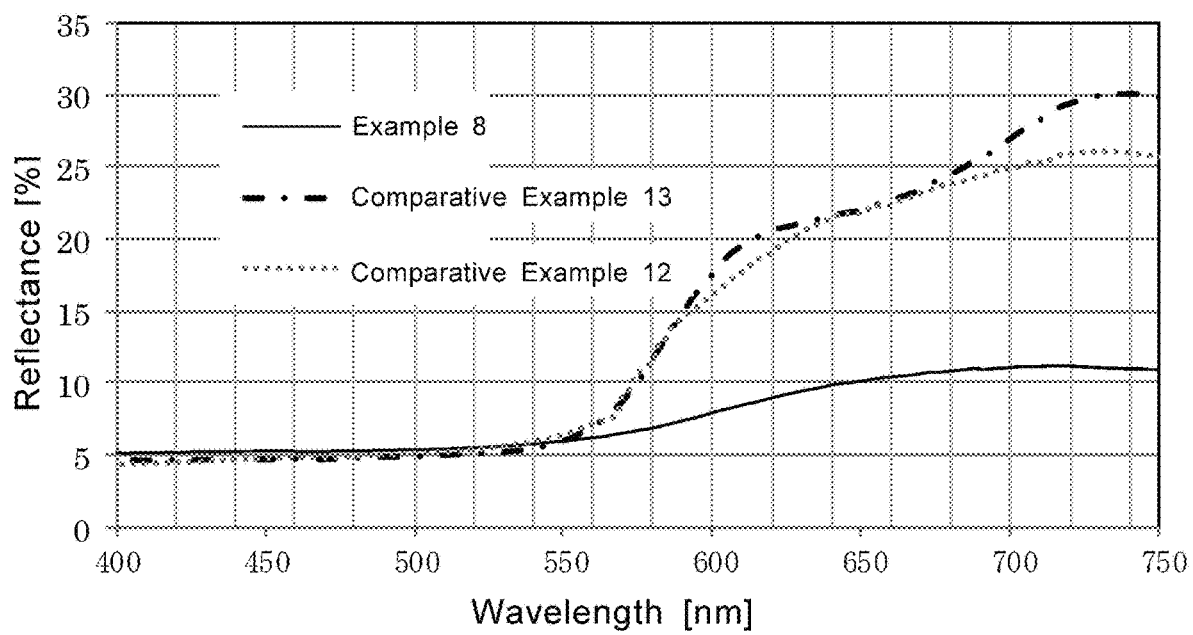
FIG. 23 shows a reflection spectrum of water dispersions of the silicon oxide-coated iron oxide particles obtained in Example 8 of the present invention, and of the iron oxide particles obtained in Comparative Examples 12 and 13.

FIG. 22 shows the reflection spectrum of powders of a silicon oxide-coated iron oxide of the present invention, specifically powders of the silicon oxide-coated iron oxide particles obtained in Example 8. As shown in FIG. 22, the reflectance for a light in the wavelength range of 400 to 620 nm is less than 18%. FIG. 23 shows the reflection spectrum of a water dispersion of a silicon oxide-coated iron oxide of the present invention, specifically a dispersion wherein the silicon oxide-coated iron oxide particles obtained in Example 8 were dispersed in water at a $Fe_2O_3$ concentration of 0.31 wt %, for a wavelength of 400 to 750 nm. As shown in FIG. 23, the reflectance for a light in the wavelength range of 400 to 620 nm is less than 18%. When the reflectance for a light exceeds 18%, the color characteristic emitted by a red coating material is impaired. Therefore, in the present invention, the reflectance for a light in the wavelength range of 400 to 620 nm is preferably less than 18%, more preferably less than 15%.

The haze value of a dispersion prepared by dispersing the silicon oxide-coated iron oxide particles obtained in above Example 8 in propylene glycol at a $Fe_2O_3$ concentration of 0.05 wt % was 0.00%, and the haze value of a dispersion prepared by dispersing the particles in water at a $Fe_2O_3$ concentration of 0.31 wt % was 0.08%. Accordingly both dispersions were highly transparent dispersions. Haze value is a numerical value indicating transparency. When a composition having a haze value exceeding 2% is applied, for example, on a coating material for a building or car, color of the coating material as a foundation is impaired, and thus the intended coloration is inhibited. Also when an ultraviolet protective agent composition having a haze value exceeding 2% and a low transmittance is applied to human skin or the like, the texture and appearance are impaired, which is not preferable. In the present invention, the haze value of a dispersion of the silicon oxide-coated oxide particles at a $Fe_2O_3$ concentration of 2 wt % is preferably 2% or less, more preferably 1.5% or less.

Such a silicon oxide-coated iron oxide dispersion absorbs a light in the ultraviolet region, reflects a light in the near-infrared region, and further transmits a light in the visible region. Therefore, when used for the purpose of mixing in a coating material or for the purpose of protecting a clear layer in a coating, a silicon oxide-coated iron oxide composition for coating can protect and shield from an ultraviolet light without impairing vivid coloring and designability of a colorant.

Figure 13:
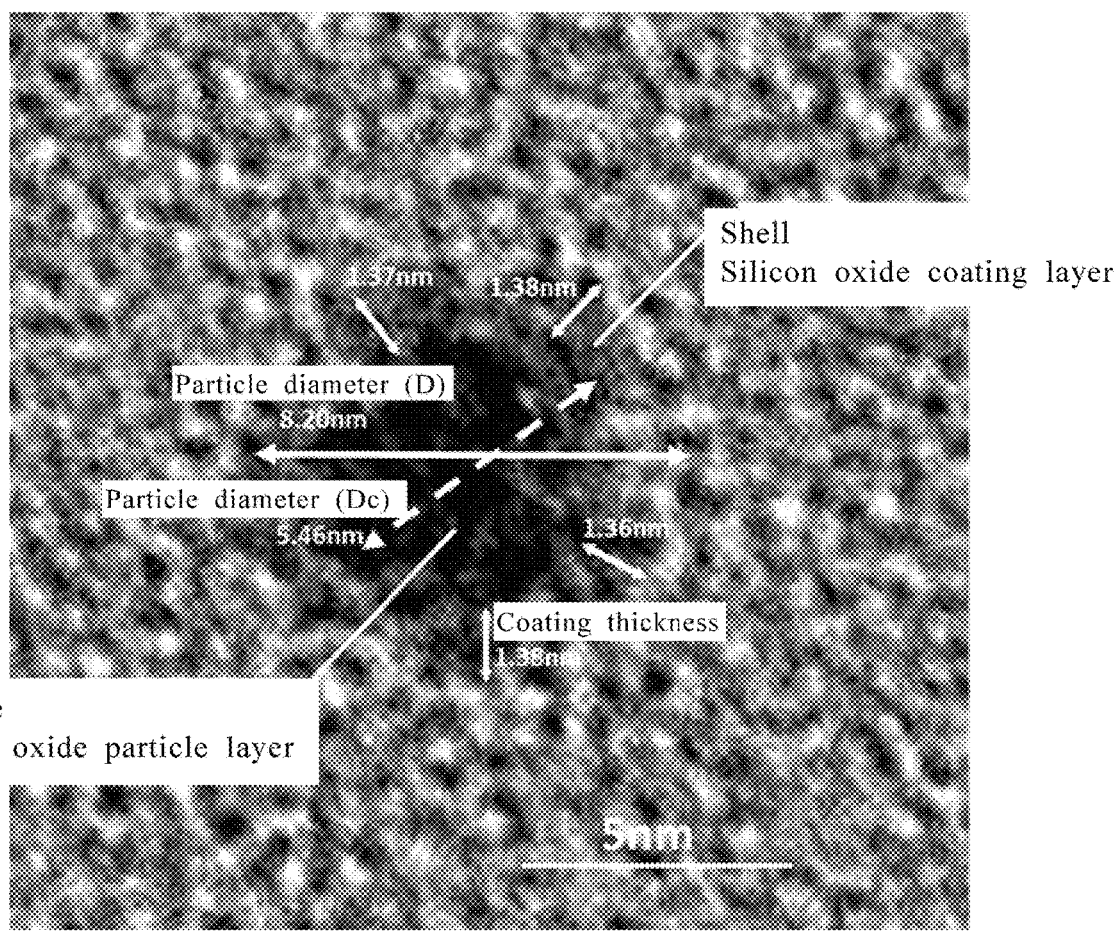
FIG. 13 shows a TEM photograph of the core-shell type oxide particles obtained in Example 8 of the present invention.
Figure 14:
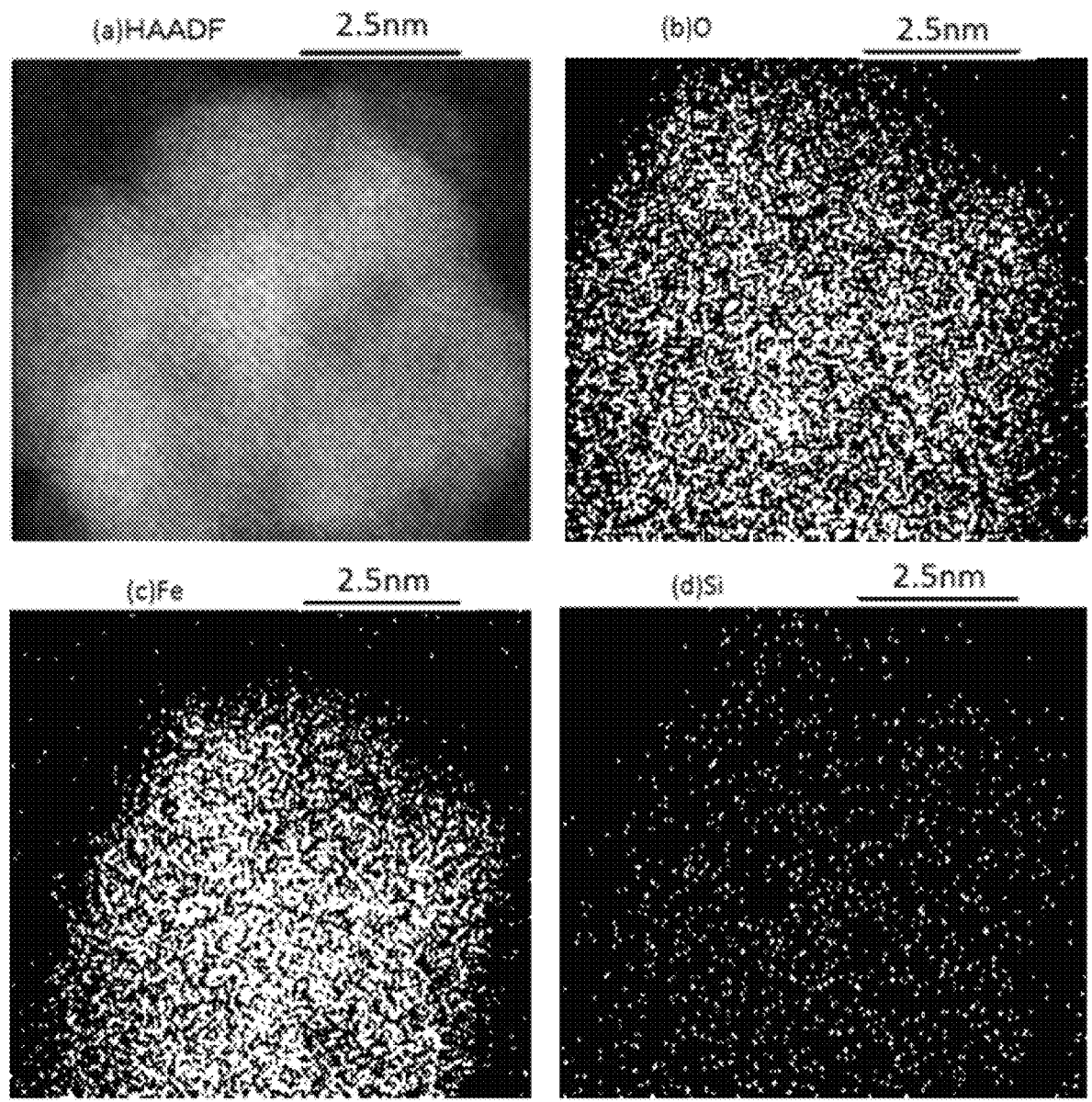
FIG. 14 shows an STEM mapping of the core-shell type oxide particles obtained in Example 8 of the present invention.

The silicon oxide-coated iron oxide of the present invention is an iron oxide whose surface is coated with silicon oxide. FIG. 13 shows a TEM photograph of the silicon oxide-coated iron oxide particles obtained in Example 8 as described below, as an example. FIG. 14 shows an STEM mapping result of the particles. As shown in FIG. 13, silicon oxide-coated iron oxide particles wherein the core is one single iron oxide particle, the shell is a silicon oxide, and the entire surface of the core is uniformly coated with the shell, are observed, and a coating layer (shell layer) of silicon oxide having a thickness of about 1.37 nm on the entire surface of the core iron oxide particle is observed. In FIG. 14, (a) shows a mapping of a dark-field image (HAADF image), (b) shows a mapping of oxygen (O), (c) shows a mapping of iron (Fe), and (d) shows a mapping of silicon (Si). Distribution of oxygens (O) and silicons (Si) was observed in the entire particles observed in the HAADF image, and distribution of iron (Fe) was observed in about 1.37 nm smaller area in radius compared with the particles observed in the HAADF image. Particularly, since an iron oxide has photocatalytic ability, in a state of an iron oxide not coated with a silicon oxide, the iron oxide absorbs an ultraviolet light and exhibits photocatalytic activity, whereby various kinds of ingredients contained in a coating material or a coating film such as a colorant, resin, dispersing agent and the like may be decomposed. Therefore, a silicon oxide-coated iron oxide wherein the surface of the iron oxide is coated with a silicon oxide, is used in the present invention. The present invention can be performed by not only coating the entire coat particles, but also coating at least a part of the core particles. Furthermore, when the surface of the iron oxide is coated with a crystalline silicon oxide, the reflectance for a light of a wavelength of 400 to 620 nm may be increased due to influence on the refractive index and the like. In the present invention, by coating the surface of the iron oxide with an amorphous silicon oxide, the reflectance for a light in the wavelength range of 400 to 620 nm can be reduced to less than 18%, and the reflection of lights other than a red light can be reduced. Therefore, the performance can be improved when used for a red coating material, and further the transmission spectral characteristics and transparency of the above dispersion can be achieved, which are preferable. The amorphous silicon oxide may be in a state of $SiO_2$ or may be in a state wherein a part of oxygen is deficient like $SiO_{2-X}$.

Figure 21:
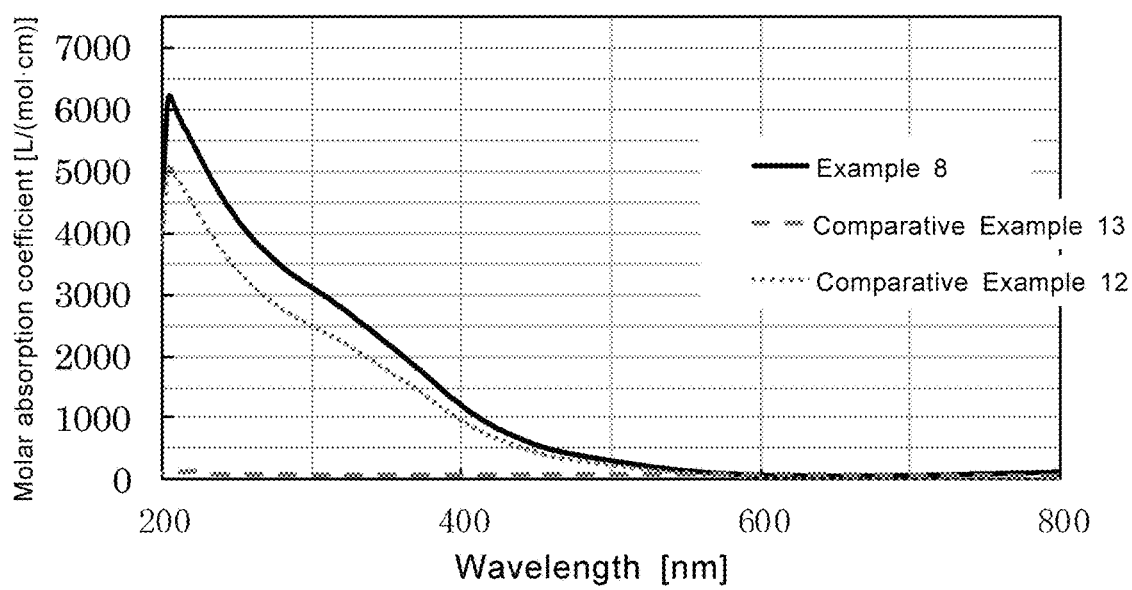
FIG. 21 shows a graph of molar absorption coefficients for measurement wavelengths calculated from the absorption spectrum of a propylene glycol dispersion of the silicon oxide-coated iron oxide particles obtained in Example 8 of the present invention, and of the iron oxide particles of Comparative Examples 12 and 13.

In the present invention, it is considered as a factor leading to completion of the present invention that a molar absorption coefficient of the silicon oxide-coated iron oxide particles for a light of a wavelength of 200 to 420 nm is higher than that of the conventional one. A graph of molar absorption coefficients for measurement wavelengths calculated from the absorption spectrum of a propylene glycol dispersion of the silicon oxide-coated iron oxide particles obtained in Example 8 described later is shown in FIG. 21. In the present invention, a molar absorption coefficient of the above iron oxide particles for a light of a wavelength of 400 nm is preferably 500 L/(mol·cm) or more, and a molar absorption coefficient for a light of a wavelength of 220 nm is preferably 3,000 L/(mol·cm) or more. A molar absorption coefficient can be calculated from the absorbance and the molar concentration in ultraviolet-visible absorption spectrum measurement, by Formula 2 below.

$$\varepsilon = A/(c \cdot l) \qquad \text{(Formula 2)}$$

In Formula 2, ε is a constant inherent to the substance, and is referred to as a molar absorption coefficient. Since ε means the reciprocal of the ratio of light strength after a light passes in a solution at 1 mol/L with a thickness of 1 cm, the unit is L/(mol·cm). A is an absorbance in ultraviolet-visible absorption spectrum measurement. c is a molar concentration of a sample (mol/L). l is a length through which a light is transmitted (optical path length), typically a thickness of a cell in measuring the ultraviolet-visible absorption spectrum.

The primary particle diameter of silicon oxide-coated iron oxide used in the silicon oxide-coated iron oxide composition for coating of the present invention is smaller than that of the generally practical conventional one, and their molar absorption coefficient is higher than that of the conventional one. The molar absorption coefficient is an ability of absorbing a light per unit mol of the iron oxide. A molar absorption coefficient of the silicon oxide-coated iron oxide particle dispersion for a light of a wavelength of 400 nm is 500 L/(mol·cm) or more, and a molar absorption coefficient for a light of a wavelength of 220 nm is 3,000 L/(mol·cm) or more. Thereby, performance as a silicon oxide-coated iron oxide composition for coating can be properly exhibited, and the required large amount can be reduced, and possibility of impairing the haze value and the transmittance can be reduced, when used in a method such as application and the like.

The present inventors consider that factors for the above mentioned high molar absorption coefficient may be not only increase of the surface area due to smaller primary particle diameter than that of the conventional one, but also high crystallinity of the core iron oxide particles in the silicon oxide-coated iron oxide of the present invention. A shape of the particles has smaller effects than the other factors described above, and thus the shape of the particles may be in various shapes. However, a substantially spherical shape is preferable, because the shape enables reduction of birefringence in the coating. Silicon oxide-coated iron oxide particles of the present invention are preferably substantially spherical particles, wherein a long diameter/short diameter ratio is from 1.0 to 3.0, preferably from 1.0 to 2.5, more preferably from 1.0 to 2.0. Silicon oxide-coated iron oxide particles of the present invention are preferably silicon oxide-coated iron oxide particles having a primary particle diameter of 1 to 50 nm, more preferably silicon oxide-coated iron oxide particles having a primary particle diameter of 1 to 20 nm.

In the present invention, iron oxide particles are preferably α-$Fe_2O_3$ (hematite) in the silicon oxide-coated iron oxide wherein the core oxide is iron oxide particles and the shell oxide is a silicon oxide. Therefore, an iron ion contained in an iron oxide raw material for core is preferably $Fe^{3+}$. It is preferable to use a substance that generates $Fe^{3+}$ ion in a solution as an oxide raw material for core. However, an oxide raw material for core may be prepared by dissolving a substance producing $Fe^{2+}$ ion in a solvent, followed by using a means of changing $Fe^{2+}$ ion to $Fe^{3+}$ ion by an oxidizing acid such as nitric acid, and the like. In the present invention, as long as the silicon oxide-coated iron oxide particles constituting the silicon oxide-coated iron oxide composition for coating can exhibit the characteristics of the silicon oxide-coated iron oxide composition for coating of the present invention, a production method is not limited to the above mentioned method of producing core-shell type oxide particles using a microreactor. A method of producing core-shell type oxide particles of the present invention includes, for example, a method wherein core iron oxide particles are produced in the first microreactor, and at least a part of the surface of the core iron oxide particles are coated with a shell silicon oxide in the subsequent second microreactor; a method wherein the iron oxide particles are produced in a batch vessel under a dilute system and the like, and continuously at least a part of the surface of the iron oxide particles are coated with a silicon oxide under a dilute system, and the like; a method wherein the iron oxide particles are produced by pulverization such as bead mill, and subsequently at least a part of the surface of the iron oxide particles are coated with a silicon oxide in a reaction vessel, and the like. The apparatus and method as proposed by the present applicant and described in JP 2009-112892 may be also used.

Not particularly limited, a coating composition in which silicon oxide-coated iron oxide composition for coating of the present invention may be blended, may be applied to those described in Patent Literature 10 or 11, and various coating compositions such as a solvent-based coating material, a water-based coating material. A coating composition may further comprise in addition to various resin components, if necessary, additives such as pigments, dyes, wetting agents, dispersing agents, color separation inhibitors, leveling agents, viscosity modifiers, anti-skinning agents, anti-gelling agents, antifoaming agents, thickeners, anti-sagging agents, antifungal agents, ultraviolet absorbers, film-forming assistant agents, surfactants, if necessary.

A resin component includes polyester resins, melamine resins, phenol resins, epoxy resins, vinyl chloride resins, acrylic resins, urethane resins, silicone resins, fluorine resins and the like.

A coated body which a coating material containing a silicon oxide-coated iron oxide composition for coating of the present invention is applied to, may be a single layer coated body composed of a single coating composition, or a multilayer coated body composed of plurality of coating compositions. A silicon oxide-coated iron oxide composition for coating of the present invention may be performed by adding it to a coating material containing a pigment, or to a coating material such as a clear paint without a pigment.

Color of a coated body includes a red color such as color having a hue from RP to YR in the Munsell hue circle (including a metallic color), but the color is not particularly limited to these colors, and may be a color of any hue. The colors can be suitably mixed in a coating composition used in a coated body.

As a pigment or dye optionally included in a coating composition, various pigments and dyes may be used, and for example, all pigments and dyes registered in the color index may be used. Among these colors, a pigment or dye constituting a red color includes, for example, a pigment or dye classified into C. I. Pigment Red in the Color Index, a pigment or dye classified into C. I. Pigment Violet or C. I. Pigment Orange in the Color Index, and the like. More specific examples include a quinacridone pigment such as C. I. Pigment Red 122 and C. I. Violet 19; a diketopyrrolopyrrole pigment such as C. I. Pigment Red 254 and C. I. Pigment Orange 73; a naphthol pigment such as C. I. Pigment Red 150 and C. I. Pigment Red 170; a perylene pigment such as C. I. Pigment Red 123 and C. I. Pigment Red 179; and an azo pigment such as C. I. Pigment Red 144, and the like. These pigments and dyes may be used alone, or a plurality of these may be mixed and used. Silicon oxide-coated iron oxide particles of the present invention may be also used alone without mixing with the pigments and dyes constituting the above red color and the like.

EXAMPLE

Hereinafter, the present invention is explained in more detail with reference to Examples, but the present invention is not limited only to these examples. In the following examples, liquid A refers to the first fluid to be processed introduced from the first introduction part d1 of the apparatus shown in FIGS. 1(A) and (B), and liquid B similarly refers to the second fluid to be processed introduced from the second introduction part d2 of the apparatus (A) and (B). Liquid C similarly refers to the third fluid to be processed introduced from the third introduction part d3 of the apparatus (A).

Example 1

The oxide raw material liquid for core, the oxide precipitation solvent, and the oxide raw material liquid for shell were prepared using the high-speed rotary dispersion emulsification apparatus CLEARMIX (product name: CLM-2.2 S, M. Technique Co., Ltd.). Specifically, based on the formulation of the oxide raw material liquid for core shown in Example 1 of Table 1, the components of the oxide raw material liquid for core were mixed homogeneously by stirring using CLEARMIX at preparation temperature of 40° C. and at the rotor rotational speed of 20,000 rpm for 30 min to prepare the oxide raw material liquid for core. Based on the formulation of the oxide precipitation solvent shown in Example 1 of Table 1, the components of the oxide precipitation solvent were mixed homogeneously by stirring using CLEARMIX at preparation temperature of 45° C. and at the rotor rotational speed of 15,000 rpm for 30 min to prepare the oxide precipitation solvent. Furthermore, based on the formulation of the oxide raw material liquid for shell shown in Example 1 of Table 1, the components of the oxide raw material liquid for shell were mixed homogeneously by stirring using CLEARMIX at preparation temperature of 20° C. and at the rotor rotational speed of 6,000 rpm for 10 min to prepare the oxide raw material liquid for shell.

Regarding the substances represented by the chemical formula and abbreviations set forth in Table 1, MeOH is methanol (Godo Co., Ltd.), 97 wt % $H_2SO_4$ is concentrated sulfuric acid (Kishida Chemical Co., Ltd.), KOH is potassium hydroxide (Nippon Soda Co., Ltd.), 35 wt % HCl is hydrochloric acid (Kanto Chemical Co., Inc.), TEOS is tetraethyl orthosilicate (Wako Pure Chemical Industry Ltd.), 60 wt % $HNO_3$ is nitric acid (Kanto Chemical Co., Inc.), and ZnO is zinc oxide (Kanto Chemical Co., Inc.).

Then, the prepared oxide raw material liquid for core, the oxide precipitation solvent oxide and the oxide raw material liquid for shell were mixed using the fluid processing apparatus described in FIG. 1(A). Specifically, the oxide precipitation solvent as liquid A was introduced into the space between the processing surfaces 1 and 2, and while driving the processing member 10 at a rotational speed of 1,130 rpm, the oxide raw material liquid for core as liquid B was introduced into the space between the processing surfaces 1 and 2, and the oxide precipitation solvent and the oxide raw material liquid for core were mixed in the thin film fluid, to precipitate the core oxide particles between the processing surfaces 1 and 2. Then, the oxide raw material liquid for shell as liquid C was introduced into the space between the processing surfaces 1 and 2, and liquid C was mixed with a mixed fluid containing the core oxide particles in the thin film fluid. As a result, an oxide for shell was precipitated on the surface of the core oxide particles. The fluid containing the core-shell type oxide particles (hereinafter, the core-shell type oxide particle dispersion) was discharged from the space between the processing surfaces 1 and 2 of the fluid processing apparatus. The core-shell type oxide particle dispersion was collected in the beaker b through the vessel v. The time from introduction of liquid B into the space between the processing surfaces 1 and 2 until discharge of the core-shell type oxide particle dispersion from the space between the processing surfaces 1 and 2 was 0.5 seconds for most of the particles, and was within 1 second.

Table 2 shows the operating conditions of the fluid processing apparatus. The introduction temperatures (liquid sending temperatures) and the introduction pressures (liquid sending pressures) of liquid A, liquid B and liquid C shown in Table 2 were measured using thermometers and pressure gauges provided in sealed inlet paths leading to the space between the processing surfaces 1 and 2 (the first introduction part d1, the second introduction part d2 and the third introduction part d3). The introduction temperature of liquid A shown in Table 2 was the actual temperature of liquid A under the introduction pressure in the first introduction part d1. Similarly, the introduction temperature of liquid B shown in Table 2 was the actual temperature of liquid B under the introduction pressure in the second introduction part d2. The introduction temperature of liquid C shown in Table 2 was the actual temperature of liquid C under the introduction pressure in the third introduction part d3.

For the pH measurement, the pH meter, model number D-51 manufactured by HORIBA Ltd. was used. The pH of liquid A, liquid B and liquid C were measured at room temperature prior to introduction into the fluid processing apparatus. Further, it was difficult to measure the pH of the mixed fluid immediately after mixing the oxide raw material liquid for core and the oxide precipitation solvent, and the pH of the mixed fluid immediately after mixing the mixed fluid containing the core oxide particles and the oxide raw material liquid for shell. Therefore, the core-shell type oxide particle dispersion was discharged from the apparatus and collected in the beaker b, and the pH of the dispersion was measured at room temperature.

Dry powders and wet cake samples were produced from the core-shell type oxide particle dispersion which was discharged from the fluid processing apparatus, and collected in the beaker b. The manufacturing method was conducted according to a conventional method of this type of processing. The discharged core-shell type oxide particle dispersion was collected, and the core-shell type oxide particles were settled, and the supernatant was removed. Thereafter, the core-shell type oxide particles were washed and settled three times repetitively with the mixed solvent of 100 parts by weight of pure water and 100 parts by weight of methanol, and then, were washed and settled three times repetitively with pure water. A part of the finally obtained wet cake of the core-shell type oxide particles was dried at 25° C. for 20 hours to obtain the dry powders. The rest was the wet cake sample.

(Preparation of TEM Observation Sample and Preparation of STEM Observation Sample)

A part of the wet cake samples of the core-shell type oxide particles after the washing process obtained in Examples and Comparative Examples was dispersed in propylene glycol, and further was diluted to 100-fold by isopropyl alcohol (IPA). The resulting diluted liquid was dropped to a collodion membrane or a micro grid, and dried to prepare a TEM observation sample or an STEM observation sample.

(Transmission Electron Microscopy and Energy Dispersive X-Ray Analyzer: TEM-EDS Analysis)

For observation and quantitative analysis of the core-shell type oxide particles by TEM-EDS analysis, the transmission electron microscopy JEM-2100 (JEOL Ltd.) equipped with the energy dispersive X-ray analyzer JED-2300 (JEOL Ltd.) was used. The observation condition was the acceleration voltage of 80 kV, and the observation magnification of 10,000 times or more. The particle diameters (D) described in Tables 2 and 4 were primary particle diameters, and were calculated from the maximum distance between two points on the outer periphery of the core-shell type oxide particles, and the average value of the measured particle diameters of 100 particles was shown. The core particle diameters (Dc) described in Tables 2 and 4 were primary particle diameters, and were calculated from the maximum distance between two points on the outer periphery of the core oxide particles in the core-shell type oxide particles, and the average value of the measured core particle diameters of 100 particles was shown. Also EDS analysis on one particle was performed, and a molar ratio between the elements contained in the core oxide particles and the elements contained in the shell oxide. The thickness of the shell oxide (hereinafter referred to as the thickness of the shell layer) was measured. Four thickness was measured for one particle, and the average value of the measured thickness of 10 particles was described in the item "coating thickness" in Tables 2 and 4. Hereinafter, the core oxide particles are also referred to as a core, and the shell oxide is also referred to as a shell or a shell layer.

(Scanning Transmission Electron Microscopy and Energy Dispersive X-Ray Analyzer: STEM-EDS Analysis)

For the mapping and quantification of elements contained in the core-shell type oxide particles by STEM-EDS analysis, the atomic resolution analytical electron microscopy JEM-ARM200F (JEOL Ltd.) equipped with the energy dispersive X-ray analyzer Centurio (JEOL Ltd.) was used. The observation condition was the acceleration voltage of 80 kV and the observation magnification of 50,000 times or more, and a beam diameter of 0.2 nm was used for analysis.

(X-Ray Diffraction Measurement)

For the X-ray diffraction (XRD) measurement, the powder X-ray diffractometer Empyrean (Spectris Co., Ltd., PANalytical Division) was used. The measurement condition was measurement range of 10 to 100 [° 2Theta], Cu anticathode, tube voltage of 45 kV, tube current of 40 mA, and scanning speed of 0.3°/min. The XRD was measured using the dry powder of the core-shell type oxide particles obtained in Examples and Comparative Examples.

TABLE 1

| | | Formulation of First fluid (Liquid A) | | | | | | | | Formulation of Second fluid (Liquid B) | | |
|---|---|---|---|---|---|---|---|---|---|---|---|---|
| | | Formulation [wt %] | | | | | | pH | | Formulation [wt %] | | |
| | | Raw material | [wt %] | Raw material | [wt %] | Raw material | [wt %] | pH | [° C.] | Raw material | [wt %] | Raw material |
| Example | 1 | Oxide precipitation solvent | MeOH | 93.70 | 97 wt % $H_2SO_4$ | 6.30 | — | — | <1 | — | Oxide raw material liquid for core | ZnO | 3.00 | KOH |
| | 2 | | MeOH | 93.70 | 97 wt % $H_2SO_4$ | 6.30 | — | — | <1 | — | | ZnO | 3.00 | KOH |
| | 3 | | MeOH | 93.70 | 97 wt % $H_2SO_4$ | 6.30 | — | — | <1 | — | | ZnO | 3.00 | KOH |
| | 4 | | MeOH | 93.70 | 97 wt % $H_2SO_4$ | 6.30 | — | — | <1 | — | | ZnO | 3.00 | KOH |
| | 5 | | MeOH | 93.70 | 97 wt % $H_2SO_4$ | 6.30 | — | — | <1 | — | | ZnO | 3.00 | KOH |
| | 6 | | MeOH | 93.50 | 60 wt % $HNO_3$ | 6.50 | — | — | <1 | — | | ZnO | 3.00 | KOH |
| Comparative Example | 1 | Oxide raw material liquid for core | ZnO | 3.00 | KOH | 46.60 | Pure water | 50.40 | >14 | — | Oxide precipitation solvent | MeOH | 93.70 | 97 wt % $H_2SO_4$ |
| | 2-4 | Oxide precipitation solvent | MeOH | 93.50 | 60 wt % $HNO_3$ | 6.50 | — | — | <1 | — | Oxide raw material liquid for core | ZnO | 3.00 | KOH |

| | | Formulation of Second fluid (Liquid B) | | | | Formulation of Third fluid: Oxide raw material liquid for shell (Liquid C) | | | | | | | |
|---|---|---|---|---|---|---|---|---|---|---|---|---|---|
| | | Formulation [wt %] | | pH | | Formulation [wt %] | | | | | | pH | |
| | | [wt %] | Raw material | [wt %] | pH | [° C.] | Raw material | [wt %] | Raw material | [wt %] | Raw material | [wt %] | pH | [° C.] |
| Example | 1 | 46.60 | Pure water | 50.40 | >14 | — | MeOH | 93.69 | 35 wt % HCl | 5.11 | TEOS | 1.20 | <1 | — |
| | 2 | 46.60 | Pure water | 50.40 | >14 | — | MeOH | 94.61 | 35 wt % HCl | 5.11 | TEOS | 0.28 | <1 | — |
| | 3 | 46.60 | Pure water | 50.40 | >14 | — | MeOH | 94.33 | 35 wt % HCl | 5.11 | TEOS | 0.56 | <1 | — |
| | 4 | 46.60 | Pure water | 50.40 | >14 | — | MeOH | 94.33 | 35 wt % HCl | 5.11 | TEOS | 0.56 | <1 | — |
| | 5 | 46.60 | Pure water | 50.40 | >14 | — | MeOH | 94.05 | 35 wt % HCl | 5.11 | TEOS | 0.84 | <1 | — |
| | 6 | 46.60 | Pure water | 50.40 | >14 | — | MeOH | 94.57 | 60 wt % $HNO_3$ | 5.15 | TEOS | 0.28 | <1 | — |
| Comparative Example | 1 | 6.30 | — | — | <1 | — | MeOH | 94.61 | 35 wt % HCl | 5.11 | TEOS | 0.28 | <1 | — |
| | 2-4 | 46.60 | Pure water | 50.40 | >14 | — | MeOH | 94.57 | 60 wt % $HNO_3$ | 5.15 | TEOS | 0.28 | <1 | — |

TABLE 2

| | | Introduction flow rate [ml/min] | | | Introduction temperature (liquid sending temperature) [° C.] | | | Introduction pressure (liquid sending pressure) [MPaG] | | |
|---|---|---|---|---|---|---|---|---|---|---|
| | | Liquid A | Liquid B | Liquid C | Liquid A | Liquid B | Liquid C | Liquid A | Liquid B | Liquid C |
| Example | 1 | 450 | 40 | 95 | 28 | 22 | 25 | 0.050 | 0.10 | 0.10 |
| | 2 | 460 | 40 | 125 | 28 | 22 | 25 | 0.050 | 0.10 | 0.10 |
| | 3 | 575 | 50 | 78 | 28 | 22 | 25 | 0.046 | 0.10 | 0.10 |
| | 4 | 575 | 50 | 85 | 28 | 22 | 25 | 0.046 | 0.10 | 0.10 |
| | 5 | 575 | 50 | 75 | 28 | 22 | 25 | 0.046 | 0.10 | 0.10 |
| | 6 | 430 | 30 | 95 | 32 | 30 | 31 | 0.054 | 0.10 | 0.10 |
| Comparative Example | 1 | 38 | 150 | 40 | 32 | 30 | 31 | 0.054 | 0.10 | 0.10 |
| | 2 | 450 | 30 | 80 | 28 | 27 | 25 | 0.054 | 0.10 | 0.10 |
| | 3 | 450 | 30 | 90 | 28 | 27 | 25 | 0.054 | 0.10 | 0.10 |
| | 4 | 450 | 30 | 94 | 28 | 27 | 25 | 0.054 | 0.10 | 0.10 |

TABLE 2-continued

|  |  | Discharged liquid | | Coating thickness [nm] | Shell/Core SiO$_2$/ZnO Molar ratio | | Particle diameter (D) [nm] | Core particle diameter (Dc) [nm] | D/Dc |
|---|---|---|---|---|---|---|---|---|---|
|  |  | pH | Temperature [° C.] |  | Calcurated value | EDS |  |  |  |
| Example | 1 | 13.29 | 28.1 | 1.82 | 0.37 | 0.37 | 20.10 | 16.46 | 122.1% |
|  | 2 | 13.87 | 28.1 | 0.33 | 0.11 | 0.11 | 10.40 | 9.74 | 106.8% |
|  | 3 | 13.96 | 31.4 | 0.35 | 0.11 | 0.11 | 9.80 | 9.10 | 107.7% |
|  | 4 | 13.96 | 31.4 | 0.36 | 0.12 | 0.12 | 9.80 | 9.08 | 107.9% |
|  | 5 | 13.96 | 31.4 | 0.40 | 0.16 | 0.16 | 9.60 | 8.80 | 109.1% |
|  | 6 | 12.34 | 33.2 | 0.71 | 0.12 | 0.12 | 21.40 | 19.98 | 107.1% |
| Comparative Example | 1 | 12.37 | 33.1 | — | 0.11 | — | — | — | — |
|  | 2 | 11.47 | 28.1 | — | 0.10 | — | — | — | — |
|  | 3 | 10.22 | 28.1 | — | 0.11 | — | — | — | — |
|  | 4 | 8.80 | 28.1 | — | 0.11 | — | — | — | — |

The molar ratios (shell/core) described in Table 2 are the ratio of the oxides of the elements, which the molar ratio of the elements calculated by the TEM-EDS analysis on one core-shell type oxide particle is converted into. For example, the molar ratio (shell/core, SiO$_2$/ZnO) in Example 1 of Table 2 is the value of SiO$_2$/ZnO converted from the molar ratio of Si/Zn calculated by with TEM-EDS analysis on one core-shell type oxide particle. Table 2 shows the average molar ratio (SiO$_2$/ZnO) of 10 particles together with its calculated value. The calculated value was calculated from the Zn concentration in the oxide raw material liquid for core and its introduction flow rate, and the Si concentration in the oxide raw material liquid for shell and its introduction flow rate.

Figure 3:
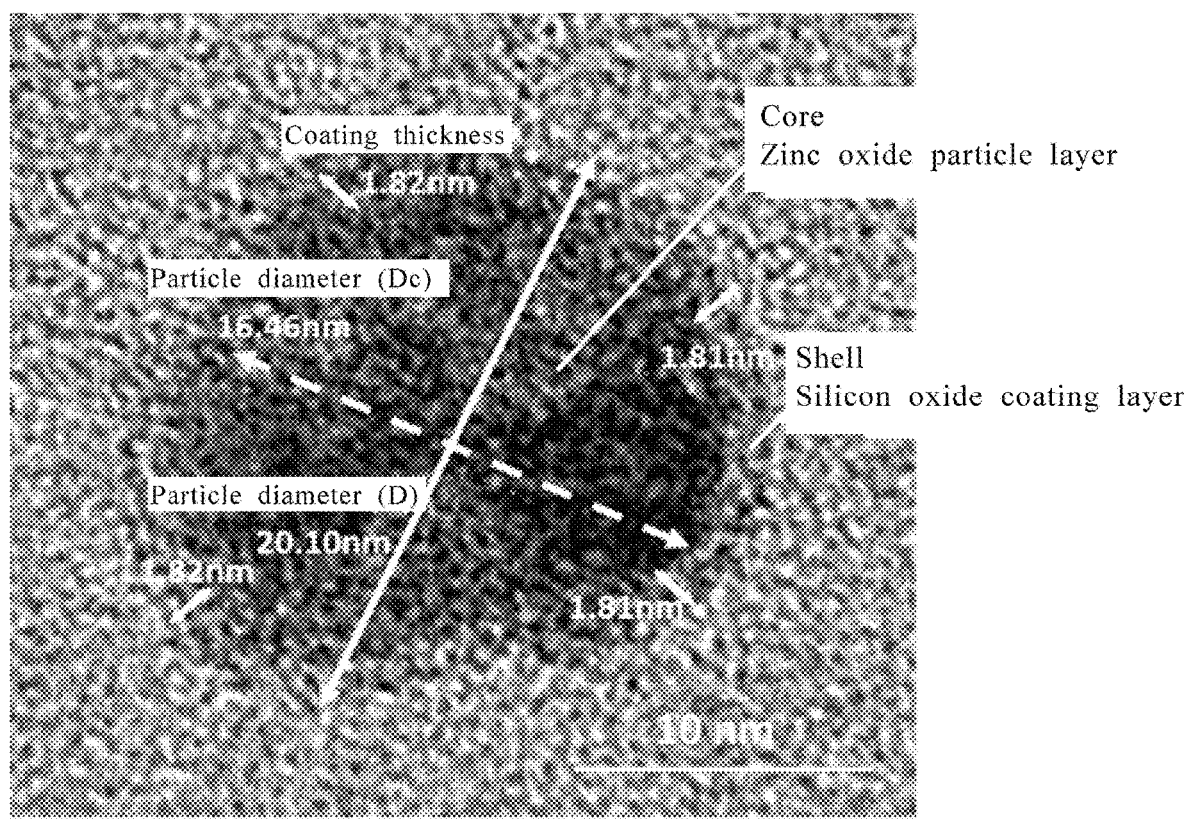
FIG. 3 shows a TEM photograph of the core-shell type oxide particles obtained in Example 1 of the present invention.

FIG. 3 shows a TEM photograph of the core-shell type oxide particles obtained in Example 1. Silicon oxide-coated zinc oxide particles wherein the core was one single zinc oxide particle and the shell was a silicon oxide, and the entire surface of the core was uniformly coated with shell, were observed, and a coating layer (shell) of silicon oxide having a thickness of about 1.8 nm on the entire surface of the core zinc oxide particle was observed. FIG. 4 shows a mapping result using STEM of the silicon oxide-coated zinc oxide particles obtained in Example 1. In FIG. 4, (a) shows a mapping of a dark-field image (HAADF image), (b) shows a mapping of oxygen (O), (c) shows a mapping of zinc (Zn), and (d) shows a mapping of silicon (Si). Regarding the observed particles in the I-IAADF image, distribution of oxygens (O) and silicons (Si) in the entire particles was observed, and distribution of zinc (Zn) in about 1.8 nm smaller area in radius compared with the particles was observed. D/Dc was 122.1%.

Figure 6:
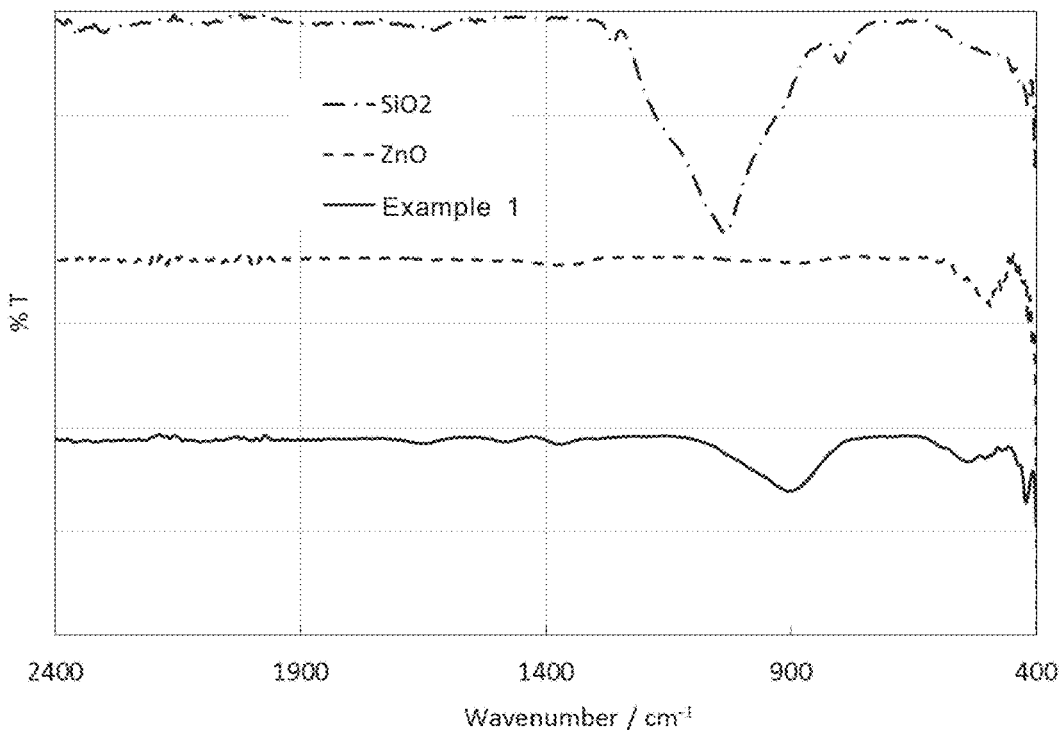
FIG. 6 shows an IR measurement results of the core-shell type oxide particles obtained in Example 1 of the present invention.

FIG. 5 shows XRD measurement results of the silicon oxide-coated zinc oxide particles obtained in Example 1. In the measurement results, peaks derived from zinc oxide (ZnO) were observed, and no other peaks were observed. FIG. 6 shows IR (infrared absorption spectrum) measurement results of the silicon oxide-coated zinc oxide particles obtained in Example 1, together with IR measurement results of silicon dioxide (SiO$_2$) and zinc oxide (ZnO). As shown in FIG. 6, a broad peak around 900 cm$^{-1}$ was observed for the silicon oxide-coated zinc oxide particles obtained in Example 1. This peak was not observed in the zinc oxide (ZnO), and the wave number of this peak is lower than that of the peak at around 1000 cm$^{-1}$ observed in SiO$_2$. Therefore, it was considered possible that the silicon oxide in the silicon oxide-coated zinc oxide particles obtained in Example 1 is in the state of SiO$_2$ or in the state wherein a part of oxygen is deficient like SiO$_{2-X}$.

For the IR measurement, the Fourier transform infrared spectrophotometer FT/IR-4100 (JASCO Corporation) was used. The measurement condition was the resolution of 4.0 cm$^{-1}$ and accumulated number of 1,024 times, using an ATR method.

Examples 2 to 6, Comparative Examples 1 to 4:
Using the Apparatus of FIG. 1(A)

Figure 7:
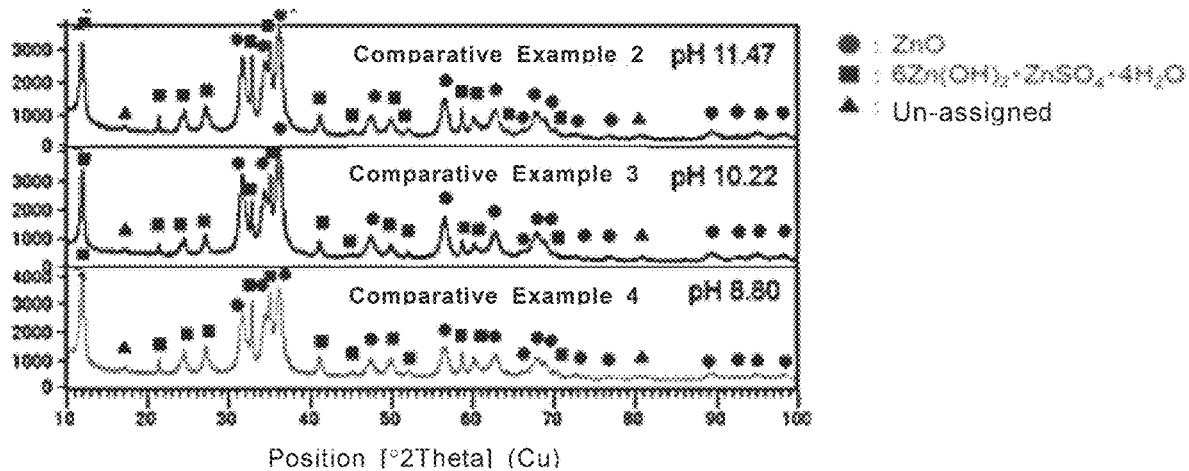
FIG. 7 shows an XRD measurement result of the particles obtained in Comparative Examples 2 to 4 of the present invention.

In the same manner as in Example 1 but using the apparatus of FIG. 1(A), the processing was performed using the formulations of the oxide raw material liquid for core, oxide precipitation solvent and oxide raw material liquid for shell described in Table 1 under the processing conditions (introduction flow rate, introduction temperature, introduction pressure) described in Table 2, to precipitate core-shell type oxide particles between the processing surfaces 1 and 2. Dry powders and wet cake sample were prepared from the core-shell type oxide particle dispersion discharged from the fluid processing apparatus and collected in the beaker b through the vessel v. TEM observation, XRD measurement and the like were performed in the same procedure as in Example 1, and the results as shown in Table 2 were obtained. Conditions not described in Table 2 were the same as those in Example 1. The time from introduction of liquid B into the space between the processing surfaces 1 and 2 until discharge of the core-shell type oxide particle dispersion from the space between the processing surfaces 1 and 2 was 0.5 seconds for most of the particles, and was within 1 second. FIG. 7 shows the XRD measurement results of the particles obtained in Comparative Examples 2 to 4. It was found that in Examples 1 to 6, the particle diameter, the core particle diameter and the thickness of the shell oxide (coating thickness) could be changed by changing the formulations and processing conditions of the fluid processing apparatus. As in Comparative Example 1, even using the same substances as those in Example 2, when flow rate of liquid B was higher than flow rate of liquid A, many zinc oxide particles without coating with a silicon oxide were observed, and uniform coating processing was impossible. Therefore, the particle diameter (D) was not measured. In Comparative Examples 2 to 4, the case consisting of particles consisting of only oxide for core and particles of only component for shell, and the case comprising such particles were observed. Further, as in Comparative Examples 2 to 4, when pH of the discharged liquid was 12 or less, it was not preferable since substances other than zinc oxide were also produced as core oxide particles, as shown in FIG. 7. However, pH of the discharged liquid is not restricted in the present application, and the particle diameter, the core particle diameter and the thickness of the shell oxide (coating thickness) can be controlled by changing the formulations of liquids A, B and C and processing conditions of the fluid processing apparatus in the present application.

Comparative Example 5

Using the same formulations as in Example 2 and the high-speed rotary dispersion emulsification apparatus CLEARMIX (product name: GLM-2.2 S, M Technique Co., Ltd.), the oxide raw material liquid for core, oxide precipitation solvent, and oxide raw material liquid for shell were prepared.

Next, the prepared oxide raw material liquid for core and oxide precipitation solvent were mixed in the fluid processing apparatus shown in FIG. 1(B). Specifically, the oxide precipitation solvent (MeOH 93.70/97 wt % $H_2SO_4$ 6.30) (weight ratio) as liquid A was introduced into the space between the processing surfaces 1 and 2 at 28° C. and at 460 ml/min. While driving the processing member 10 at a rotational speed of 1,130 rpm, the oxide raw material liquid for core (ZnO 3.0/KOH 46.6/pure water 50.4) (weight ratio) as liquid B was introduced into the space between the processing surfaces 1 and 2 at 22° C. and at 40 ml/min. The oxide precipitation solvent and oxide raw material liquid for core were mixed in the thin film fluid to precipitate the core oxide particles (zinc oxide particles) between the processing surfaces 1 and 2. A discharged liquid containing the core zinc oxide particles (hereinafter, referred to as zinc oxide particle dispersion) was discharged from the space between the processing surfaces 1 and 2 of the fluid processing apparatus (Step 1). The discharged zinc oxide particle dispersion was collected in the beaker b through the vessel v. pH of the discharged liquid was 13.91 (measurement temperature 28.1° C.). The zinc oxide particles in the collected zinc oxide particle dispersion had been already aggregated. The processing conditions are described in Example 2 except for the oxide raw material liquid for shell.

Figure 8:
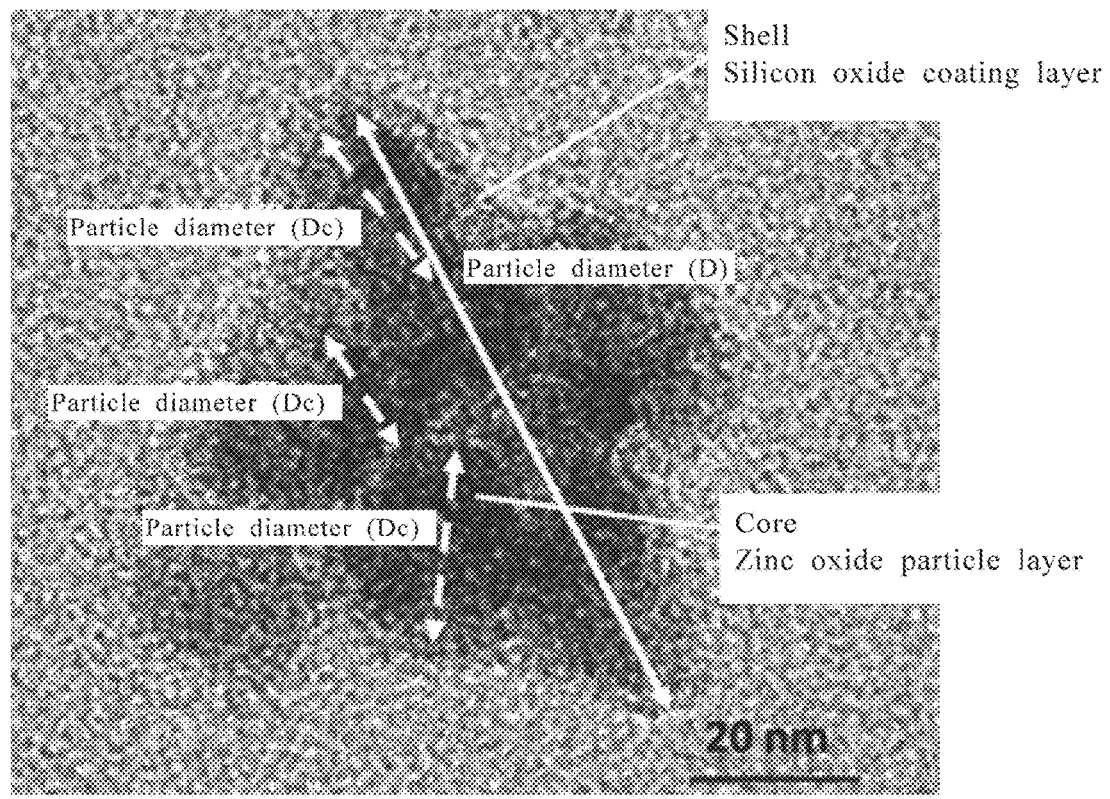
FIG. 8 shows a TEM photograph of the core-shell type oxide particles obtained in Comparative Example 5 of the present invention.

Next, the collected zinc oxide particle dispersion and the oxide raw material liquid for shell (MeOH 94.61/35 wt % HCl 5.11/TEOS 0.28) (weight ratio) were mixed using the high-speed rotary dispersion emulsification apparatus CLEARMIX (Product name: CLM-2.2 S, M Technique Co., Ltd.). Specifically, while 500 parts by weight of the dispersion containing the zinc oxide particle dispersion in the beaker b were stirred at a temperature of 25° C. using CLEARMIX at a rotor rotational speed of 10,000 rpm, 125 parts by weight of the oxide raw material liquid for shell were introduced into the beaker b and stirred for 30 minutes to homogeneously mix the dispersion containing zinc oxide particles and the oxide raw material liquid for shell, and to precipitate a silicon oxide on the surface of the zinc oxide particles, so that the surface of the zinc oxide particles were coated with a silicon oxide (Step 2). pH of the fluid after mixing was 13.79 (measurement temperature 28.1° C.). In Comparative Example 5, the time required for transition from Step 1 to Step 2, namely the time until introduction of 125 parts by weight of the oxide raw material liquid for shell into the beaker b while stirring 500 parts by weight of the dispersion containing the zinc oxide particles in the beaker b, was 2 minutes. Dry powders and wet cake sample were prepared from the dispersion in the beaker b. As a result of the TEM observation of the core-shell type oxide particles produced by the method of Comparative Example 5, the zinc oxide particles wherein the entire surface of one single zinc oxide particle was uniformly coated with a silicon oxide as obtained in Examples 1 to 6, were not observed, and many particles wherein a plurality of zinc oxide particles were coated with a silicon oxide shell were observed, and D/Dc of the particles was 334%. FIG. 8 shows the TEM photograph of the core-shell type oxide particles obtained in Comparative Example 5. As shown in FIG. 8, it can be seen that the aggregates of the core zinc oxide primary particles are coated with a shell silicon oxide.

Example 7

In the same manner as in Comparative Example 5 but using the apparatus of FIG. 1(B), liquid A (the oxide precipitation solvent) and liquid B (the oxide raw material liquid for core) were mixed in the thin film fluid formed between the processing surfaces 1 and 2 to precipitate zinc oxide particles between the processing surfaces 1 and 2, and the discharged liquid containing the zinc oxide particles (hereinafter referred to as zinc oxide particle dispersion) from the space between the processing surfaces 1 and 2 of the fluid processing apparatus. Next, the oxide raw material liquid for shell as the third fluid was introduced from an inlet (not shown in FIG.) provided in the vessel v at 25° C. and at 125 ml/min. The zinc oxide dispersion immediately after discharge from the space between the processing surfaces 1 and 2 and the oxide raw material liquid for shell were mixed inside the vessel v, and collected in the beaker b. pH of the dispersion collected in the beaker b was 13.92 (measurement temperature 28.4° C.). Dry powders and wet cake sample were prepared from the dispersion collected in the beaker b. The time from introduction of liquid B into the space between the processing surfaces 1 and 2 until discharge of the zinc oxide particle dispersion from the space between the processing surfaces 1 and 2 followed by collection of the mixed fluid of the discharged zinc oxide dispersion and oxide raw material liquid for shell in the beaker b, was 0.8 seconds for most of the particles, and was within 1 second. As a result of the TEM observation of the core-shell type oxide particles produced by the method of Example 7, zinc oxide particles wherein the entire surface of one single zinc oxide particle is uniformly coated with a silicon oxide, namely silicon oxide-coated zinc oxide particles were observed. The particle diameter (D) was 26.5 nm, the thickness of the shell oxide (coating thickness) was 2.3 nm, and D/Dc of the silicon oxide coated zinc oxide particles was 121.0%.

Comparative Example 6

Using the same formulations as in Example 2 and the high-speed rotary dispersion emulsification apparatus CLEARMIX (product name: CLM-2.2 S, M Technique Co., Ltd.), the oxide raw material liquid for core, oxide precipitation solvent, and oxide raw material liquid for shell were prepared. Next, the prepared oxide raw material liquid for core and oxide precipitation solvent were stirred and mixed in a beaker using a magnetic stirrer. The rotational speed of the magnetic stirrer was 600 rpm. Specifically, while 4,600 ml of the oxide precipitation solvent (MeOH 93.70/97 wt % $H_2SO_4$ 6.30) (weight ratio) was stirred at 28° C., 400 ml of the oxide raw material liquid for core (ZnO 3.0/KOH 46.6/pure water 50.4) (weight ratio) was introduced thereto at 22° C. and at 10 ml/min, to precipitate zinc oxide particles and to obtain a zinc oxide particle dispersion. pH of the zinc oxide particle dispersion was 13.89 (measurement temperature 28.1° C.). The zinc oxide particles in the obtained zinc oxide particle dispersion had been already aggregated.

Next, the obtained zinc oxide particle dispersion as liquid A was introduced at 33° C. and at 500 ml/min using the fluid processing apparatus of FIG. 1(B), and while driving the processing member 10 at a rotational speed of 1,130 rpm, the oxide raw material liquid for shell (MeOH 94.61/35 wt % HCl 5.11/TEOS 0.28) (weight ratio) as liquid B was introduced at 25° C. and at 125 ml/min into the space between the processing surfaces 1 and 2. The zinc oxide particle dispersion and the oxide raw material liquid for shell were mixed in the thin film fluid. A discharged liquid containing the core-shell type oxide particles wherein the surface of zinc oxide particles were coated with a shell oxide (hereinafter, referred to as core-shell type oxide particle dispersion) was discharged from the space between the processing surfaces 1 and 2 of the fluid processing apparatus. The discharged core-shell type oxide particle dispersion was collected in the beaker b through the vessel v. pH of the discharged liquid was 13.80 (measurement temperature 28.3° C.). The time from setting the obtained zinc oxide dispersion in the fluid processing apparatus until discharge of the dispersion from the space between the processing surfaces 1 and 2 was about 5 minutes for most of the particles, and the total processing time of Comparative Example 6 was 10 minutes. Dry powders and wet cake sample were prepared from the dispersion collected in the beaker b. As a result of the TEM observation of the core-shell type oxide particles produced by the method of Comparative Example 6, the zinc oxide particles wherein the entire surface of one single zinc oxide particle was uniformly coated with a silicon oxide as obtained in Examples 1 to 6, were not observed, and many particles wherein a plurality of zinc oxide nanoparticles were coated with a silicon oxide shell were observed, and D/Dc of the particles was 396%.

Comparative Example 7

Zinc oxide particles whose surface was not coated with a silicon oxide were prepared for comparison with zinc oxide particles whose surface was coated with a silicon oxide.

Using the same formulations of the oxide raw material liquid for core and oxide precipitation solvent as those in Example 2, and the high-speed rotary dispersion emulsification apparatus CLEARMIX (Product name: CLM-2.2S, M Technique Co., Ltd.), the oxide raw material liquid for core and oxide precipitation solvent were prepared.

Next, zinc oxide particles were prepared using the prepared oxide raw material liquid for core and oxide precipitation solvent and the fluid processing apparatus shown in FIG. 1(B) under the following conditions. Specifically, the oxide precipitation solvent (MeOH 93.70/97 wt % $H_2SO_4$ 6.30) (weight ratio) as liquid A was introduced into the space between the processing surfaces 1 and 2 at 22° C. and at 460 ml/min. While keeping the processing member 10 at a rotational speed of 1,130 rpm, the zinc oxide raw material liquid (ZnO 3.0/KOH 46.6/pure water 50.4) (weight ratio) as liquid B was introduced into the space between the processing surfaces 1 and 2 at 28° C. and at 40 ml/min. The oxide precipitation solvent and oxide raw material liquid for core were mixed in the thin film fluid to precipitate zinc oxide particles between the processing surfaces 1 and 2. A discharged liquid containing the zinc oxide particles (zinc oxide particle dispersion) was discharged from the space between the processing surfaces 1 and 2. The method of washing the particles, the analysis/evaluation method and the like were the same as in Example 1. The particle diameter measured in the same method as that of the core particle diameter in Example 1 was 10.1 nm, and from the XRD measurement results, only peaks of zinc oxide were detected. pH of the discharged liquid was 13.92 (measuring temperature 28.2° C.). The zinc oxide particles in the resulting zinc oxide particle dispersion had been already aggregated.

Figure 9:
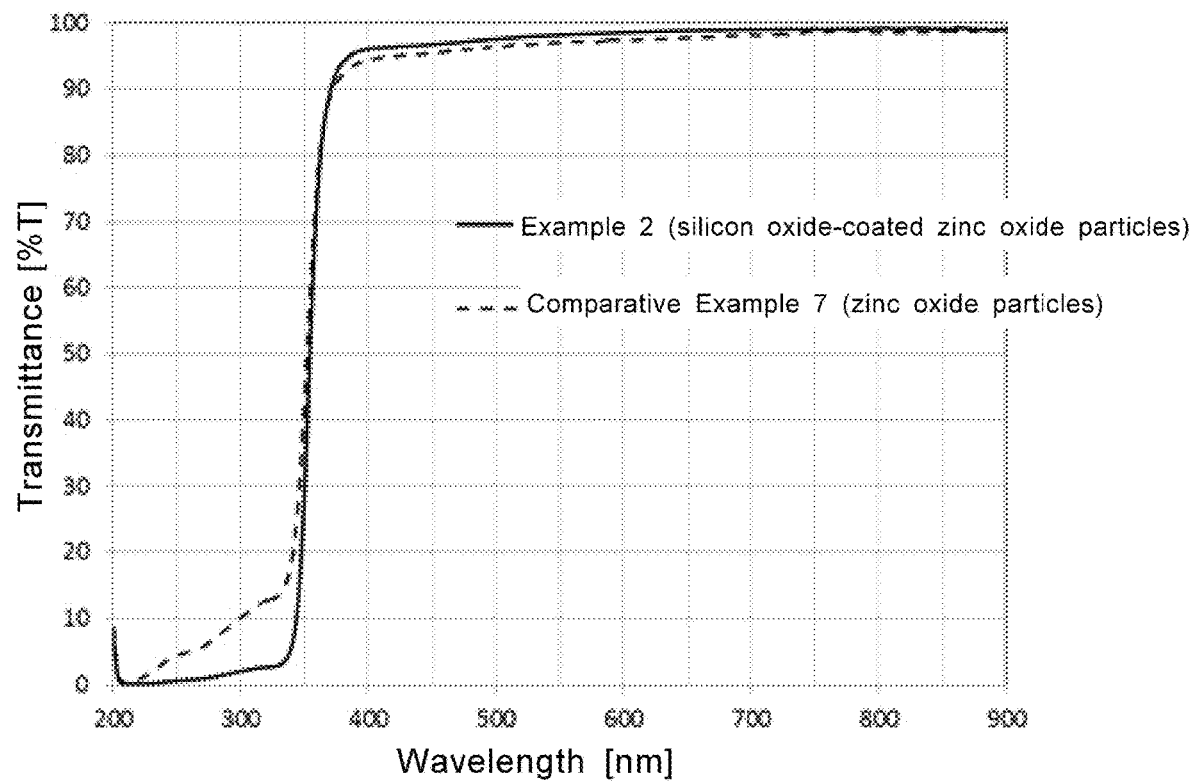
FIG. 9 shows a transmission spectrum of the core-shell type oxide particles obtained in Example 2 of the present invention, and of the oxide particles obtained in Comparative Example 7.
Figure 10:
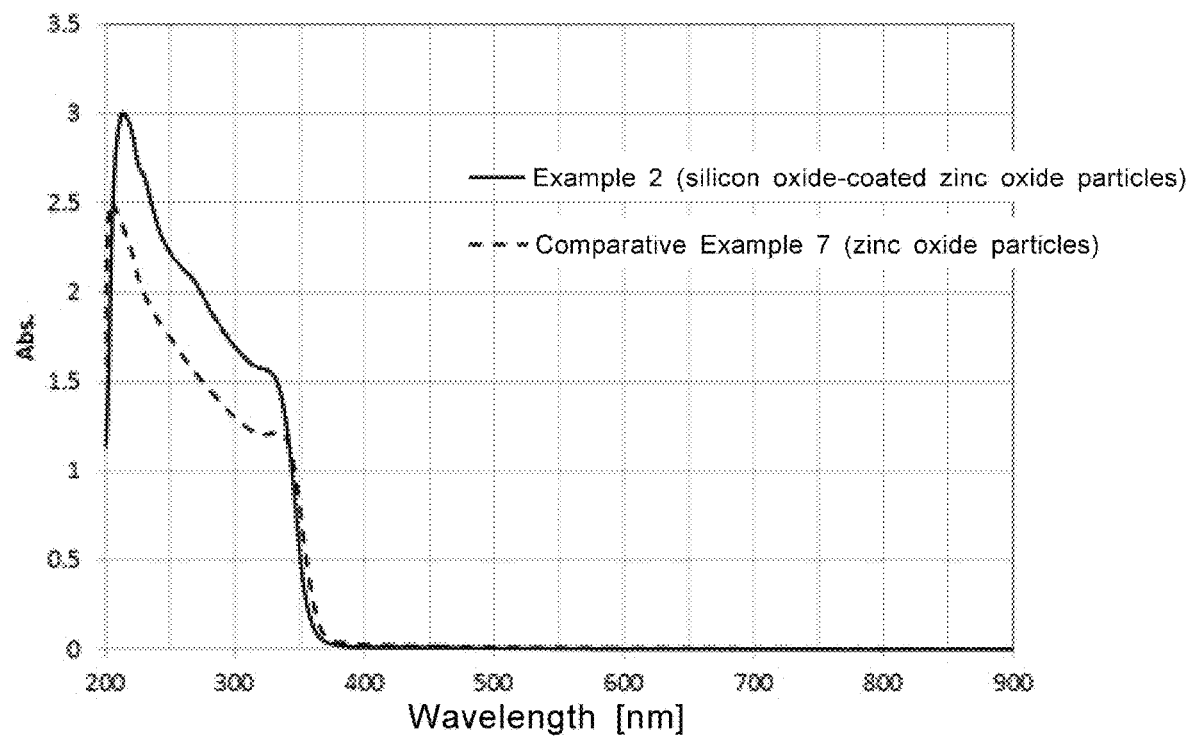
FIG. 10 shows an absorption spectrum of the core-shell type oxide particles obtained in Example 2 of the present invention, and of the oxide particles obtained in Comparative Example 7.

The dispersion wherein the silicon oxide-coated zinc oxide particles obtained under the conditions of Example 2 were dispersed in propylene glycol at a concentration of 0.00185 mol/L, and the dispersion wherein the zinc oxide particles obtained under the conditions of Comparative Example 7 were dispersed in propylene glycol at a concentration of 0.00185 mol/L were prepared. The ultraviolet-visible absorption spectroscopic measurement results of both dispersions are shown in FIG. 9 (transmittance) and FIG. 10 (absorbance). As shown from FIGS. 9 and 10, it was found that the dispersion prepared by dispersing the zinc oxide particles obtained in Example 2 wherein the entire surface of the zinc oxide was uniformly coated with a silicon oxide, easily absorbed strongly a light of a wavelength of the absorption region 200 to 350 nm, and easily transmitted a light of a wavelength of the transmission region 370 to 800 nm, compared with the dispersion prepared by dispersing the zinc oxide particles obtained in Comparative Example 7. It is considered that affinity with the solvent is improved and dispersibility of the particles is improved by uniformly coating the entire surface of one single zinc oxide particle with a silicon oxide.

(Photocatalytic Activity Evaluation)

Figure 11:
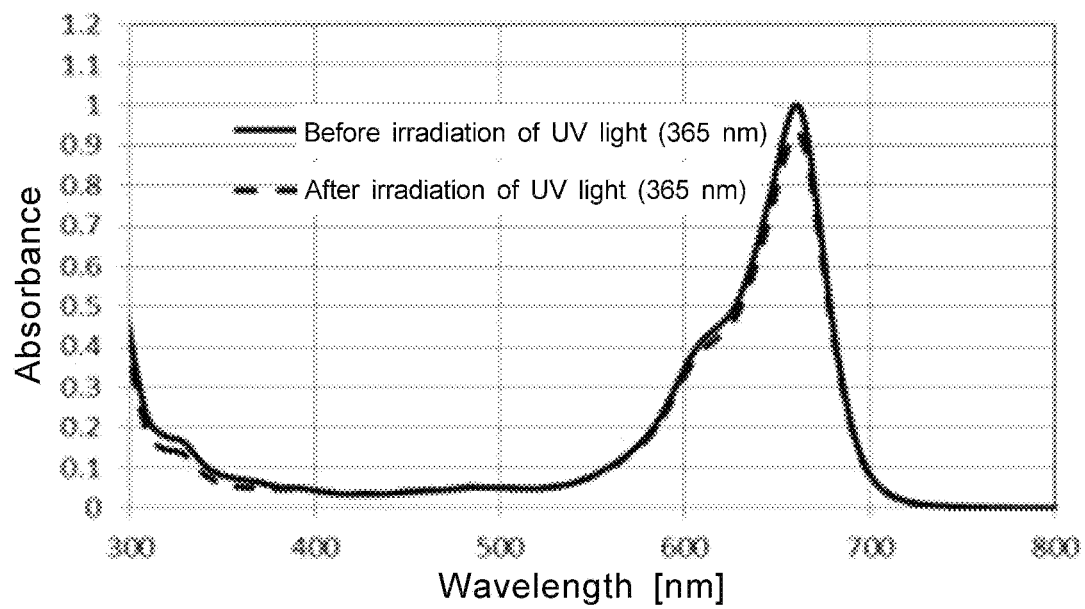
FIG. 11 shows an absorption spectrum of a dispersion in which the core-shell type oxide particles obtained in Example 1 of the present invention are dispersed in propylene glycol dissolving methylene blue dye, before and after irradiation with an ultraviolet light of 365 nm for 2 hours.
Figure 12:
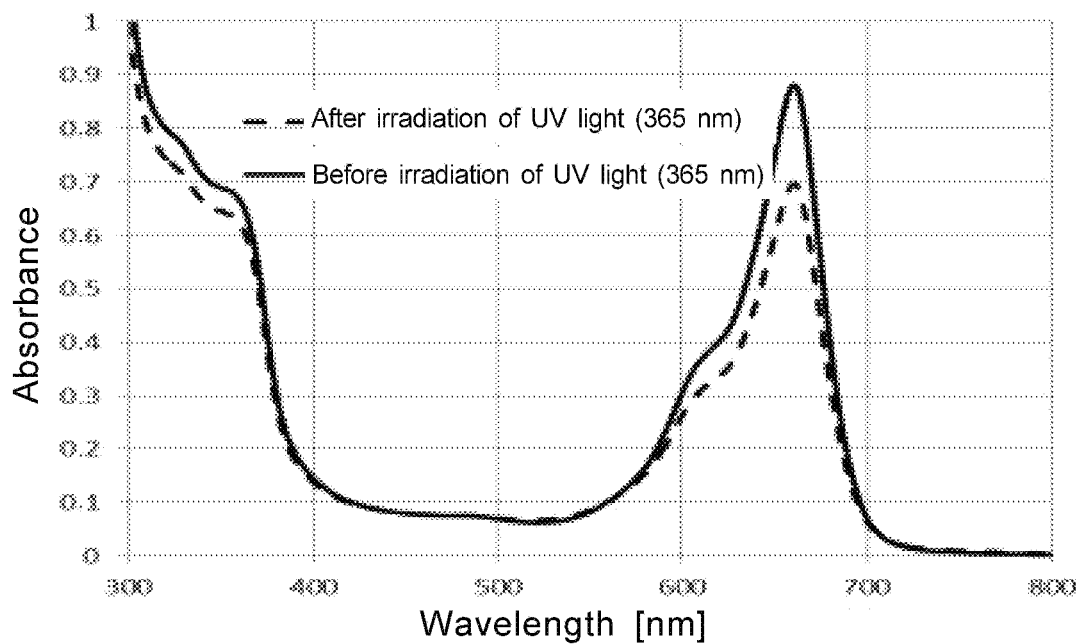
FIG. 12 shows an absorption spectrum of a dispersion in which the core-shell type oxide particles obtained in Comparative Example 7 of the present invention are dispersed in propylene glycol dissolving methylene blue dye, before and after irradiation with an ultraviolet light of 365 nm for 2 hours.

Photocatalytic activities of the particles obtained in Examples 1 to 7 and Comparative Examples 1 to 7 were evaluated. Specifically, the particles obtained in Examples or Comparative Examples were dispersed in propylene glycol dissolving methylene blue dye, and an ultraviolet light of 365 nm was irradiated for 2 hours, and ultraviolet-visible absorption spectra were measured before and after irradiation. A transilluminator (TFX 20 CL, Vilber Lourmat) was used for irradiation of an ultraviolet light of 365 nm. Photocatalytic activity was evaluated by attenuation rate of absorbance (Formula 1) for a light of a wavelength around 660 nm derived from the absorption peak of methylene blue dye. A concentration of methylene blue in propylene glycol was set so that the absorbance for a wavelength 660 nm was around 1 in the measurement before irradiation with an ultraviolet light, and the dispersion concentration of the particles was set to $5 \times 10^{-5}$ mol/L. FIG. 11 shows the absorption spectrum measurement results of the particles obtained under the conditions of Example 1 before and after irradiation with an ultraviolet light. FIG. 12 shows the absorption spectrum measurement results of the particles obtained under the conditions of Comparative Example 7 before and after irradiation with an ultraviolet light. In the case of the silicon oxide-coated zinc oxide particles obtained in Example 1, substantially no changes were observed in the absorbance for a light of a wavelength 660 nm, before and after irradiation with an ultraviolet light of 365 nm for 2 hours (the maximum absorbance after irradiation relative to the maximum absorbance before irradiation was 0.90 to 1.00). In the case of the particles prepared in Comparative Example 7, the absorbance was attenuated, and the maximum absorbance after irradiation relative to the maximum absorbance before irradiation fell to less than 0.90. The particles produced under the conditions of Comparative Examples 1 to 6 showed the same tendency as in Comparative Example 7. It was found that with respect to the particles produced under the conditions of Examples 1 to 7, photocatalytic ability of the zinc oxide particles could be suppressed by uniformly coating the entire surface of one single zinc oxide particle with a silicon oxide, but with respect to the particles produced under the conditions of Comparative Examples 1 to 6, photocatalytic ability of the zinc oxide could not be suppressed because the zinc oxide particles included those wherein the surface of the zinc oxide particles were not coated with a silicon oxide or those wherein the surface of a plurality of zinc oxide particles were coated with a silicon oxide.

Example 8

The oxide raw material liquid for core, oxide precipitation solvent, and oxide raw material liquid for shell were prepared using the high-speed rotary dispersion emulsification apparatus CLEARMIX (product name: CLM-2.2 S, M. Technique Co., Ltd.). Specifically, based on the formulation of the oxide raw material liquid for core shown in Example 8 of Table 3, the components of the oxide raw material liquid for core were mixed homogeneously by stirring using CLEARMIX at preparation temperature of 40° C. and at the rotor rotational speed of 20,000 rpm for 30 min to prepare the oxide raw material liquid for core. Based on the formulation of the oxide precipitation solvent shown in Example 8 of Table 3, the components of the oxide precipitation solvent were mixed homogeneously by stirring using CLEARMIX at preparation temperature of 45° C. and at the rotor rotational speed of 15,000 rpm for 30 min to prepare the oxide precipitation solvent. Furthermore, based on the formulation of the oxide raw material liquid for shell shown in Example 8 of Table 3, the components of the oxide raw material liquid for shell were mixed homogeneously by stirring using CLEARMIX at preparation temperature of 20° C. and at the rotor rotational speed of 6,000 rpm for 10 min to prepare the oxide raw material liquid for shell.

Regarding the substances represented by the chemical formula and abbreviations set forth in Table 3, 97 wt % $H_2SO_4$ is concentrated sulfuric acid (Kishida Chemical Co., Ltd.), NaOH is sodium hydroxide (Kanto Chemical Co., Inc.), TEOS is tetraethyl orthosilicate (Wako Pure Chemical Industry Ltd.), and $Fe(NO_3)_3 \cdot 9H_2O$ is iron nitrate nonahydrate (Kanto Chemical Co., Inc.). The method of washing particles and the analysis/evaluation method were the same as in Example 1.

Then, the prepared oxide raw material liquid for core, oxide precipitation solvent, and oxide raw material liquid for shell were mixed by the fluid processing apparatus shown in FIG. 1(A). Specifically, the oxide raw material liquid for core as liquid A was introduced into the space between the processing surfaces 1 and 2, and while driving the processing member 10 at a rotational speed of 1,130 rpm, the oxide precipitation solvent as liquid B was introduced into the space between the processing surfaces 1 and 2, and the oxide raw material liquid for core and the oxide precipitation solvent were mixed in the thin film fluid, to precipitate the core oxide particles in the space between the processing surfaces 1 and 2. Then, the oxide raw material liquid for shell as liquid C was introduced into the space between the processing surfaces 1 and 2, and liquid C was mixed with a mixed fluid containing the core oxide particles in the thin film fluid. As a result, an oxide for shell was precipitated on the surface of the core oxide particles. The discharged liquid containing the core-shell type oxide particles (hereinafter, the core-shell type oxide particle dispersion) was discharged from the space between the processing surfaces 1 and 2 of the fluid processing apparatus. The discharged core-shell type oxide particle dispersion was collected in the beaker b through the vessel v. The time from introduction of liquid B into the space between the processing surfaces 1 and 2 until discharge of the core-shell type oxide particle dispersion from the space between the processing surfaces 1 and 2 was 0.4 seconds for most of the particles, and was within 1 second.

Table 4 shows the operating conditions of the fluid processing apparatus. The introduction temperatures (liquid sending temperatures) and the introduction pressures (liquid sending pressures) of liquid A, liquid B and liquid C shown in Table 4 were measured using thermometers and pressure gauges provided in sealed inlet paths leading to the space between the processing surfaces 1 and 2 (the first introduction part d1, the second introduction part d2 and the third introduction part d3). The introduction temperature of liquid A shown in Table 4 was the actual temperature of liquid A under the introduction pressure in the first introduction part d1. Similarly, the introduction temperature of liquid B shown in Table 4 was the actual temperature of liquid B under the introduction pressure in the second introduction part d2. The introduction temperature of liquid C shown in Table 4 was the actual temperature of liquid C under the introduction pressure in the third introduction part d3.

TABLE 3

| | | | Formulation of First fluid (Liquid A) | | | | | | Formulation of Second fluid (Liquid B) | | |
|---|---|---|---|---|---|---|---|---|---|---|---|
| | | | Formulation [wt %] | | | | | | Formulation [wt %] | | |
| | | | Raw | | Raw | | pH | | Raw | | |
| | | | material | [wt %] | material | [wt %] | pH | [° C.] | | material | [wt %] |
| Example | 8 | Oxide raw material liquid for core | $Fe(NO_3)_3$ $9H_2O$ | 2.00 | Pure water | 98.00 | 1.8 | 26.6 | Oxide precipitation solvent | NaOH | 9.00 |
| | 9 | | $Fe(NO_3)_3$ $9H_2O$ | 2.00 | Pure water | 98.00 | 1.8 | 26.6 | | NaOH | 9.00 |
| Comparative Example | 8 | Oxide precipitation solvent | NaOH | 9.00 | Pure water | 91.00 | >14 | — | Oxide raw material liquid for core | $Fe(NO_3)_3$ $9H_2O$ | 2.00 |
| | 9 | | NaOH | 9.00 | Pure water | 91.00 | >14 | — | | $Fe(NO_3)_3$ $9H_2O$ | 2.00 |

TABLE 3-continued

| | | Formulation of Second fluid (Liquid B) | | | | Formulation of Third fluid: Oxide raw material liquid for shell (Liquid C) | | | | | | |
|---|---|---|---|---|---|---|---|---|---|---|---|---|
| | | Formulation [wt %] | | pH | | Formulation [wt %] | | | | | pH | |
| | | Raw material | [wt %] | pH | [° C.] | Raw material | [wt %] | Raw material | [wt %] | Raw material | [wt %] | pH | [° C.] |
| Example | 8 | Pure water | 91.00 | >14 | — | Pure water | 92.89 | 97 wt % $H_2SO_4$ | 5.11 | TEOS | 2.00 | <1 | — |
| | 9 | Pure water | 91.00 | >14 | — | Pure water | 93.70 | 97 wt % $H_2SO_4$ | 5.11 | TEOS | 1.19 | <1 | — |
| Comparative Example | 8 | Pure water | 98.00 | 1.8 | 26.6 | Pure water | 92.89 | 97 wt % $H_2SO_4$ | 5.11 | TEOS | 2.00 | <1 | — |
| | 9 | Pure water | 98.00 | 1.8 | 26.6 | Pure water | 93.70 | 97 wt % $H_2SO_4$ | 5.11 | TEOS | 1.19 | <1 | — |

TABLE 4

| | | Introduction flow rate [ml/min] | | | Introduction temperature (liquid sending temperature) [° C.] | | | Introduction pressure (liquid sending pressure) [MPaG] | | |
|---|---|---|---|---|---|---|---|---|---|---|
| | | Liquid A | Liquid B | Liquid C | Liquid A | Liquid B | Liquid C | Liquid A | Liquid B | Liquid C |
| Example | 8 | 400 | 50 | 100 | 142 | 86 | 89 | 0.451 | 0.50 | 0.50 |
| | 9 | 400 | 50 | 100 | 142 | 86 | 89 | 0.451 | 0.50 | 0.50 |
| Comparative Example | 8 | 50 | 400 | 100 | 142 | 131 | 105 | 0.451 | 0.50 | 0.50 |
| | 9 | 50 | 400 | 100 | 142 | 131 | 105 | 0.451 | 0.50 | 0.50 |

| | | Discharged liquid | | Coating thickness [nm] | Shell/Core $SiO_2/Fe_2O_3$ Molar ratio | | Particle diameter (D) [nm] | Core particle diameter (Dc) [nm] | D/Dc |
|---|---|---|---|---|---|---|---|---|---|
| | | pH | Temperature [° C.] | | Calcurated value | EDS | | | |
| Example | 8 | 12.14 | 32.9 | 1.37 | 0.97 | 0.97 | 8.20 | 5.46 | 150.2% |
| | 9 | 11.98 | 32.9 | 0.35 | 0.58 | 0.58 | 6.40 | 5.70 | 112.3% |
| Comparative Example | 8 | 12.14 | 32.9 | — | 0.97 | — | — | — | — |
| | 9 | 11.98 | 32.9 | — | 0.58 | — | — | — | — |

The molar ratios (shell/core) described in Table 4 are the ratio of the oxides of the elements, which the molar ratio of the elements calculated by the TEM-EDS analysis on one core-shell type oxide particle is converted into. For example, the molar ratio (shell/core, $SiO_2/Fe_2O_3$) in Example 8 of Table 4 is the value of $SiO_2/Fe_2O_3$ converted from the molar ratio of Si/Fe calculated by with TEM-EDS analysis on one core-shell type oxide particle. Table 2 shows the average molar ratio ($SiO_2/Fe_2O_3$) of 10 particles together with its calculated value. The calculated value was calculated from the Fe concentration in the oxide raw material liquid for core and its introduction flow rate, and the Si concentration in the oxide raw material liquid for shell and its introduction flow rate.

FIG. 13 shows a TEM photograph of the core-shell type oxide particles obtained in Example 8. Silicon oxide-coated iron oxide particles wherein the core was one single iron oxide particle and the shell was a silicon oxide, and the entire surface of the core was uniformly coated with shell, were observed, and a coating layer (shell) of silicon oxide having a thickness of about 1.37 nm on the entire surface of the core iron oxide particle was observed. FIG. 14 shows a mapping result using STEM of the silicon oxide-coated iron oxide particles obtained in Example 8. In FIG. 14, (a) shows a mapping of a dark-field image (HAADF image), (b) shows a mapping of oxygen (O), (c) shows a mapping of iron (Fe), and (d) shows a mapping of silicon (Si). Regarding the observed particles in the HAADF image, distribution of oxygens (O) and silicons (Si) in the entire particles was observed, and distribution of iron (Fe) in about 1.37 nm smaller area in radius compared with the particles was observed. MX was 150.2%.

Figure 15:
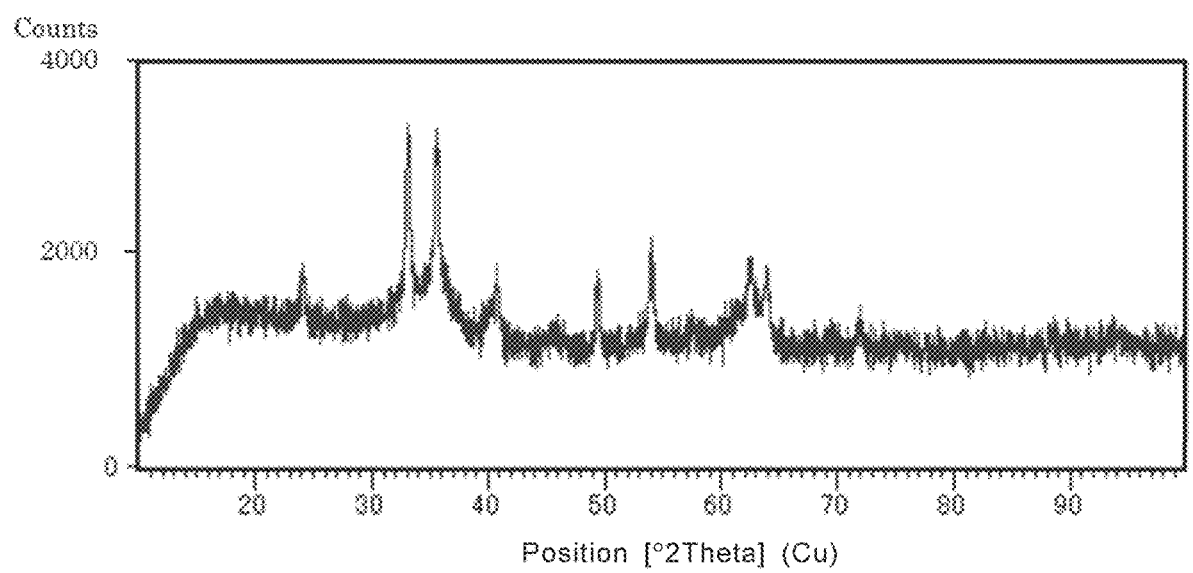
FIG. 15 shows an XRD measurement result of the core-shell type oxide particles obtained in Example 8 of the present invention.

From the XRD measurement results of the silicon oxide-coated iron oxide particles obtained in Example 8 shown in FIG. 15, peaks derived from iron oxide ($Fe_2O_3$) were detected, and no other peaks were observed.

Example 9, Comparative Examples 8 and 9

In the same manner as in Example 8 but using the apparatus of FIG. 1(A), the processing was performed using the formulations of the oxide raw material liquid for core, oxide precipitation solvent and oxide raw material liquid for shell described in Table 3 under the processing conditions (introduction flow rate, introduction temperature, introduction pressure) described in Table 4, to precipitate core-shell type oxide particles between the processing surfaces 1 and 2. Dry powders and wet cake sample were prepared from the core-shell type oxide particle dispersion discharged from the fluid processing apparatus and collected in the beaker b through the vessel v. TEM observation, XRD measurement and the like were performed in the same procedure as in Example 8, and the results as shown in Table 4 were obtained. Conditions not described in Table 4 were the same as those in Example 8. The time from introduction of liquid B into the space between the processing surfaces 1 and 2 until discharge of the core-shell type oxide particle dispersion from the space between the processing surfaces 1 and 2 was 0.3 seconds for most of the particles, and was within 1 second. It was found that in Examples 8 and 9, the particle diameter, the core particle diameter and the thickness of the shell oxide (coating thickness) could be changed by changing the formulations and processing conditions of the fluid processing apparatus. pH of the discharged liquid is not restricted in the present application, and the particle diameter, the core particle diameter and the thickness of the shell oxide (coating thickness) can be changed by changing the formulations of liquids A, B and C and processing conditions of the fluid processing apparatus in the present application. As in Comparative Examples 8 and 9, when flow rate of liquid B was higher than flow rate of liquid A, many iron oxide particles without coating with a silicon oxide were observed, and uniform coating processing was impossible. Therefore, the particle diameter (D) was not measured.

Comparative Example 10

In the same formulation as in Example 9, the oxide raw material liquid for core, oxide precipitation solvent, and oxide raw material liquid for shell were prepared using the high-speed rotary dispersion emulsification apparatus CLEARMIX (product name: CLM-2.2S, M Technique Co., Ltd.).

Next, the prepared oxide raw material liquid for core and oxide precipitation solvent were mixed in the fluid processing apparatus shown in FIG. 1(B). Specifically, the oxide raw material liquid for core (pure water 98.00/Fe(NO$_3$)$_3$·9H$_2$O 2.0) (weight ratio) as liquid A was introduced into the space between the processing surfaces 1 and 2 at 142° C. and at 400 ml/min. While driving the processing member 10 at a rotational speed of 1,130 rpm, the oxide precipitation solvent (NaOH 9.00/pure water 91.00) (weight ratio) as liquid B was introduced into the space between the processing surfaces 1 and 2 at 86° C. and at 50 ml/min. The oxide raw material liquid for core and oxide precipitation solvent were mixed in the thin film fluid to precipitate the core oxide particles (iron oxide particles) between the processing surfaces 1 and 2. A discharged liquid containing the core iron oxide particles (hereinafter, referred to as iron oxide particle dispersion) was discharged from the space between the processing surfaces 1 and 2 of the fluid processing apparatus. The discharged iron oxide particle dispersion was collected in the beaker b through the vessel v. pH of the discharged liquid was 12.51 (measurement temperature 32.9° C.). The iron oxide particles in the collected iron oxide particle dispersion had been already aggregated.

Next, the collected iron oxide particle dispersion and the oxide raw material liquid for shell (MeOH 93.70/35 wt % HCl 5.11/TEOS 1.19) (weight ratio) were mixed using the high-speed rotary dispersion emulsification apparatus CLEARMIX (Product name: CLM-2.2 S, M Technique Co., Ltd.). Specifically, while 450 parts by weight of the dispersion containing the iron oxide particle dispersion in the beaker b were stirred at a temperature of 98° C. using CLEARMIX at a rotor rotational speed of 10,000 rpm, 100 parts by weight of the oxide raw material liquid for shell were introduced into the beaker b and stirred for 30 minutes to homogeneously mix the dispersion containing iron oxide particles and the oxide raw material liquid for shell, and to precipitate a silicon oxide on the surface of the iron oxide particles, so that the surface of the iron oxide particles were coated with a silicon oxide (Step 2). pH of the fluid after mixing was 11.98 (measurement temperature 32.9° C.). In Comparative Example 10, the time required for transition from Step 1 to Step 2, namely the time until introduction of 100 parts by weight of the oxide raw material liquid for shell into the beaker b while stirring 450 parts by weight of the dispersion containing the iron oxide particles in the beaker b, was 5 minutes. Dry powders and wet cake sample were prepared from the dispersion in the beaker b. As a result of TEM observation of the core-shell type oxide particles produced by the method of Comparative Example 10, the iron oxide particles wherein the entire surface of one single iron oxide particle was uniformly coated with a silicon oxide as obtained in Examples 8 and 9, were not observed, and many particles wherein a plurality of iron oxide particles were coated with a silicon oxide shell were observed, and D/Dc of the particles was 412%.

Example 10

In the same manner as in Comparative Example 10 but using the apparatus of FIG. 1(B), liquid A (the oxide raw material liquid for core) and liquid B (the oxide precipitation solvent) were mixed in the thin film fluid formed between the processing surfaces 1 and 2 to precipitate iron oxide particles between the processing surfaces 1 and 2, and the discharged liquid containing the iron oxide particles (hereinafter, referred to as iron oxide particle dispersion) from the space between the processing surfaces 1 and 2 of the fluid processing apparatus. Next, the oxide raw material liquid for shell as the third fluid was introduced from an inlet (not shown in FIG.) provided in the vessel v at 89° C. and at 100 ml/min. The iron oxide dispersion immediately after discharge from the space between the processing surfaces 1 and 2 and the oxide raw material liquid for shell were mixed inside the vessel v, and collected in the beaker b. pH of the dispersion collected in the beaker b was 13.89 (measurement temperature 29.6° C.). Dry powders and wet cake sample were prepared from the dispersion collected in the beaker b. The time from introduction of liquid B into the space between the processing surfaces 1 and 2 until discharge of the iron oxide particle dispersion from the space between the processing surfaces 1 and 2 followed by collection of the mixed fluid of the discharged iron oxide particle dispersion and oxide raw material liquid for shell, was 0.8 seconds for most of the particles, and was within 1 second. As a result of the TEM observation of the core-shell type oxide particles produced by the method of Example 10, core-shell type oxide particles wherein the entire surface of one single iron oxide particle is uniformly coated with a silicon oxide, namely silicon oxide-coated iron oxide particles were observed as in Examples 8 and 9. The particle diameter (D) was 9.90 nm, the thickness of the shell oxide (coating thickness) was 1.17 nm, and D/Dc of the silicon oxide coated iron oxide particles was 131.0%.

Comparative Example 11

Using the same formulations as in Example 9, and the high-speed rotary dispersion emulsification apparatus CLEARMIX (Product name: CLM-2.2S, M Technique Co., Ltd.), the oxide raw material liquid for core, oxide precipitation solvent, and oxide raw material liquid for shell were prepared. Next, the prepared oxide raw material liquid for core and oxide precipitation solvent were mixed and stirred in a pressurized vessel using a stirrer. The rotational speed of the stirrer was 600 rpm. Specifically, while 4,000 ml of the oxide raw material liquid for core (pure water 98.00/Fe $(NO_3)_3 \cdot 9H_2O$ 2.0) (weight ratio) as the first fluid to be processed was stirred at 142° C., 500 ml of the oxide precipitation solvent (NaOH 9.00/pure water 91.00) (weight ratio) as the second fluid to be processed was introduced thereto at 86° C. over 10 minutes, to precipitate iron oxide particles and to obtain an iron oxide particle dispersion. pH of the iron oxide particle dispersion was 12.64 (measurement temperature 33.2° C.). The iron oxide particles in the obtained iron oxide particle dispersion had been already aggregated.

Next, the obtained iron oxide particle dispersion as liquid A was introduced into the space between the processing surfaces 1 and 2 at 142° C. and at 450 ml/min using the fluid processing apparatus of FIG. 1(B), and while driving the processing member 10 at a rotational speed of 1,130 rpm, the oxide raw material liquid for shell (pure water 93.70/97 wt % $H_2SO_4$ 5.11/TEOS 1.19) (weight ratio) as liquid B was introduced at 89° C. and at 100 ml/min into the space between the processing surfaces 1 and 2. The iron oxide particle dispersion and the oxide raw material liquid for shell were mixed in the thin film fluid, and an oxide for shell was precipitated on the surface of the iron oxide particles. A discharged liquid containing the core-shell type oxide particles (hereinafter, referred to as core-shell type oxide particle dispersion) was discharged from the space between the processing surfaces 1 and 2 of the fluid processing apparatus. The discharged core-shell type oxide particle dispersion was collected in the beaker b through the vessel v. pH of the discharged liquid was 11.88 (measured temperature 32.4° C.). The time from setting the collected iron oxide dispersion in the fluid processing apparatus until discharge of the dispersion from the space between the processing surfaces 1 and 2 was 10 minutes for most of the particles, and the total processing time of Comparative Example 11 was 20 minutes. Dry powders and wet cake sample were prepared from the dispersion collected in the beaker b. As a result of TEM observation of the core-shell type oxide particles produced by the method of Comparative Example 11, the iron oxide particles wherein the entire surface of one single iron oxide particle was uniformly coated with a silicon oxide as obtained in Examples 8 and 9, were not observed, and many particles wherein a plurality of iron oxide particles were coated with a silicon oxide shell were observed, and D/Dc of the particles was 433%.

Comparative Example 12

Iron oxide particles whose surface was not coated with a silicon oxide were prepared for comparison with iron oxide particles whose surface was coated with a silicon oxide.

Using the same formulations of the oxide raw material liquid for core and oxide precipitation solvent as those in Examples 8 and 9, and the high-speed rotary dispersion emulsification apparatus CLEARMIX (Product name: CLM-2.2S, M Technique Co., Ltd.), the oxide raw material liquid for core and oxide precipitation solvent were prepared.

Next, the prepared oxide raw material liquid for core and oxide precipitation solvent and the fluid processing apparatus shown in FIG. 1(B) were used to prepare the iron oxide particles under the following conditions. Specifically, the oxide raw material liquid for core (pure water 98.00/Fe $(NO_3)_3 \cdot 9H_2O$ 2.0) (weight ratio) as liquid A was introduced into the space between the processing surfaces 1 and 2 at 142° C. and at 400 ml/min. While driving the processing member 10 at a rotational speed of 1,130 rpm, the oxide precipitation solvent (NaOH 9.00/pure water 91.00) (weight ratio) as liquid B was introduced into the space between the processing surfaces 1 and 2 at 86° C. and at 50 ml/min. The oxide raw material liquid for core and oxide precipitation solvent were mixed in the thin film fluid to precipitate the iron oxide particles between the processing surfaces 1 and 2. A discharged liquid containing the iron oxide particles (hereinafter, referred to as iron oxide particle dispersion) was discharged from the space between the processing surfaces 1 and 2 of the fluid processing apparatus. The washing method of particles, the analysis/evaluation method and the like are the same as in Example 8. The particle diameter measured in the same method as that of the core particle diameter in Example 8 was 6.40 nm, and from the XRD measurement results, only peaks of iron oxide were detected. pH of the discharged liquid was 13.89 (measurement temperature 29.6° C.). The iron oxide particles in the resulting iron oxide particle dispersion had been already aggregated.

Example 11

In Example 11, the silicon oxide-coated iron oxide particles were prepared in the same manner as in Example 8 except for using an apparatus described in JP 2009-112892, and using a method of mixing and reacting liquid A (oxide raw material liquid for core), liquid B (oxide precipitation solvent) and liquid C (oxide raw material liquid for shell). Here, the apparatus of JP 2009-112892 is an apparatus described in FIG. 4 of JP 2009-112892, wherein the inner diameter of the stirring tank is uniform and is 420 mm, and the gap between the outer end of the mixing tool and the inner peripheral surface of the stirring tank is 1 mm, and the rotor rotational speed of the stirring blade was the same as the rotor rotational speed (1,130 rpm) of the processing member in the fluid processing apparatus shown in FIG. 1(A) used in Example 8. Further, liquid A was introduced into the stirring tank, and liquid B was added, mixed and reacted in the thin film consisting of liquid A that was crimped to the inner peripheral surface of the stirring tank. Then, liquid C was added, mixed and reacted in the thin film consisting of the mixed liquid of liquid A and liquid B that was crimped to the inner peripheral surface of the stirring tank. As a result of TEM observation, silicon oxide-coated iron oxide particles wherein the core was one single iron oxide particle and the shell was a silicon oxide, and the entire surface of the core was uniformly coated with shell, were observed, and a coating layer (shell) of silicon oxide having a thickness of 1.0 to 2.0 nm on the entire surface of the core iron oxide particle was observed. As a result of a mapping result using STEM of the silicon oxide-coated iron oxide particles obtained in Example 11 as in Example 8, distribution of oxygens (O) in the entire particles was observed in the observed particles in the HAADF image, and distribution of iron (Fe) in about 1.0 to 2.0 nm smaller area in radius compared with the particles was observed, and distribution of silicon (Si) only in the coating layer was mainly observed. The particle diameter (D) was 16.9 nm, the thickness of the shell oxide (coating thickness) was 1.0 to 2.0 nm, and D/Dc of the silicon oxide-coated iron oxide particles was 111.8 to 123.7%. From the XRD measurement results of the silicon oxide-coated iron oxide particles obtained in Example 11, peaks derived from iron oxide ($Fe_2O_3$) were detected, and no other peaks were observed.

Figure 16:
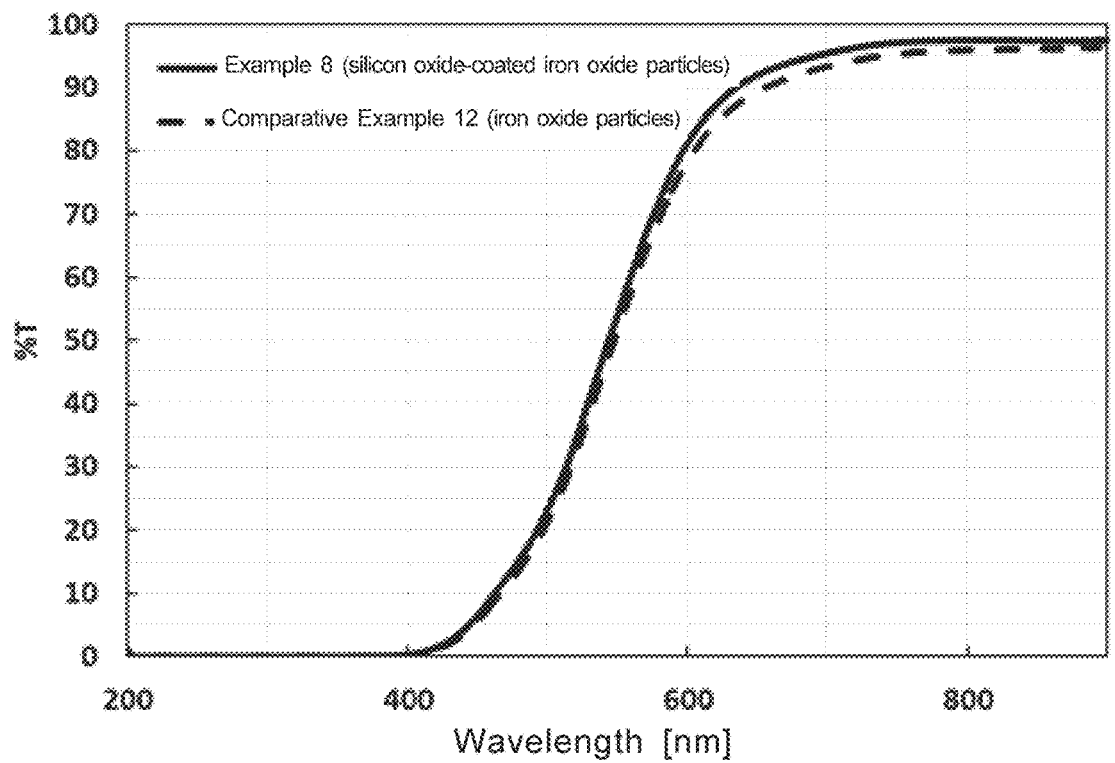
FIG. 16 shows a transmission spectrum of the core-shell type oxide particles obtained in Example 8 of the present invention, and of the oxide particles obtained in Comparative Example 12.
Figure 17:
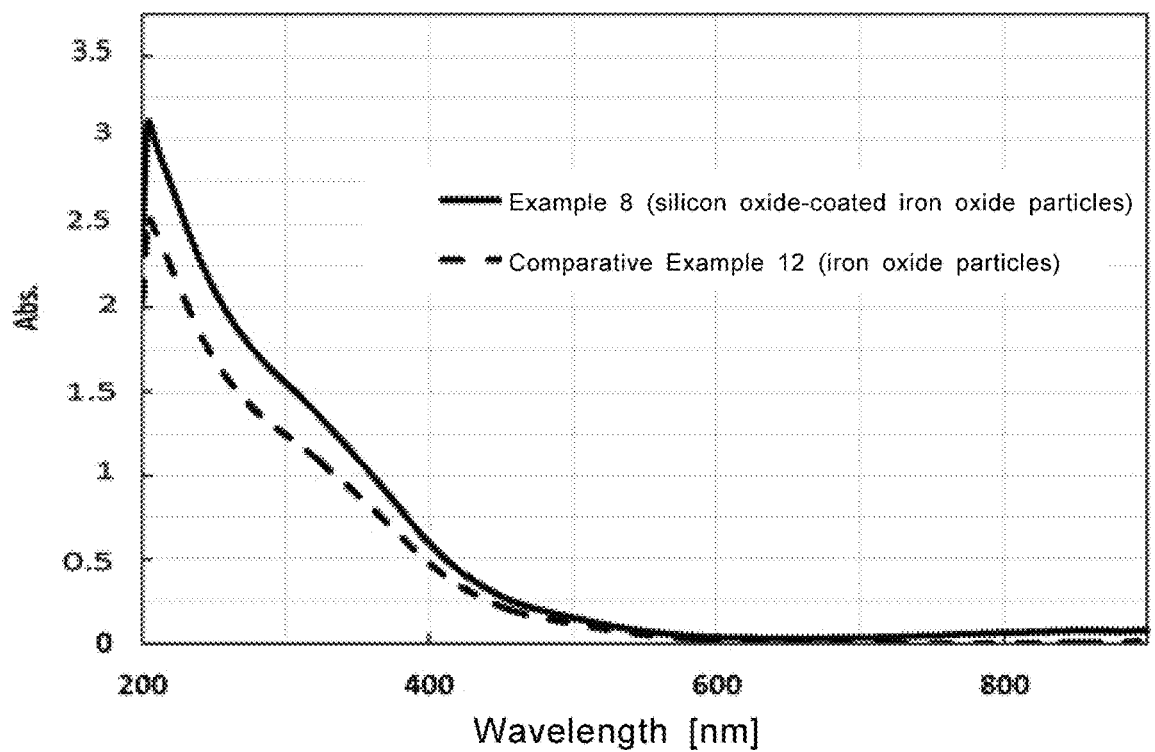
FIG. 17 shows an absorption spectrum of the core-shell type oxide particles obtained in Example 8 of the present invention, and of the oxide particles obtained in Comparative Example 12.

Regarding the silicon oxide-coated iron oxide particles obtained under the conditions of Example 8 and the iron oxide particles obtained in Comparative Example 12, the dispersion wherein the silicon oxide-coated iron oxide particles were dispersed in propylene glycol at a $Fe_2O_3$ concentration of 0.05 wt % was prepared as a measurement sample for transmission spectrum, and the dispersion wherein the silicon oxide-coated iron oxide particles were dispersed in propylene glycol at a $Fe_2O_3$ concentration of 0.007 wt % (0.0005 mol/L) was prepared as a measurement sample for absorption spectrum. Spectra of both dispersions were measured. The ultraviolet-visible absorption spectroscopic measurement results of both dispersions are shown in FIG. 16 (transmittance) and FIG. 17 (absorbance). As shown from FIG. 16 and FIG. 17, it was found that the dispersion prepared by dispersing the iron oxide particles obtained in Example 8 wherein the entire surface of the iron oxide was uniformly coated with a silicon oxide, easily absorbed strongly a light of a wavelength of the absorption region 200 to 400 nm, and easily transmitted a light of a wavelength of the transmission region 450 to 800 nm, compared with the dispersion prepared by dispersing the iron oxide particles obtained in Comparative Example 12. It is considered that affinity with the solvent is improved and dispersibility of the particles is improved by uniformly coating the entire surface of one single iron oxide particle with a silicon oxide. Regarding the silicon oxide-coated iron oxide particles obtained under the conditions of Example 11, it was also found that the dispersion of Example 11 easily absorbed strongly a light of a wavelength of the absorption region 200 to 400 nm, and easily transmitted a light of a wavelength of the transmission region 450 to 800 nm, though the particles obtained in Example 11 do not have as much characteristics as those of the particles obtained in Example 8.

(Photocatalytic Activity Evaluation)

Figure 18:
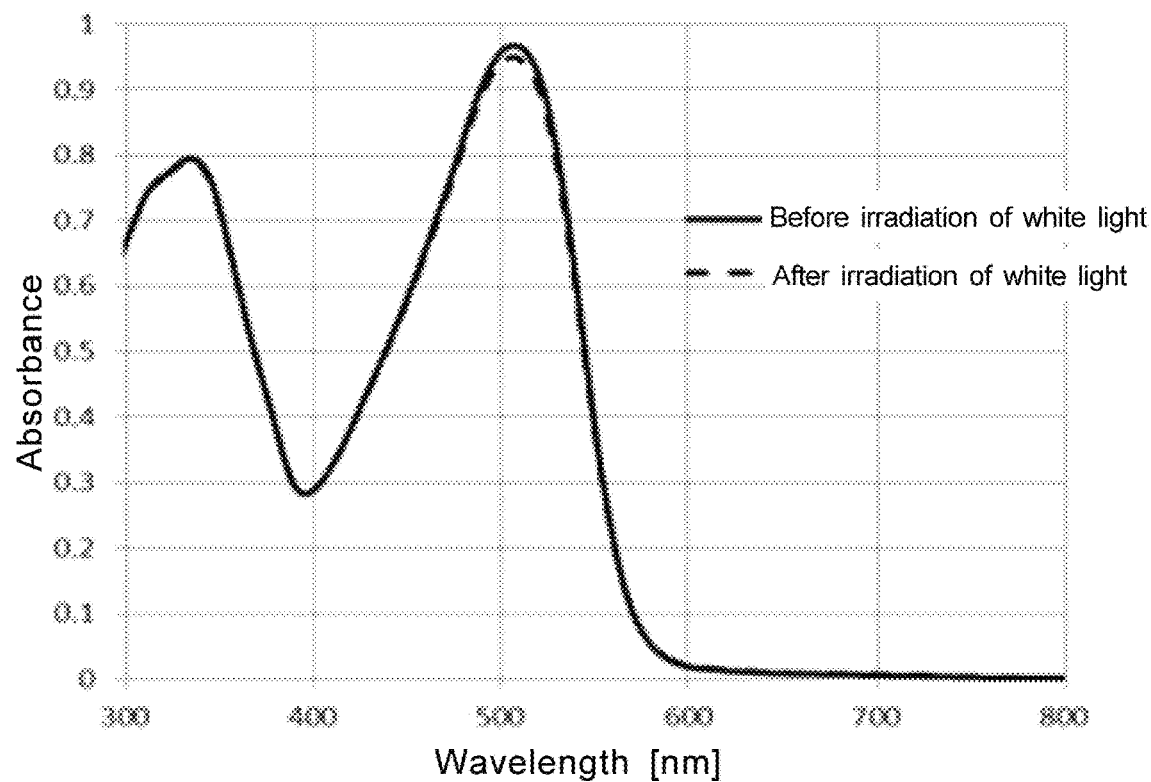
FIG. 18 shows an absorption spectrum of a dispersion in which the core-shell type oxide particles obtained in Example 8 of the present invention are dispersed in propylene glycol dissolving Congo red dye, before and after irradiation with a white light for 2 hours.
Figure 19:
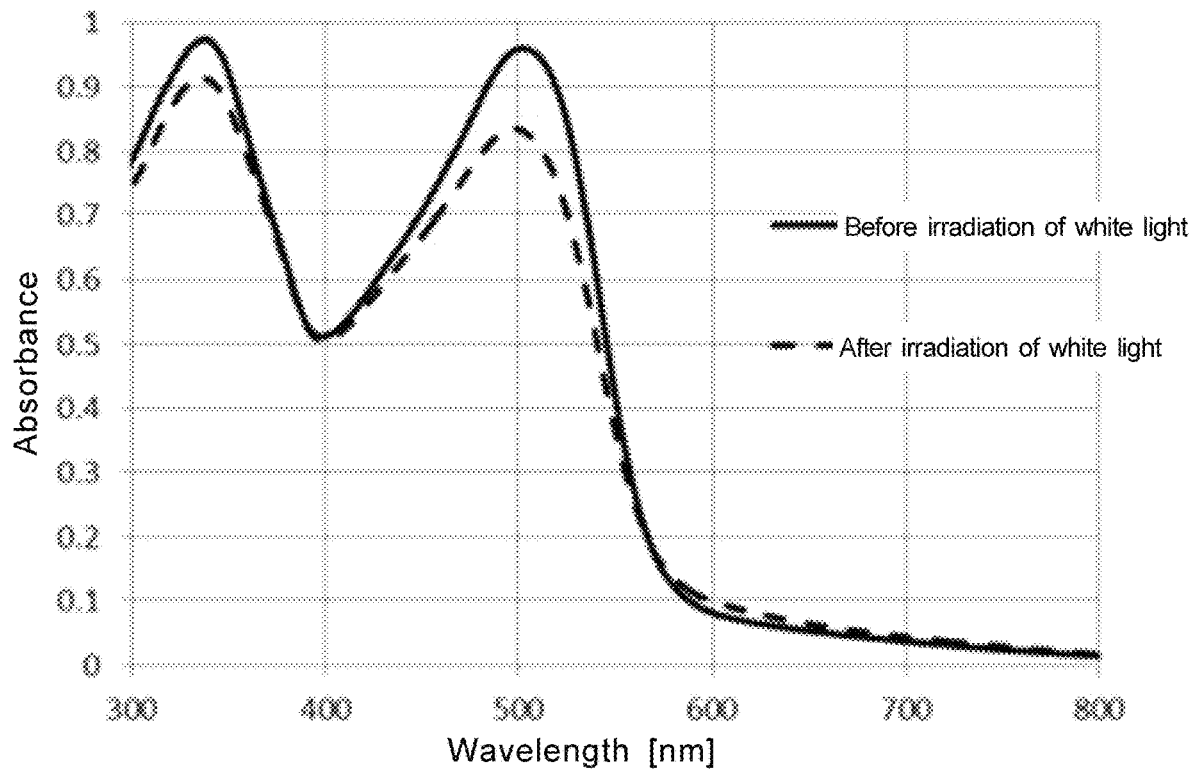
FIG. 19 shows an absorption spectrum of a dispersion in which the oxide particles obtained in Comparative Example 12 of the present invention are dispersed in propylene glycol dissolving Congo red dye, before and after irradiation with a white light for 2 hours.

Photocatalytic activities of the particles obtained in Examples 8 to 10 and Comparative Examples 8 to 12 were evaluated. Specifically, the particles obtained in Examples or Comparative Examples were dispersed in propylene glycol dissolving Congo red dye, and a white light was irradiated for 2 hours, and ultraviolet-visible absorption spectra were measured before and after irradiation. 250 W Metal halide light source device (UF 3250 NAC, Ushio Lighting Inc.) equipped with a metal halide lamp (ULRD-250ST/9H2, Ushio Lighting Inc.) was used for irradiation of a white light. Photocatalytic activity was evaluated by attenuation rate of absorbance (Formula 1) for a light of a wavelength around 505 nm derived from the absorption peak of the Congo red dye. A concentration of Congo red dye in propylene glycol was set so that the absorbance for a wavelength 505 nm was around 1, and the dispersion concentration of the particles was set to $5 \times 10^{-5}$ mol/L. FIG. 18 shows the absorption spectrum measurement results of the particles obtained under the conditions of Example 8 before and after irradiation with a white light. FIG. 19 shows the absorption spectrum measurement results of the particles obtained under the conditions of Comparative Example 12 before and after irradiation with a white light. In the case of the silicon oxide-coated iron oxide particles obtained in Example 8, substantially no changes were observed in the absorbance for a light of a wavelength 505 nm, before and after irradiation with a white light for 2 hours (the absorbance after irradiation was 0.98 to 1.00, when the absorbance before irradiation was 1). In the case of the particles prepared in Comparative Example 12, the absorbance was attenuated, and the absorbance after irradiation fell to less than 0.90, when the absorbance before irradiation was 1. The particles produced under the conditions of Comparative Examples 8 to 11 showed the same tendency as in Comparative Example 12. It was found that with respect to the particles produced under the conditions of Examples 8 to 10, photocatalytic ability of the iron oxide particles could be suppressed by uniformly coating the entire surface of one single iron oxide particle with a silicon oxide, but with respect to the particles produced under the conditions of Comparative Examples 8 to 11, photocatalytic ability of the iron oxide could not be suppressed because the iron oxide particles included those wherein the surface of the iron oxide particles were not coated with a silicon oxide or those wherein the surface of a plurality of iron oxide particles were coated with a silicon oxide.

Next, further experiments were conducted on the dispersions wherein the silicon oxide-coated iron oxide particles obtained in Example 8 and the silicon oxide-coated iron oxide particles obtained in Example 11 were dispersed in a dispersion medium.

(Transmission Spectrum and Absorption Spectrum)

For the transmission spectrum and the absorption spectrum, the ultraviolet-visible absorption spectrophotometer (product name: UV-2450, Shimadzu Corporation) was used. The measurement range was from 200 nm to 800 nm, and the sampling rate was 0.2 nm, and the measurement speed was slow speed. For the transmission spectrum, the dispersion prepared by dispersing the silicon oxide-coated iron oxide in propylene glycol at a $Fe_2O_3$ concentration of 0.05 wt % were used as a measurement sample. For the absorption spectrum, the dispersion prepared by dispersing the silicon oxide-coated iron oxide in propylene glycol at a $Fe_2O_3$ concentration of 0.007 wt % (0.0005 mol/L) were used as a measurement sample. After measuring the absorption spectrum, the molar absorption coefficient for each measurement wavelength was calculated from the absorbance obtained from the measurement result and the iron oxide concentration (as $Fe_2O_3$) in the dispersion, and the graph was prepared showing the measurement wavelength on the horizontal axis and the molar absorption coefficient on vertical axis. A liquid cell of thickness of 1 cm was used for measurements.

(Haze Value Measurement)

For the haze value measurement, the haze value meter (Model HZ-V3, Suga Test Instruments Co., Ltd.) was used. The optical condition was the double-beam method and D65 light as a light source which corresponds to JIS K 7136 and JIS K 7361. Measurement was performed on the same dispersion used for ultraviolet-visible absorption and transmission spectrum measurement in a liquid cell having a thickness of 1 mm.

(Reflection Spectrum)

For the reflection spectrum, the ultraviolet-visible-near infrared spectrophotometer (product name: SolidSpec-3700, Shimadzu Corporation) was used. Measurement range was 400 to 750 nm, and the sampling rate was 2.0 nm, and the measurement speed was medium speed. For a background measurement in measuring powders, the standard white plate (product name: Spectralon™, Labsphere Inc.) was used, and for a background measurement in measuring dispersions, barium sulfate was used. As a measurement sample, powders of a silicon oxide-coated iron oxide and a dispersion prepared by dispersing a silicon oxide-coated iron oxide in water at a $Fe_2O_3$ concentration of 0.31 wt % were used as described later.

Comparative Example 13

Figure 24:
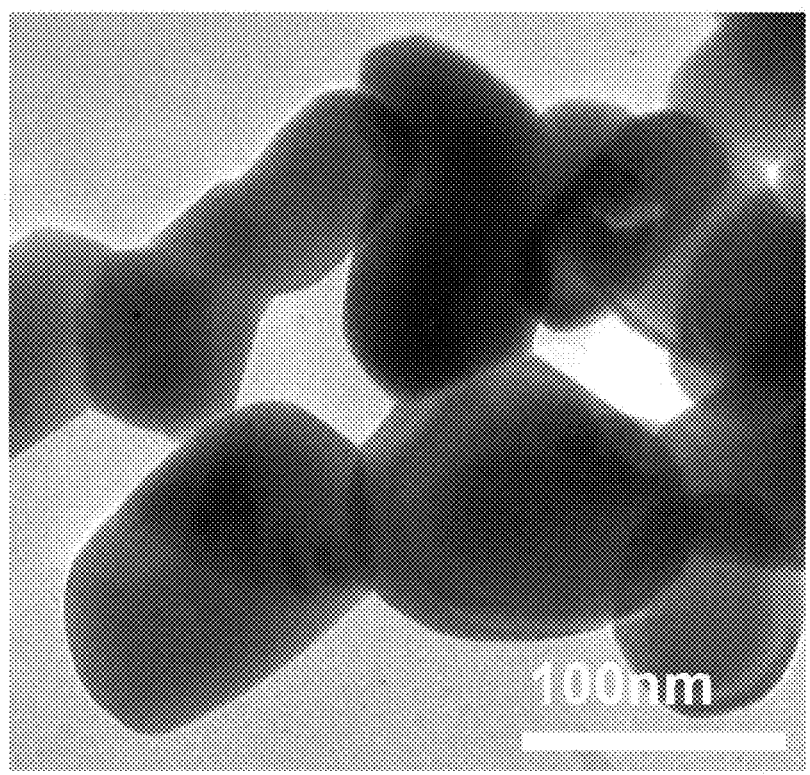
FIG. 24 shows a TEM photograph of the oxide particles obtained in Comparative Example 13 of the present invention.

Iron oxide (III) (α-$Fe_2O_3$) made by Wako Pure Chemical Industries, Ltd. as Comparative Example 13 was dispersed in propylene glycol or water in the same manner as in Example 8. TEM observation, haze value, ultraviolet-visible transmission absorption spectrum, reflection spectrum, and XRD were measured in the same manner as in Example 8. FIG. 24 shows a TEM photograph of the iron oxide particles of Comparative Example 13. The average primary particle diameter was 119.6 nm. In preparing TEM observation sample of Comparative Example 13, the above commercially available iron oxide (III) (α-$Fe_2O_3$) was used without washing.

Comparative Example 12 was used as iron oxide particles whose surface was not coated with a silicon oxide, for comparison with iron oxide particles whose surface was coated with a silicon oxide.

In the XRD measurement results, peaks of α-$Fe_2O_3$ (hematite) were clearly detected in Examples 8 and 11, and Comparative Examples 12 and 13. As described above, in Examples 8 and 11, peaks of silicon oxide coating on the surface of the particles were not detected, and thus, the silicon oxide is considered to be amorphous.

The transmission spectrum of the dispersion prepared by dispersing the silicon oxide-coated iron oxide particles obtained in Example 8 in propylene glycol, and of the dispersion prepared by dispersing the iron oxide particles of Comparative Examples 12 and 13 in propylene glycol were shown in FIG. 20. The silicon oxide-coated iron oxide particle dispersion obtained in Example 8 did not substantially transmit an ultraviolet light of a wavelength of 200 to 400 nm, and the transmittance for a wavelength of 420 nm was 1.64%. The silicon oxide-coated iron oxide particle dispersion obtained in Comparative Example 12 also did not substantially transmit an ultraviolet light of a wavelength of 200 to 400 nm, and the transmittance for a wavelength of 420 nm was 1.73%. It was found that the transmittance of the silicon oxide-coated iron oxide particle dispersion obtained in Example 8 and Comparative Example 12 for a wavelength of 620 to 800 nm exceeded 80%. Namely, it was found that a light of a wavelength of 200 to 420 nm was absorbed and other lights, particularly a light of a wavelength of 620 to 800 nm were transmitted. In contrast, the transmittance of the iron oxide particle dispersion of Comparative Example 13 was approximately 10% over the entire measurement range, and no clear difference was found between the absorption region and the transmission region. In addition, the silicon oxide-coated iron oxide particle dispersion obtained in Example 11 did not substantially transmit an ultraviolet light of a wavelength of 200 to 400 nm, and the transmittance for a wavelength of 420 nm was 1.89%. It was found that the transmittance for a wavelength of 620 to 800 nm exceeded 80%, though the particles obtained in Example 11 do not have as much characteristics as those of the particles obtained in Example 8.

The molar absorption coefficients were calculated from the absorbance obtained from the absorption spectrum measurement results of the dispersions wherein the silicon oxide-coated iron oxide particles obtained in Example 8 in propylene glycol, and of the dispersions wherein the iron oxide particles of Comparative Examples 12 and 13 in propylene glycol, and the iron oxide concentration (as $Fe_2O_3$) in the measurement liquids. The graph showing the measurement wavelength on horizontal axis and the molar absorption coefficient on vertical axis is shown in FIG. 21. As shown in FIG. 21, the molar absorption coefficient of the iron oxide particles obtained in Example 8 was 1,193 L/(mol·cm) for a light of a wavelength of 400 nm, and was 5,479 L/(mol·cm) for a light of a wavelength of 220 nm. The molar absorption coefficient of the iron oxide particles obtained in Comparative Example 12 was 952 L/(mol·cm) for a light of a wavelength of 400 nm, and was 4,488 L/(mol·cm) for a light of a wavelength of 220 nm. In contrast, the molar absorption coefficient of the iron oxide particles of Comparative Example 13 was 50 to 150 L/(mol·cm) over the entire measurement range. The molar absorption coefficient of the iron oxide particles obtained in Example 11 was 595 L/(mol·cm) for a light of a wavelength of 400 nm, and was 3,112 L/(mol·cm) for a light of a wavelength of 220 nm.

FIG. 22 shows the reflection spectrum measurement results of powders of the silicon oxide-coated iron oxide particles obtained in Example 8, and of powders of the iron oxide particles obtained in Comparative Examples 12 and 13. As shown in FIG. 22, while the reflectance of the silicon oxide-coated iron oxide particles obtained in Example 8 for a light of a wavelength range of 400 to 620 nm was less than 18%, the reflectance of the iron oxide particles obtained in Comparative Examples 12 and 13 exceeded 18%. FIG. 23 shows the reflection spectrum measurement results of a dispersion prepared by dispersing the silicon oxide-coated iron oxide particles obtained in Example 8 in water at a $Fe_2O_3$ concentration of 0.31 wt %. As shown in FIG. 23, while the reflectance of the silicon oxide-coated iron oxide particles obtained in Example 8 for a light of a wavelength range of 400 to 620 nm was less than 18%, the reflectance of the iron oxide particles obtained in Comparative Examples 12 and 13 exceeded 18%. The reflectance of the silicon oxide-coated iron oxide particles obtained in Example 11 for a light of a wavelength range of 400 to 620 nm was less than 18%.

The haze value of the dispersion prepared by dispersing the silicon oxide-coated iron oxide particles obtained in above Example 8 in propylene glycol at a $Fe_2O_3$ concentration of 0.05 wt % was 0.00%, and the haze value of the dispersion prepared by dispersing the particles in water at a $Fe_2O_3$ concentration of 0.31 wt % was 0.08%. Accordingly both dispersions were highly transparent dispersions. The haze value of the dispersion prepared by dispersing the silicon oxide-coated iron oxide particles obtained in above Example 8 in water at a $Fe_2O_3$ concentration of 2.0 wt % was 0.89%. Accordingly the dispersion was a highly transparent dispersion. On the other hand, the haze value of the dispersion obtained by dispersing the iron oxide particles of Comparative Example 13 in propylene glycol at a concentration of 0.02 wt % was 21.9%, and the haze value of the dispersion dispersed in water at a concentration of 0.31 wt % was 15.9 wt %, and the haze value of the dispersion dispersed in pure water at a concentration of 2.0% was 23.4%. Obvious turbidity was observed in the dispersions. Further, the haze value of the dispersion prepared by dispersing the iron oxide particles obtained in Comparative Example 12 in water at a concentration of 2.0 wt % was 2.56%, and turbidity was observed. The haze value of the dispersion prepared by dispersing the silicon oxide-coated iron oxide particles obtained in Example 11 in propylene glycol at a $Fe_2O_3$ concentration of 0.05 wt % was 0.91%, and the haze value of the dispersion dispersed in water at a $Fe_2O_3$ concentration of 0.31 wt % was 1.46%. The dispersions were highly transparent dispersions, though the transparency was not as high as that of the silicon-coated iron oxide particles obtained in Example 8. Further, the haze value of the dispersion prepared by dispersing the silicon oxide-coated iron oxide particles obtained in Example 11 in water at a $Fe_2O_3$ concentration of 2.0 wt % was 1.64%, and the dispersion was a highly transparent dispersion, though the transparency was not as high as that of the silicon-coated iron oxide particles obtained in Example 8.

From the above, the transmission and absorption spectrum, reflection spectrum, primary particle diameter, and the haze value of the silicon oxide-coated iron oxide particles obtained in Example 8 and Example 11 or the compositions thereof, do not impair coloring of the original coating material, color characteristics, textures or appearance, or designability of a product, particularly when used in a red coating material, and the silicon oxide-coated iron oxide particles or the compositions thereof can be suitably used. However, the iron oxide particles of Comparative Example 13 do not have a clear difference in the transmission region and the absorption region in the ultraviolet and visible region, and have strong reflection characteristics in the red region, so that coloring of the original red coating material, color characteristics, textures or appearance, or designability of a product are impaired. With respect to the iron oxide particles of Comparative Example 12 wherein the surface was not coated with a silicon oxide, the reflectance for a light of a wavelength range of 400 to 620 nm exceeds 18%, and the iron oxide particles reflected lights other than a red light. The iron oxide particle powders were yellowish in appearance as compared with the silicon oxide-coated iron oxide particles obtained in Example 8. Thus, the iron oxide particles impair coloring of the original red coating material, color characteristics, textures or appearance, or designability of a product.

REFERENCE SIGNS LIST 1 the first processing surface
2 the second processing surface
10 the first processing member
11 the first holder
20 the second processing member
21 the second holder
d1 the first introduction part
d2 the second introduction part
d3 the third introduction part
d10 opening
d20 opening
d30 opening

The invention claimed is:

1. A silicon oxide-coated iron oxide composition for red coating, containing iron oxide particles wherein at least a part of the surface of the iron oxide particles is coated with a silicon oxide, wherein reflectance for a light of a wavelength of 400 to 620 nm is less than 18%, and a primary particle diameter of the iron oxide particles is 1 to 50 nm, and the silicon oxide is amorphous and the iron oxide particles are $\alpha$-$Fe_2O_3$.

2. The silicon oxide-coated iron oxide composition for red coating according to claim 1, wherein transmittance of a dispersion containing the iron oxide particles for a light of a wavelength of 200 to 420 nm is 2.0% or less, and transmittance of the dispersion for a light of a wavelength of 620 to 800 nm is 80% or more.

3. The silicon oxide-coated iron oxide composition for red coating according to claim 1, wherein haze value of a dispersion containing the iron oxide particles is 2.0% or less at the concentration of 2 wt % of the iron oxide in the dispersion.

4. The silicon oxide-coated iron oxide composition for red coating according to claim 1, which is a weather resistant composition for coating which is blended and used in a coating material constituting a coated body, and has prescribed reflectance, transmittance and transparency, and protects the coated body from an ultraviolet light,
wherein the weather resistant composition comprises core-shell type iron oxide particles wherein the surface of the core iron oxide particles is coated with a shell silicon oxide;
a primary particle diameter of the core-shell type iron oxide particles is 1 to 50 nm;
reflectance of the core-shell type iron oxide particle for a light of a wavelength of 400 to 620 nm is less than 18%;
transmittance of a dispersion prepared by dispersing the core-shell type iron oxide particles in propylene glycol at the concentration of 0.05 wt % of the iron oxide for a light of a wavelength of 200 to 420 nm is 2.0% or less, and transmittance of the dispersion for a light of a wavelength of 620 to 800 nm is 80% or more; and
haze value of a dispersion prepared by dispersing the core-shell type iron oxide particles in propylene glycol or water at the concentration of 2 wt % of the iron oxide is 2.0% or less.

5. The weather resistant composition for red coating according to claim 4, wherein a primary particle diameter of the core-shell type iron oxide particles is 100.5% or more and 190% or less relative to the primary particle diameter of the core iron oxide particle.

6. A method for producing the silicon oxide-coated iron oxide composition for red coating according to claim 1 wherein the surface of the core iron oxide particles having a primary particle diameter of 1 to 50 nm are coated with the shell oxide, wherein the shell oxide is an amorphous silicon oxide, and the core iron oxide particles are $\alpha$-$Fe_2O_3$, the method comprising at least two steps of:
Step 1 of precipitating the core iron oxide particles in a mixed fluid prepared by mixing an oxide raw material liquid for core containing at least an oxide raw material for core which is a raw material of the core iron oxide particles, and an oxide precipitation solvent containing at least an oxide precipitation substance for precipitating the core iron oxide particles; and
Step 2 of coating the entire surface of the core iron oxide particles uniformly with the shell oxide by mixing the mixed fluid and an oxide raw material liquid for shell containing at least a shell oxide raw material which is a raw material of the shell oxide; and
wherein the at least two steps are performed continuously between at least two processing surfaces which are capable of approaching to and separating from each other, at least one of which rotates relatively to the other.

7. The method of producing core-shell type oxide particles according to claim 6, wherein after Step 1, Step 2 is completed within a prescribed time during which the core iron oxide particles do not aggregate in the mixed fluid.

8. The method of producing core-shell type oxide particles according to claim 7, wherein the prescribed time is within 1 second.

9. The method of producing core-shell type oxide particles according to claim 6, wherein Step 1 and Step 2 are controlled so that the primary particle diameter of the core-shell type oxide particles is 190% or less relative to the primary particle diameter of the core iron oxide particles.

10. The method of producing core-shell type oxide particles according to claim 6, wherein the center side of the at least two processing surfaces is disposed at an upstream side and the outside is disposed at a downstream side;

either one of the oxide raw material liquid for core and the oxide precipitation solvent as the first fluid passes from the upstream side to the downstream side between the at least two processing surfaces, while forming a thin film fluid;

the other of the oxide raw material liquid for core and the oxide precipitation solvent as the second fluid is introduced into the space between the at least two processing surfaces from an opening formed on at least either one of the at least two processing surfaces through the second passage independent from the first passage which the first fluid is introduced into the space between the at least two processing surfaces through, and then the oxide raw material liquid for core and the oxide precipitation solvent are mixed between the at least two processing surfaces to precipitate the core iron oxide particles;

the oxide raw material liquid for shell is introduced into the space between the at least two processing surfaces from an opening formed on at least either one of the at least two processing surfaces through the third passage independent from the first passage and the second passage; and the opening of the second passage is provided at the upstream side of the opening of the third passage.

11. The method of producing core-shell type oxide particles according to claim 10, wherein the following equations are satisfied:

$$F1>F2 \text{ and } F1+F2>F3$$

wherein F1 is a flow rate of the first fluid introduced in the space between the at least two processing surfaces, F2 is a flow rate of the second fluid introduced in the space between the at least two processing surfaces, and F3 is a flow rate of the third fluid introduced in the space between the at least two processing surfaces.

12. The method of producing core-shell type oxide particles according to claim 6, wherein thickness of the shell oxide is 0.5% to 25% relative to the diameter of the core-shell type oxide particles.

13. The method of producing core-shell type oxide particles according to claim 6, wherein after irradiating a white light for at least 2 hours to a dispersion containing Congo red dye in which the core-shell type oxide particles are dispersed, an attenuation rate of absorbance derived from Congo red dye for a light of a wavelength of around 505 nm is 10% or less.

14. The method of producing core-shell type oxide particles according to claim 6, wherein the shell oxide contains an element different from an element contained in the core iron oxide particles.

* * * * *